United States Patent [19]
Croce et al.

[11] Patent Number: 5,633,136
[45] Date of Patent: May 27, 1997

[54] ALL-1 POLYNUCLEOTIDES FOR LEUKEMIA DETECTION AND TREATMENT

[75] Inventors: Carlo Croce, Philadelphia; Eli Canaani, Glenside, both of Pa.

[73] Assignee: Thomas Jefferson University, Philadelphia, Pa.

[21] Appl. No.: 327,392

[22] Filed: Oct. 19, 1994

Related U.S. Application Data

[63] Continuation of Ser. No. 971,094, Oct. 30, 1992, abandoned, which is a continuation-in-part of Ser. No. 888,839, May 27, 1992, abandoned, which is a continuation-in-part of Ser. No. 805,093, Dec. 11, 1991, abandoned.

[51] Int. Cl.$^6$ ............................ C12Q 1/68; C07H 21/02; C07H 21/04
[52] U.S. Cl. ............................ 435/6; 435/91.2; 536/23.1; 536/24.3; 536/24.31; 536/24.33
[58] Field of Search ............ 435/6, 91.2; 536/24.3–24.33, 536/23.1

[56] References Cited

PUBLICATIONS

Sacchi, N. et al. Hu–ets–1 and Hu–ets–2 Genes are Transposed in Acute Leukemias with (4;11) and (8;21) Translocations. Science (Jan. 24, 1986) 231:379–382.

Bowden, D.W. et al. Studies on Locus Expansion, Library Representation, and Chromosome Walking Using an Efficient Method to Screen Cosmid Libraries, Gene (1988)71:391–400.

Djabali, M., et al. A Trithorax–Like Gene is Interrupted by Chromosome 11q 23 Translocations in Acute Leukemias, Nature Genet. (1992) 2:113–118.

Adams et al., "Sequence Identification of 2,375 Human Brain Genes", Nature 355: 632–634 1992.

Arad et al., "Use of Reconstituted Sendai Virus Envelopes for Fusion–Mediated Microinjection of Double–Stranded RNA: Inhibition of Protein Synthesis in Interferon–Treated Cells", Biochem. Biophy. Acta. 859:88–94 1986.

Capdevila and Garcia–Bellido, "Genes Involved in the Activation of the Bithorax Complex of Drosophila", Roux's Arch. Dev. Biol. 190: 339–350 1981.

Chu et al., "Mosaic Structure of Globular Domains in the Human Type VI Collagen α3 Chain: Similarity to Von Wilebrand Factor, Fibronectin, Actin, Salivary Proteins and Aprotinin Type Protease Inhibitors", EMBO J. 9: 385–393 1990.

Cimino et al., "Cloning of ALL–1, the Locus Involved in Leukemias with the t(4;11) (q21;q23), t(9;11) (p22;q23), and t(11;19) (q23;p13) Chromosome Translocations", Cancer Research 51 6712–6714 1991.

Cimino et al., "An Altered 11–Kilobase Transcript in Leukemic Cell Lines with the t(4;11) (q21;q23) Chromosome Translocation", Cancer Research 52: 3811–3813 1992.

(List continued on next page.)

Primary Examiner—W. Gary Jones
Assistant Examiner—Dianne Rees
Attorney, Agent, or Firm—Woodcock Washburn Kurtz Mackiewicz & Norris

[57] ABSTRACT

Methods are provided for the diagnosis and treatment of human leukemias involving breakpoints on chromosome 11 in the ALL-1 locus. The ALL-1 breakpoint region, an approximately 8 kb region on chromosome 11 is also disclosed. The ALL-1 region is involved in translocations in acute lymphocytic, mylemonocytic, monocytic, and myelogenous leukemias. Probes which identify chromosome aberrations involving the ALL-1 breakpoint region on chromosome 11 are also provided. The cDNA sequence of the ALL-1 gene on chromosome 11 is provided. A partial sequence of the AF-4 gene is also provided in the context of the sequences of the two reciprocal end products of a translocation. Amino acid sequences corresponding to the cDNA sequences of the entire ALL-1 gene and the partial sequence of the AF-4 gene are also provided. Probes are provided for detecting chromosomal abnormalities involving the ALL-1 gene on chromosome 11. Monoclonal antibodies for diagnosis and treatment and antisense oligonucleotides for the treatment of acute leukemias are also described.

16 Claims, 22 Drawing Sheets

OTHER PUBLICATIONS

Cohen et al., "Constitutive Expression and Role in Growth Regulation of Interleukin–1 and Multiple Cytokine Receptors in a Biphenotypic Leukemic Cell Line", *Blood* 78: 94–102 (1991).

Cotter et al., "Gene Mapping by Microdissection and Enzymatic Amplification: Heterogeneity in Leukaemia Associated Breakpoints on Chromosome II", *Genes, Chromosomes & Cancer* 3: 8–15 1991.

Croce, "Role of Chromosome Translocations in Human Neoplasia", *Cell* 49: 155–156 1987.

de Th` et al., "The PLM–RARα Fusion mRNA Generated by the t(15;17) Translocation in Acute Promyelocytic Leukemia Encodes a Functionally Altered RAR", *Cell* 66: 675–684 1991.

Erikson et al., "Heterogeneity of Chromosome 22 Breakpoint in Philadelphia–Positive (Ph$^+$) Acute Lymphocytic Leukemia", *Proc. Natl. Acad. Sci. USA* 83:1807–1811 1986.

Gale and Canaani, "An 8–kilobase abl RNA Transcript in Chronic Myelogenous Leukemia", *Proc. Natl. Acad. Sci. USA* 81: 5648–5652 1984.

Green et al., "Systematic Screening of Yeast Artificial–Chromosome Libraries by Use of the Polymerase Chain Reaction", *Proc. Natl. Acad. Sci. USA* 87: 1213–1217 1990.

Gu et al., "The t(4;11) Chromosome Translocation of Human Acute Leukemias Fuses the ALL–1 Gene, Related to Drosophila trithorax, to the AF–4 Gene", *Cell* 71: 701–708 1992.

Gu et al., "The (4;11) (q21;q23) Chromosome Translocations in Acute Leukemias Involve the VDJ Recombinase", *Proc. Natl. Acad. Sci. USA* 89: 10464–10468 1992.

Heisterkamp et al., "Structural Organization of the BCR Gene and its Role in the Ph' Translocation", *Nature* 315: 758–761 1985.

Hoheisel et al., "Control of Partial Digestion Combining the Enzymes dam methylase and Mbol", *Nuc. Acid Res.* 17: 9571–9582 1989.

Ingham, "Genetic Control of the Spatial Pattern of Selector Gene Expression in Drosophilia", *Cold Spring Harbor Symp. Quant. Biol.* 50: 201–208 1985.

Kakizuka et al., "Chromosomal Translocation t(15;17) in Human Acute Promyelocytic Leukemia Fuses RARα with a Novel Putative Transcription Factor, PLM", *Cell* 66: 663–674 1991.

Kamps et al., "A New Homeobox Gene Contributes the DNA Binding Domain of the t(1;19) Translocation Protein in Pre–B ALL", *Cell* 60 547–555 1990.

Kitazawa et al., "Immunocytochemical Evaluation of AB1–Gene Products in Leukemic Cell Lines", *Med. Oncol Tumor Pharmacother* 7: 35–41 1990 (Abstract).

Kurzrock et al., "Identification of Molecular Variants of p210$^{bcr-abl}$ in Chron Myelogenous Leukemia", *Blood* 70: 233–236 1987.

Lange et al., "Growth Factor Requirements of Childhood Acute Leukemia: Establishment of GM–CSF–Dependent Cell Lines", *Blood* 1987, 70, 192–199.

Lozzio and Lozzio, "Human Chronic Myelogenous Leukemia Cell–Line With Positive Philadelphia Chromosome", *Blood* 45: 321–334 1975.

Marcu et al., "Transcriptionally Active C–MYC Oncogene is Contained Within NIARD, a DNA Sequence Associated with Chromosome Translocations in B–cell Neoplasia", *Proc. Natl. Acad. Sci. USA* 80: 519–523 1983.

Mazo et al., "The Trithorax Gene, a Trans–Acting Regulator of the Bithorax Complex in Drosophila, Encodes a Protein with Zinc–Binding Domains", *Proc. Natl. Acad. Sci. USA* 87: 2112–2116 1990.

McGinnis and Krumlauf, "Homeobox Genes and Axial Patterning", *Cell* 68: 283–302 1992.

McKeon and Brock, "Interactions of the Polycomb Group of Genes with Homeotic Loci of Drosophila", *Roux's Arch. Dev. Biol.* 199: 387–396 1991.

Mellentin et al., "The Gene for Enhancer Binding Proteins E12/E47 Lies at the t(1;19) Breakpoint in Acute Leukemias", *Science* 246: 379–382 1989.

Garvey et al., "Methods in Immunology: A Laboratory Text for Instruction and Research", Third Ed., The Benjamin/Cummings Publishing Company, Chapter 22, 24–30 Reading, MA, 1977.

Mozer and David, "Cloning and Molecular Characterization of the Trithorax Locus of Drosophila Melanogaster", *Proc. Natl. Acad. Sci. USA* 86: 3738–3742 1989.

Nadkarni et al., "Antisense RNA Therapy for CML—An Hypothesis", *Med. Hypotheses* 35: 307–310 1991.

Nagasaka et al., "Four Cases of t(4;11) Acute Leukemia and Its Myelomonocytic Nature in Infants", *Blood* 61: 1174–1181 1983.

Nourse et al., "Chromosomal Translocation t(1;19) Results in Synthesis of a Homeobox Fusion mRNA That Codes for a Potential Chimeric Transcription Factor", *Cell* 60: 535–545 1990.

Pui et al., "Clinical Characteristics and Treatment Outcome of Childhood Acute Lumphoblastic Leukemia With the t(4;11) (q21;q23): A Collaborative Study of 40 Case", *Blood* 77: 440–447 1991.

Rabbitts, "Translocations, Master Genes, and Differences Between the Origins of Acute and Chronic Leukemias", *Cell* 67, 641–644 1991.

Rowley et al., "Mapping Chromosome Band 11q23 in Human Acute Leukemia with Biotinylated Probes: Identification of 11q23 Translocation Breakpoints with a Yeast Artificial Chromosome", *Proc. Natl. Acad. Sci. USA* 87: 9358–9362 1990.

Sacchi et al., "Hu–ets–1 and Hu–ets–2 Genes are Transposed in Acute Leukemias with (4;11) and (8;21) Translocations", *Science* 231: 379–382 1986.

Saito et al., "Activation of the C–MYC Gene by Translocation: A Model for Translational Control", *Proc. Natl. Acad. Sci. USA* 80: 7476–7480 1983.

Savage et al., "Mapping Studies and Expression of Genes Located on Human Chromosome 11, Band q23", *Cytogenet. Cell Genet.* 49: 289–292 1988.

Shtivelman et al., "Fused Transcript of abl and bcr Genes in Chronic Myelogenous Leukaemia", *Nature* 315: 550–554 1985.

Siminovitch et al., "Immunoglobulin Gene Rearrangements and Expression in Diffuse Histiocytic Lymphomas Reveal Cellular Lineage, Molecular Defects, and Sites of Chromosomal Translocation", *Blood* 67: 391–397 1986.

Solomon et al., "Chromosome Aberrations and Cancer", *Science* 254: 1153–1160 1991.

Stong and Kersey, "In Vitro Culture of Leukemic Cells in t(4;11) Acute Leukemia" *Blood* 66: 439–443 1985.

Tkachuk et al., "Involvement of a Homolog of Drosophila Trithorax by 11q23 Chromosomal Translocations in Acute Leukemias", *Cell* 71: 691–700 1992.

Tsujimoto et al., "Molecular Cloning of the Chromosomal Breakpoint of B-Cell Lymphomas and Leukemias with the t(11;14) Chromosome Translocation", *Science* 224: 1403–1406 1984.

Tsujimoto et al., "Cloning of the Chromosome Breakpoint of Neoplastic B Cells with the t(14;18) Chromosome Translocation", *Science* 226: 1097–1099 1984.

van Den Elsen et al., "Exon/Intron Organization of the Genes Coding for the δ Chains of the Human and Murine T-Cell Receptor/T3 Complex", *Proc. Natl. Acad. Sci. USA* 83: 2944–2948 1986.

von Lindern et al., "The (6;9) Chromosome Translocation, Associated with a Specific Subtype of Acute Nonlymphocytic Leukemia, Leads to Aberrant Transcription of a Target Gene on 9q34", *Mol. Cell. Biol.* 10: 4016–4026 1990.

von Lindern et al., "The Translocation (6;9), Associated with a Specific Subtype of Acute Myeloid Leukemia, Results in the Fusion of Two Genes, dek and can, and the Expression of a Chimeric, Leukemia-Specific dek-can mRNA", *Mol. Cell. Biol.* 12: 1687–1697 1992.

Watson et al., "The ets Sequence from the Transforming Gene of Avian Erythroblastosis Virus, E26, has Unique Domains on Human Chromosomes 11 and 21: Both Loci are Transcriptionally Active", *Proc. Natl. Acad. Sci. USA* 82: 7294–7298 1985.

Watson et al., "Mammalian ets–1 and ets–2 Genes Encode Highly Conserved Proteins", *Proc. Natl. Acad. Sci. USA* 85: 7862–7866 1988.

Wei et al., "Physical Mapping of the Human Chromosome 11q23 Region Containing the Ataxia-Telangiectasia Locus", *Cancer Genet. Cytogenet.* 46: 1–8 1990.

Yunis et al., "Gene Order, Amplification, and Rearrangement of Chromosome Band 11q23 in Hematologic Malignancies", *Genomics* 5: 84–89 1989.

```
ALL-1   1369  RVVCFLCASSGHVEFVYCQVCCEPFHKFCLEEN.....ERPLED..........
              |.::||||:|.|    ..::|..||||||.:|.:::::      .:||
D.TRX   1266  RALCFLCGSTGLDPLIFCACCCEPYHQYCVQDEYNLKHGSFEDTTLMGSL

..............QLENWCCRRCKFCHVCGRQHQATKQLLECNKCRN
                            ||..:  .:.|..||    .:.|.:||..
              LETTVNASTGPSSSLNQLTQRLNWLCPRCTVCYTCNMSSGSKVKCQKCQK

SYHPECLGPNYPTKPTKKKKVWICTKCVRCKSCGSTTPGKGWDAQWSHDF
              .||..|||   ..:    .::||..|..|.||:.||||:|..:|
              NYHSTCLGT..SKRLLGADRPLICVNCLKCKSCSTTKVSK......FVGNL

SLCHDCAKLFAKGNFCPLCDKCYDDDDYESKMMQCGKCDRWVHSKCENLS
              .:|  :|  ||   ||||||:|:: :||||||:|.|.:.||||||:.||
              PMCTGCFKLRKKGNFCPICQRCYDDNDFDLKMMECGDCGQWVHSKCEGLS

GTEDEMYEILSNLPESVAYTCVNCTERH  1569
              ||  ||.||||.|||::.|.|.|.|.|:
              ...DEQYNLLSTLPESIEFICKKCARRN  1483
```

```
ALL-1  1810  DNRQCALCLTYGDDSANDAGRLLLYIGQNEWTHVNCALWSAEVFEDDDGSL
              |.|.  :|  .|::    :::||||||.|::.|.||||||||||.||||
D.TRX  1733  DTRMCLFCRKSGEGLSGEEARLLYCGHDCWHTNCAMWSAEVFEEIDGSL

KNVHMAVIRGKQLRCEFCQKPGATVGCCLTSCTSNYHFMCSRAKNCVFLD
             .|||  ||.||  ::|...|.||||||||::.|...:||.|.:|.|.
             QNVHSAVARGRMIKCTVCGNRGATVGCNVRSCGEHYHYPCARSIDCAFLT

DKKVYCQRH  1918
             ||.:||..|
             DKSMYCPAH  1841
```

```
ALL-1   3696  EPPLNPHGSARAEVHLRKSAFDMNFLASKHRQPPEYNPNDEEEVQLK
              |.|:|:::||.|.:|.:|||.:|||::||..:                
D.TRX   3550  ELEENAYDCARCEPYSNRSEYDMFSWLASRHRKQPIQVFVQPSDNEL...

SARRATSMDLPMPMRFRHLKKTSKEAVGVYRSPIHGRGLFCKRNIDAGEM
              :|::.:|||:|||:|:|||.|:|.|||||:|||||||||||:|:|||||
              VPRRGTGSNLPMAMKYRTLKETYKDYVGVFRSHIHGRGLYCTKDIEAGEM

VIEYAGNVIRSIQTDKREKYYDSKGIGCYMFRIDDSEVVDATMHGNAARF
              ||||||:||||:|||||:|||:|:||||||||||:|:|||||||:|||||
              VIEYAGELIRSTLTDKRERYYDSRGIGCYMFKIDDNLVVDATMRGNAARF

INHSCEPNCYSRVINIDGQKHIVIFAMRKIYRGEELTYDYKFPIEDASNK
              |||.|||||||:|:|.|||:|||||:|||||||||||||||||||:.  :|
              INHCCEPNCYSKVVDILGHKHIIIFAVRRIVQGEELTYDYKFPFED..EK

LPCNCGAKKCRKFLN 3910
              :|..||.|:|:|||||
              IPCSCGSKRCRKYLN 3759
```

ALL-1 POLYNUCLEOTIDES FOR LEUKEMIA DETECTION AND TREATMENT

CROSS REFERENCE TO RELATED PATENT APPLICATIONS

This application is a File Wrapper continuation of Ser. No. 07/971,094, filed Oct. 30, 1992, abandoned, which is a continuation-in-part of Ser. No. 888,839, filed May 27, 1992, abandoned, which is continuation-in-part of Ser. No. 805,093, filed Dec. 11, 1991, abandoned.

ACKNOWLEDGEMENT OF GOVERNMENT RIGHTS

Research for this invention was supported in part by an OGI grant CA39860 from the National Cancer Institute. The United States Government may have certain rights in this invention.

FIELD OF THE INVENTION

The present invention relates to the field of methods for diagnosis and treatment of human leukemias wherein hematopoietic cells of patients have translocations in a small region of chromosome 11 designated as ALL-1. Diagnostics and therapeutics are based on nucleic acid and amino acid sequences provided.

BACKGROUND OF THE INVENTION

Specific reciprocal chromosome translocations are very frequently found in human lymphomas and leukemias. These chromosomal abnormalities alter normal cellular genes leading to their deregulation. Chromosome translocations have been shown to play an important role in the pathogenesis of human leukemias and lymphomas by either activating cellular protooncogenes or by leading to the formation of chimeric genes capable of transforming hematopoietic cells. Erikson et al., Proc. Natl. Acad. Sci. U.S.A. 1983, 80, 519–523; Tsujimoto et al., Science 1984, 226, 1097–1099; Tsujimoto et al., Science 1984, 224, 1403–1406; Shtivelman et al., Nature 1985, 315, 35–354; Mellentin et al., Science 1989, 246, 379–382.

Translocations can lead to gene fusion resulting in a chimeric oncoprotein whose transforming activity is derived from both genes. The prototype of such events is the t(9;22) of chronic myelogenous leukemia (CML) which leads to a BCR-ABL fusion mRNA and protein (Shtivelman, supra). Translocations t(1;19), t(15;17), and t(6;9) are other examples of gene fusions, involving in the first two cases transcription factors (Nourse et al., Cell 1990, 60, 535–545; Kamps et al., Cell 1990, 60, 547–555; Kakizuka et al., Cell 1991, 66, 663–674; de The et al., Cell 1991, 66, 675–684; von Lindern et al., Mol. Cell. Biol. 1990, 10, 4016–4026).

The alternative molecular consequence of translocations is deregulation of protooncogenes by their juxtapositioning to an enhancer or promoter which is active in the type of cell from which the tumor arises. The immunoglobulin (Ig) and T cell receptor (TCR) enhancers participate in at least 15 different translocations associated with Burkitt lymphoma, chronic lymphocytic leukemia, follicular lymphoma, mantle cell lymphoma, and acute T or B cell leukemia. (Croce, CM, Cell 1987, 49, 155–156; Rabbitts, TH, Cell 1991, 67, 641–644; Solomon et al., Science 1991, 254, 1153–1160).

Chromosomal region 11q23 has been shown to be involved in different chromosomal translocations in human acute leukemias of different hematopoietic lineages. 11q23 chromosome abnormalities have been reported in acute lymphoblastic leukemia and in acute nonlymphoblastic leukemia (ANLL), most commonly of the M4 and M5A subtypes. Heim and Mitelman, Cancer Cytogenetics, Alan R. Liss, New York 1987. Chromosome 11 band q23 is frequently rearranged in acute lymphocytic (ALL), in acute myelomonocytic (AMMOL), acute monocytic (AMOL) and acute myeloid (AML) leukemias, mostly in reciprocal exchanges with various translocation partners. The t(4;11) (q21;q23), t(11;19) (q23;p13), and t(1;11)(p32;q23) are found in 10%, 2% and <1% of ALL, respectively. Reciprocal translocation between 11q23 and chromosomal regions 9p22, 6q27, 1p21, 2p21, 10p11, 17q25 and 19p13 are found in 5–6% of AML. Heim and Mitelman, supra. In addition, interstitial deletions in 11q23 have been detected both in ALL and AML.

The same segment on chromosome 11 is apparently involved in the t(11;19)(q23;p13) and t(1;11)(p32;q23) translocations in ALL as well as in translocations with the chromosomal regions 9p21, 2p21 6q27, 17q25 and 19p13 associated with 5–6% of acute myelogenous leukemias (AML). Heim and Mitelman, Cancer Cytogenetics, Alan R. Liss, New York 1987. Reciprocal translocations between chromosome region 11q23 and chromosomal regions 9p22, 6q27, 1p21, 2p21, 10p11, 17p25 and 19p13 are found in 5–6% of ANLL.

In clinical terms, rearrangements of 11q23, in particular the t(4;11) chromosome translocation, have some distinct features. The patients are often quite young; t(4;11) accounts for the vast majority of cytogenetically abnormal ALLs in infants. In the majority of patients, the leukemic cells show both B-cell and myeloid marker (Stong et al. Blood 1986, 67, 391–397) and the disease is consequently considered "biphenotypic."

Among children, most patients with the t(4;11) abnormality are less than one year of age and have a poor prognosis. The leukemic cells have a CD10–/CD19+ early B cell precursor phenotype and most of them express a myeloid associated antigen (CD15); Pui et al., Blood 1991, 77, 440–447. Myelomonocytic and biphenotypic leukemias carrying the t(4;11) aberration have also been reported; Nagasaka et al., Blood 1983, 61, 1174–1181.

There remains an unmet need for identification of the breakpoint cluster region and the genes involved in chromosome 11 aberrations associated with acute leukemias in order to provide diagnostics and therapeutics for these diseases.

SUMMARY OF THE INVENTION

The cDNA sequence of the ALL-1 gene on chromosome 11 is provided. A partial sequence of the AF-4 gene is also provided in the context of the sequences of two reciprocal endproducts of a translocation. Amino acid sequences corresponding to the cDNA sequences of the entire ALL-1 gene and the partial sequence of the AF-4 gene are also provided. Probes are provided for detecting chromosome abnormalities involving the ALL-1 gene on chromosome 11. Monoclonal antibodies for diagnosis and treatment and antisense oligonucleotides for treatment of acute leukemias are also described.

DESCRIPTION OF THE DRAWINGS

Figure 8A:
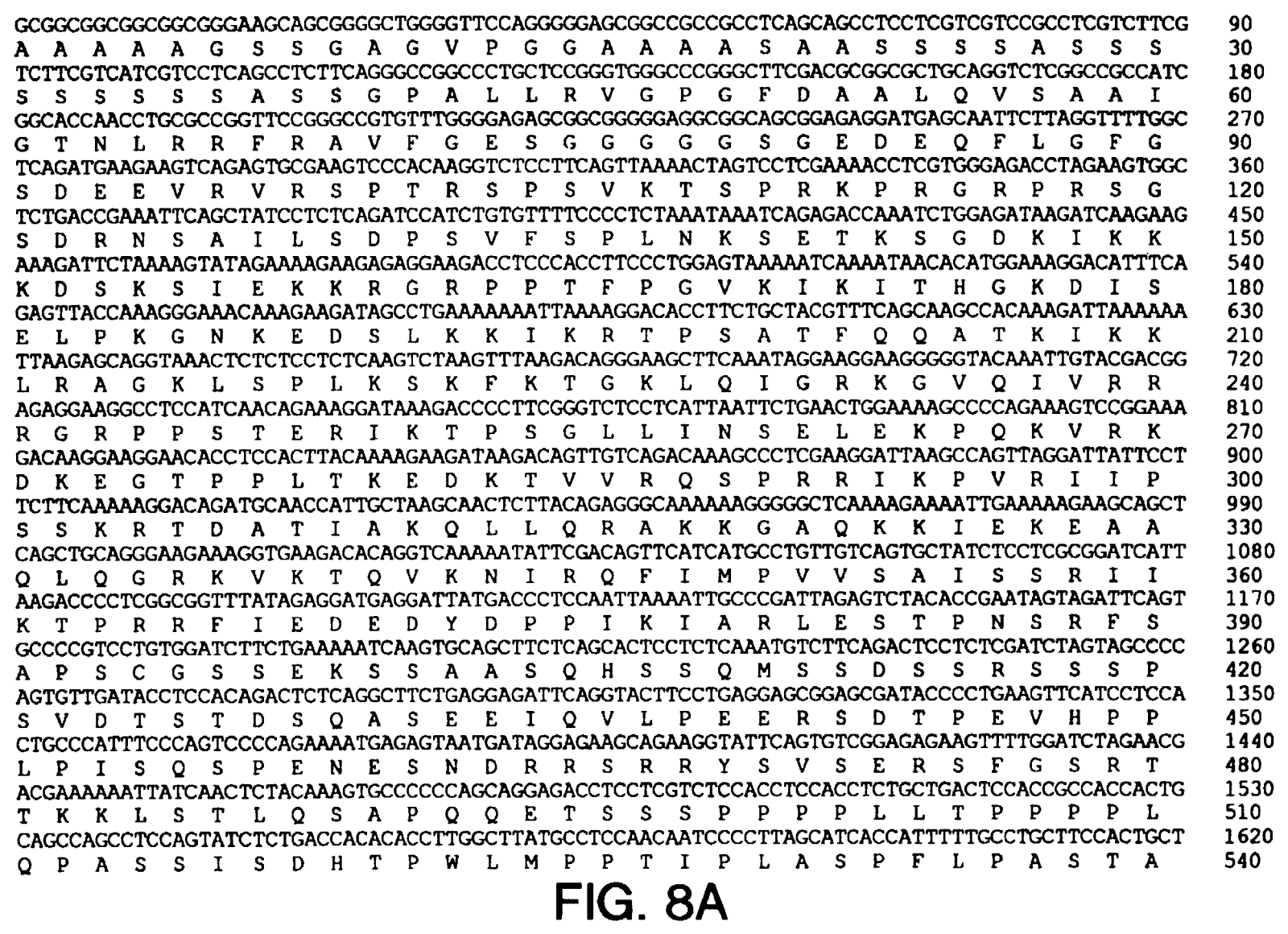
Figure 8B:
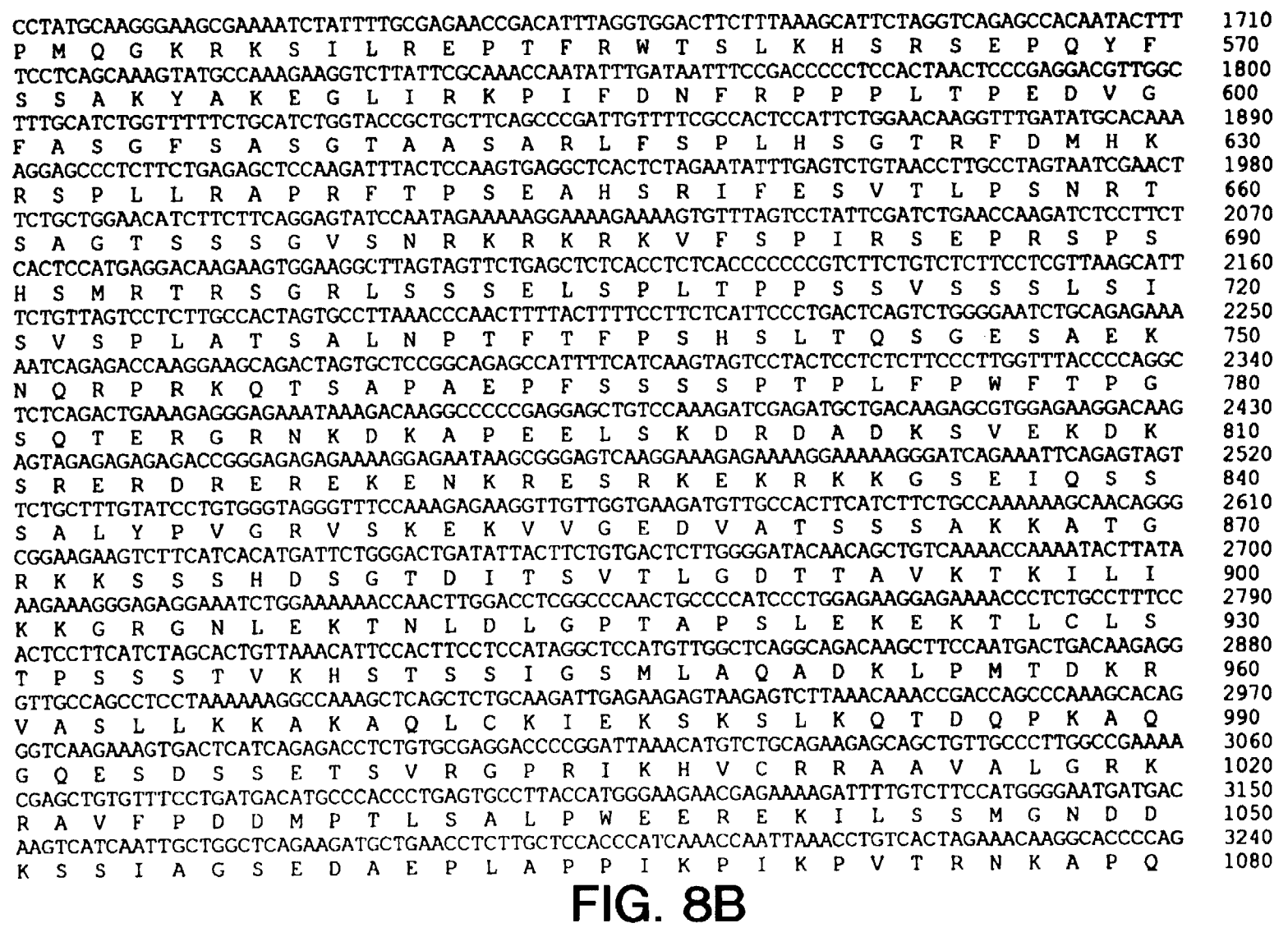
Figure 8C:
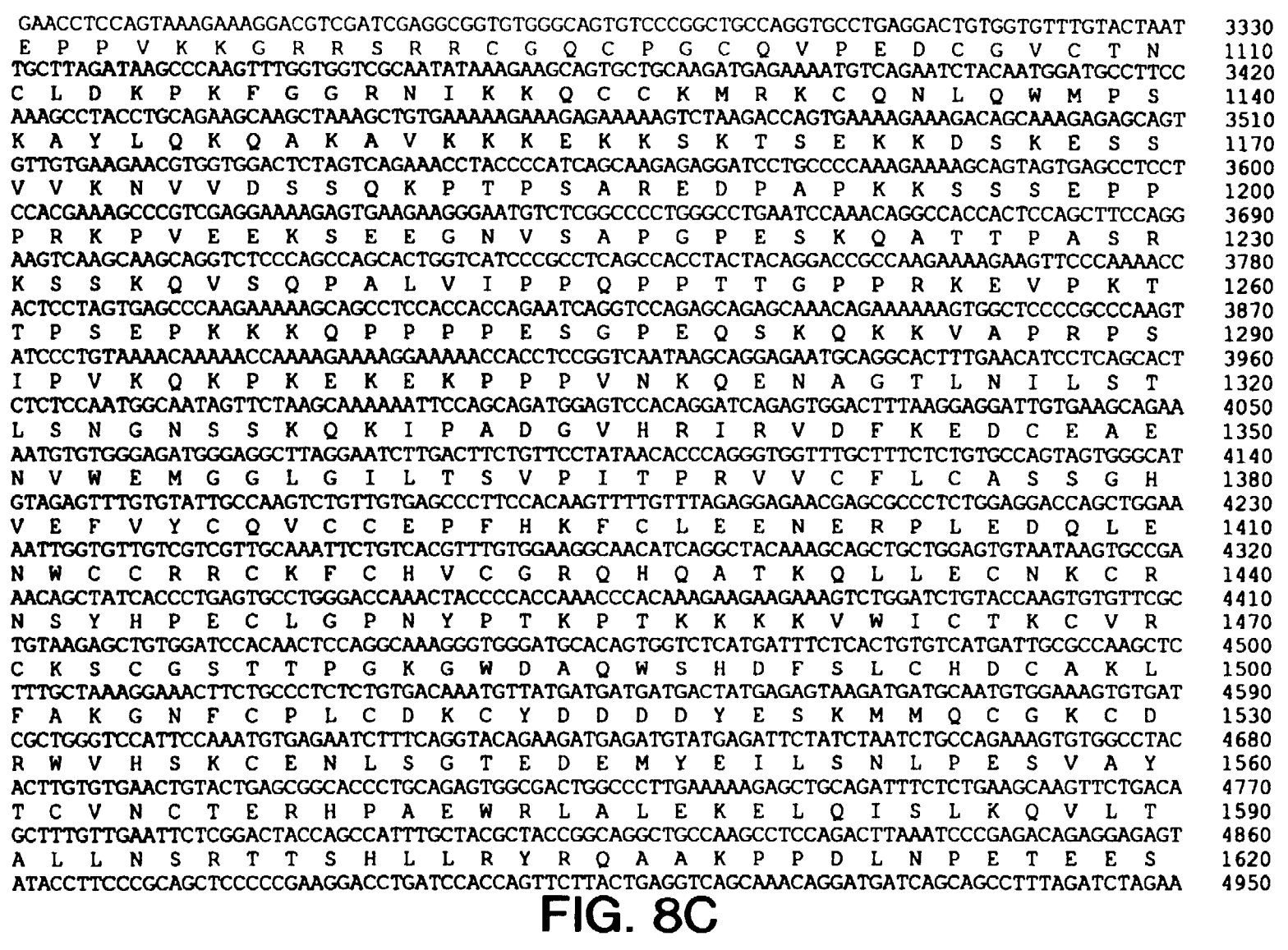
Figure 8D:
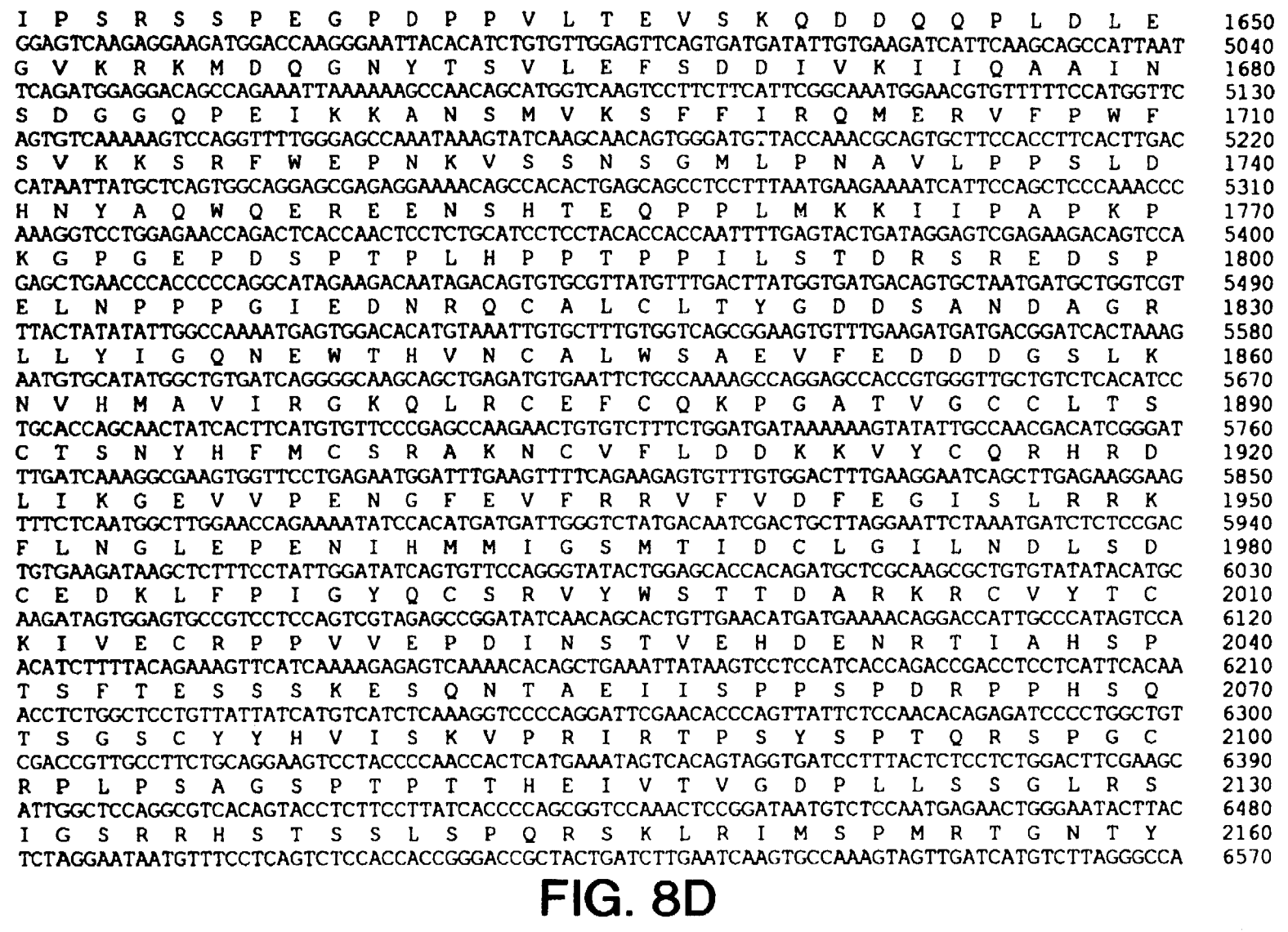
Figure 8E:
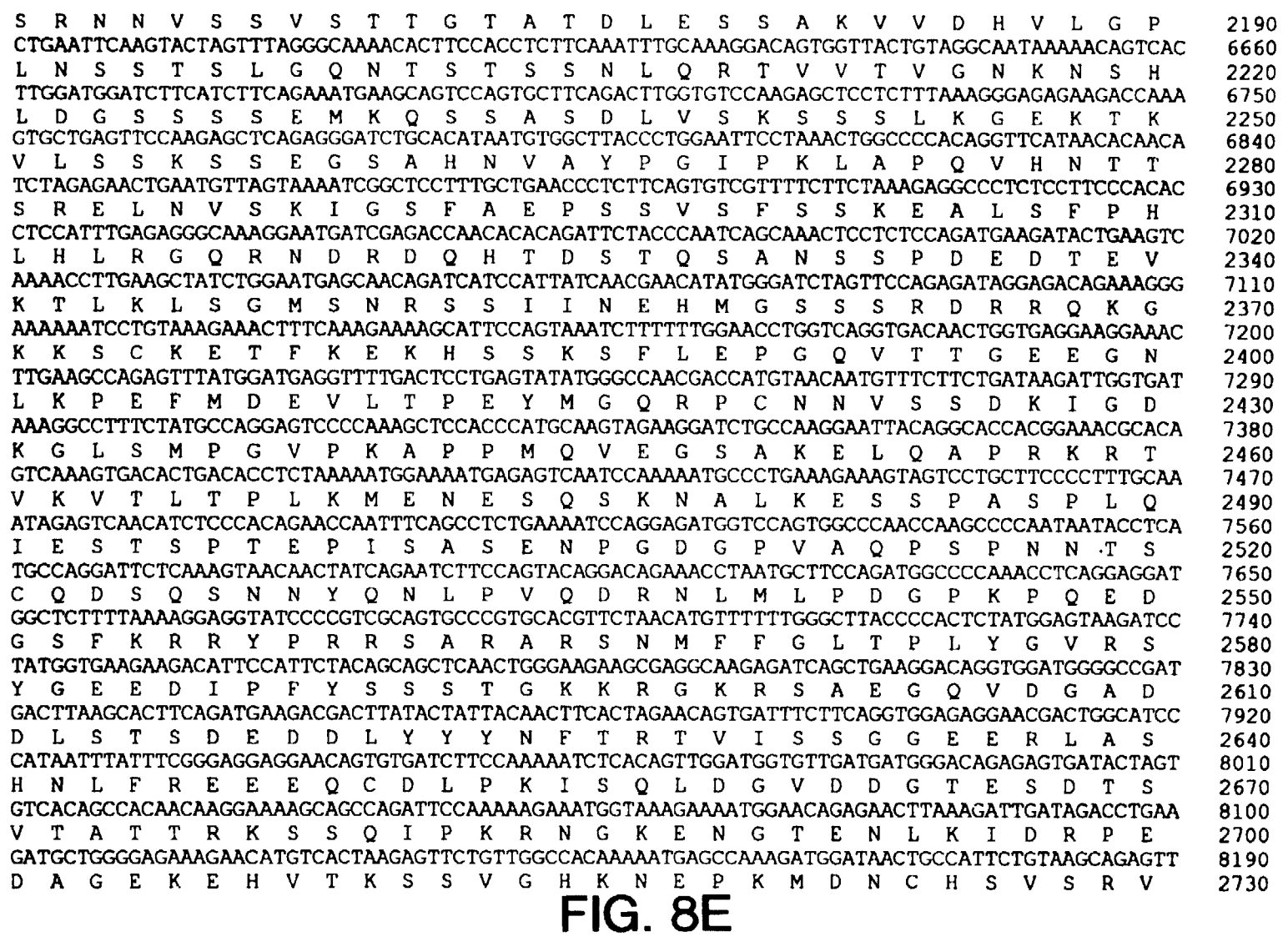
Figure 8F:
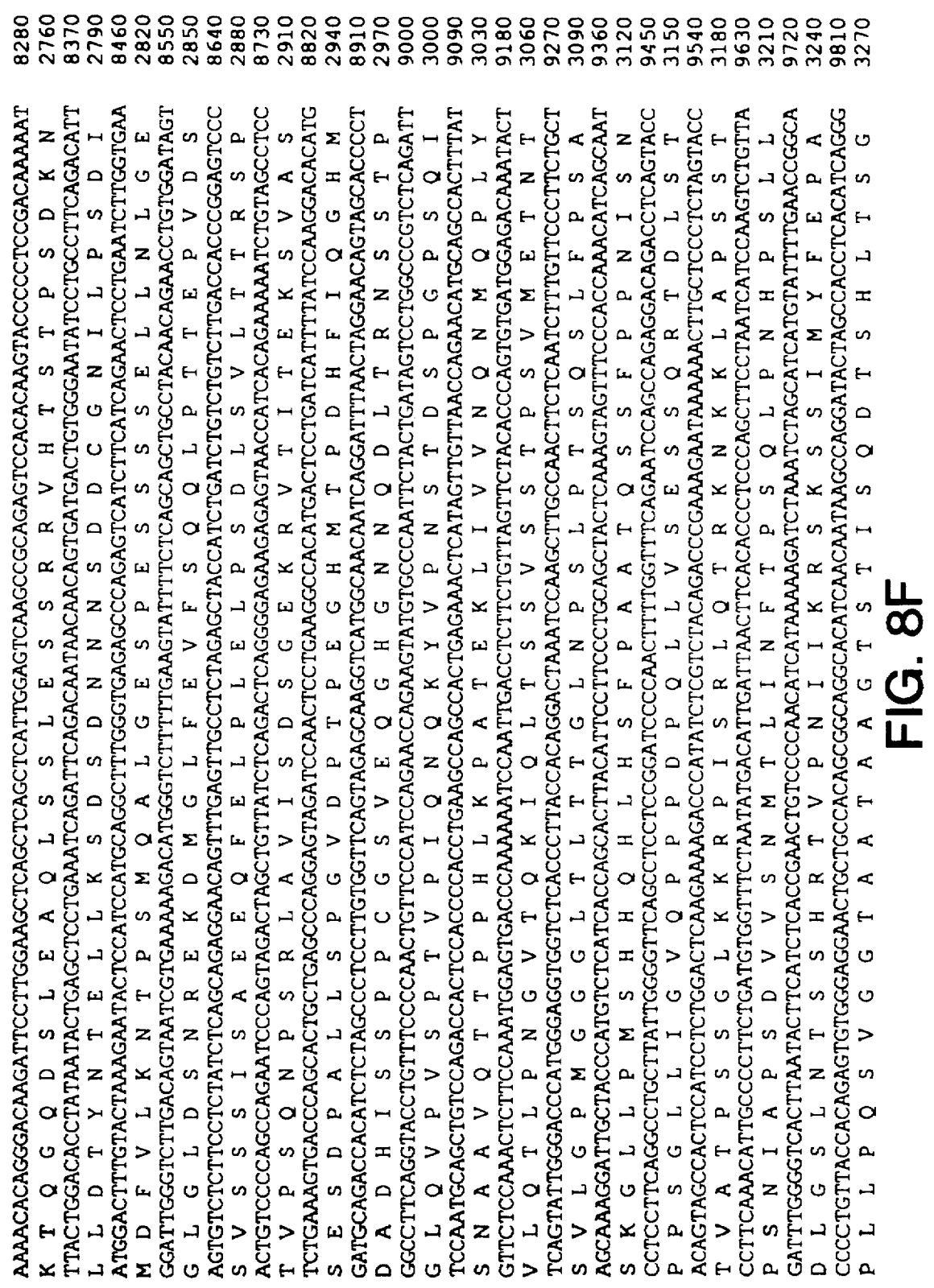
Figure 8G:
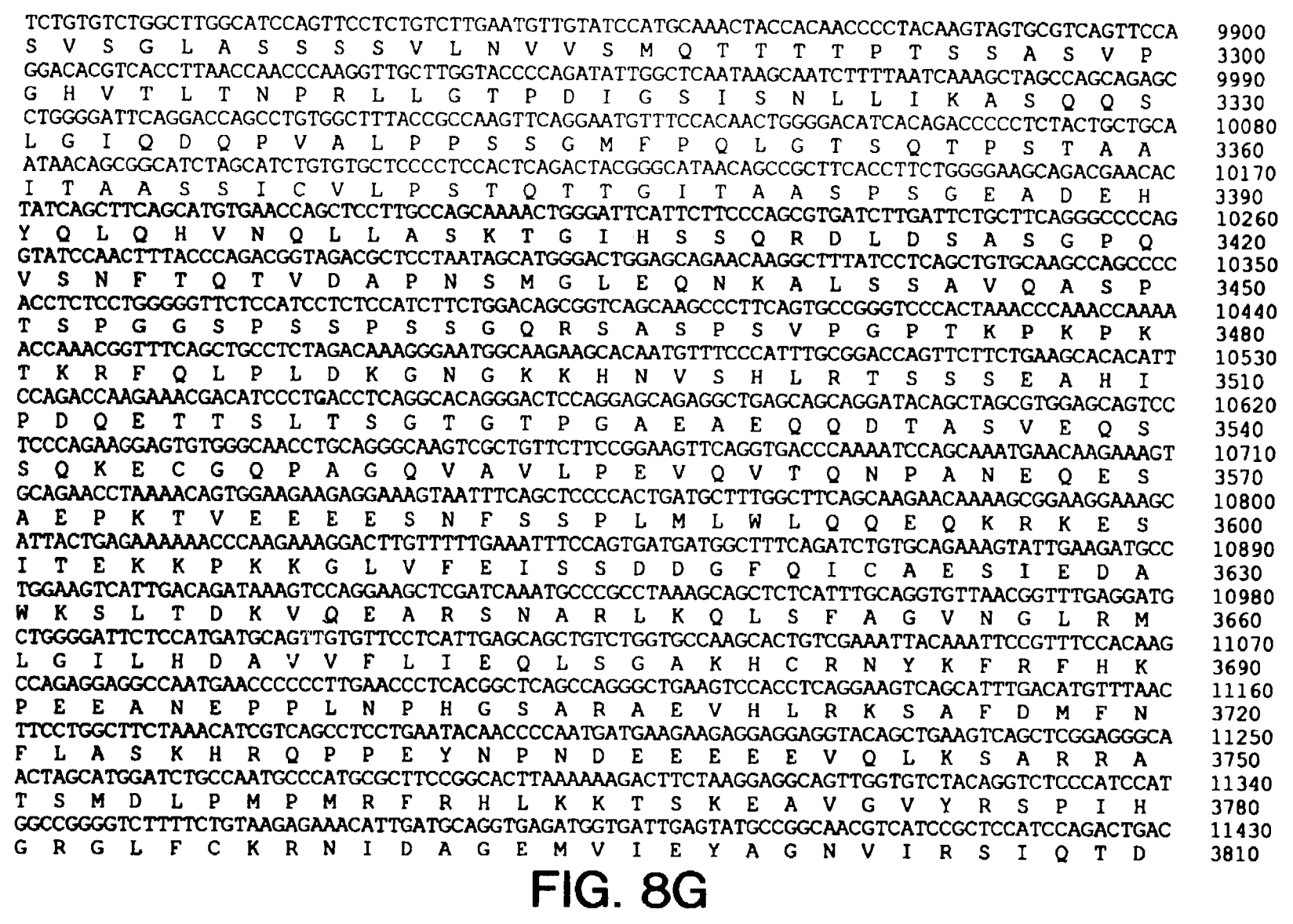
Figure 8H:
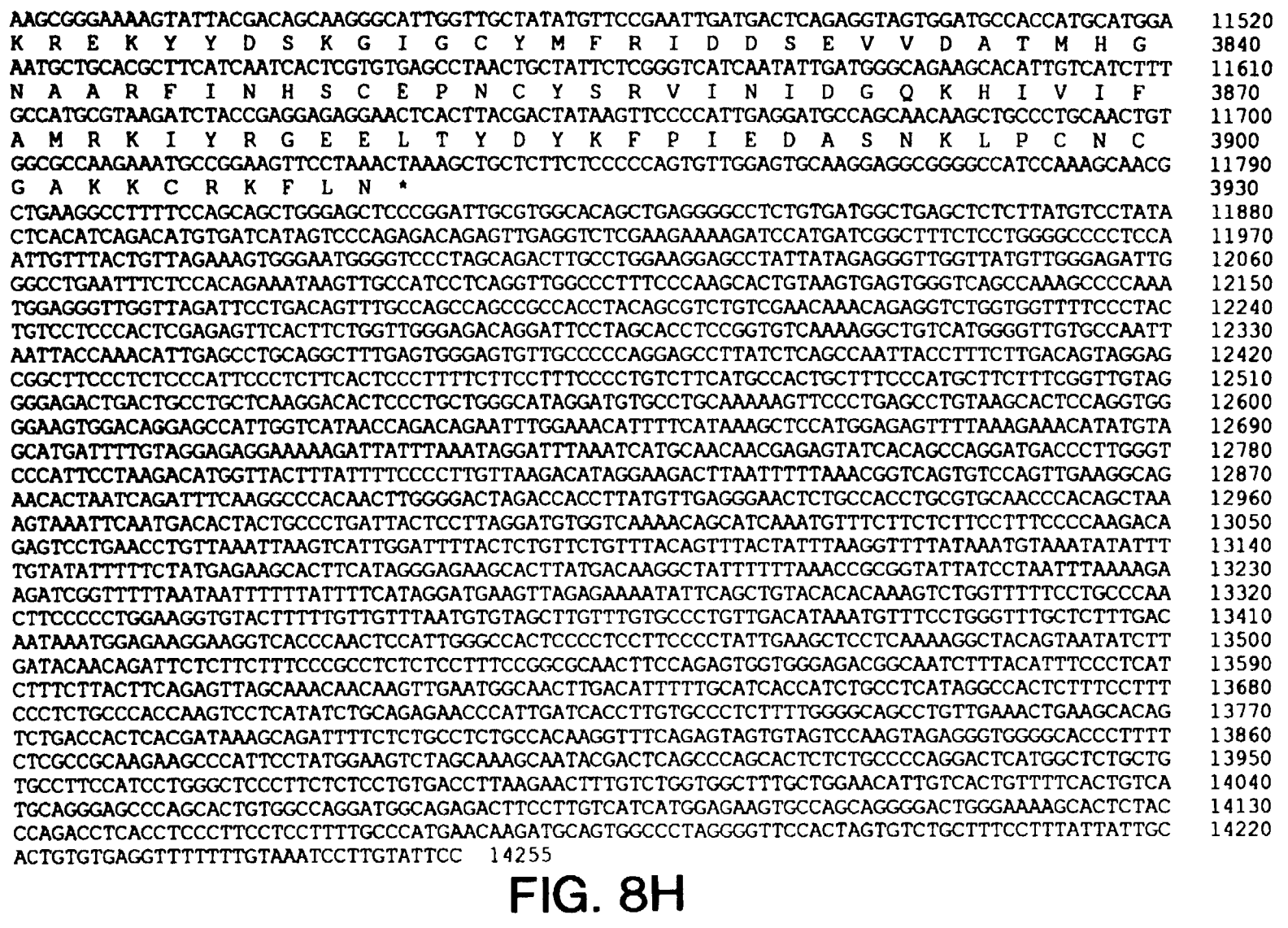

FIG. 8A–H shows nucleotide sequence and predicted amino acid sequence of ALL-1 cDNA.

FIG. 9A–D depicts homology between ALL-1 and Drosophila trithorax (D. Trx) proteins (top and center), and the structure of ALL-1 zinc finger-like domains (bottom). Bars indicate identical residues. One dot and two dots indicate first and second degree conservative differences, respectively.

DETAILED DESCRIPTION OF THE INVENTION

The ALL-1 gene located at human chromosome 11 band q23 is rearranged in acute leukemias with interstitial deletions or reciprocal translocations between this region and chromosomes 1, 2, 4, 6, 9, 10, 15, 17 or 19. The gens spans approximately 100 kb of DNA and contains at least 21 exons. It encodes a protein of approximately 4,000 amino acids containing three regions with homology to sequences within the Drosophila trithorax gens including cysteine-rich regions which can be folded into six zinc finger-like domains. The breakpoint cluster region within ALL-1 spans approximately 8 kb anti encompasses several small exons (including exons 6–12), most of which begin in the same phase of the open reading frame.

The t(4;11) chromosome translocation results in two reciprocal fusion products coding for chimeric proteins derived from ALL-1 and from a gens on chromosome 4. This gens on. chromosome 4 is termed "AF-4" while the chimeric gens resulting from the t(4;11) translocation is termed "ALL-1/AF-4." Therefore, it is believed that each 11q23 abnormality gives rise to a specific oncogenic fusion protein.

A DNA fragment which detects DNA rearrangements by Southern analysis in the majority of patients with t(4;11), t(9;11) and t(11;19) chromosomal aberrations has been cloned from chromosome 11. This locus is referred to as ALL-1 for acute lymphocytic leukemia, although the same locus is also involved in acute myelomonocytic, myelogenous and monocytic leukemias carrying translocations involving 11q23.

Figure 1:
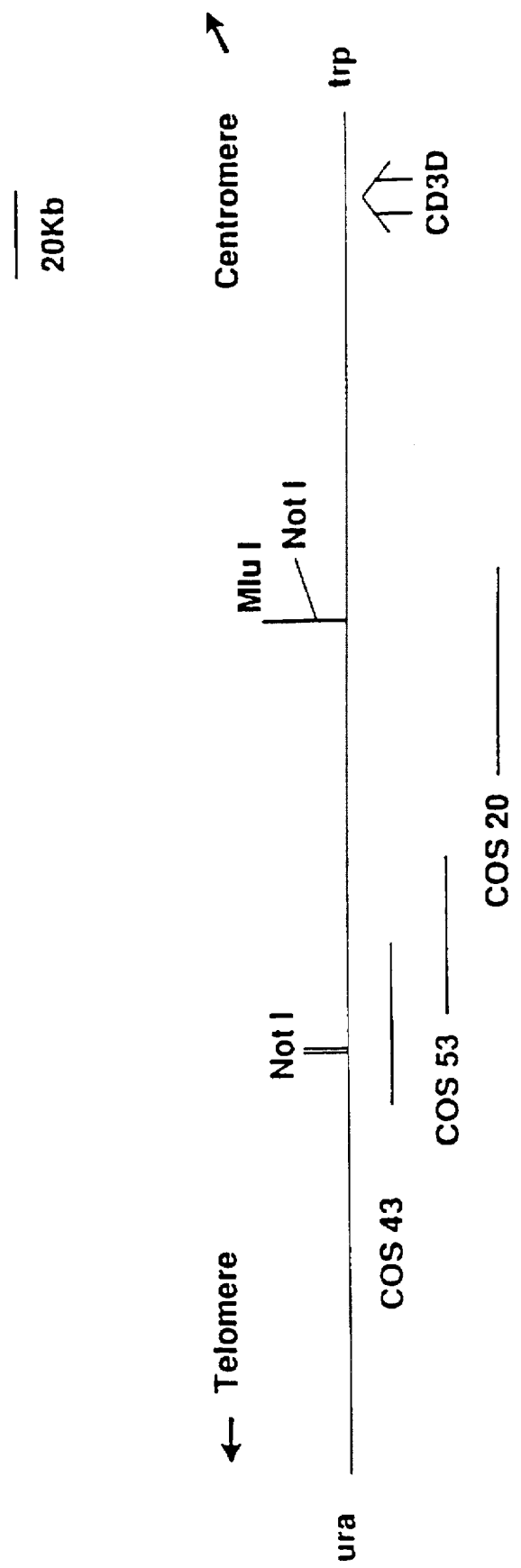
FIG. 1 is a drawing depicting a physical map of YAC B22B, which has been described in Rowley et al., Proc. Natl. Acad. Sci. U.S.A. 1990, 87, 9358–9362. ura and trp correspond to the termini of the vector. A 40 kb segment located towards the ura end and lacking NotI and MluI sites is not included in the map. Pulse field analysis indicates two or three SfiI sites located to the left of cosmid 43.

DNAs and RNAs were extracted from cell lines primary tumors by conventional methods. Southern and Northern analysis were performed as described in Shtivelman et al. *Nature* 1985, 315, 550–554). To obtain unique (repeat free) probes, cosmids were digested with a variety of restriction enzymes, and analyzed by Southern blotting for fragments which do not react with radiolabeled total human DNA. End fragments of cosmids were identified by hybridizing cosmids' digests to radiolabeled oligonucleotides corresponding to the recognition sequences for T7 and T3 RNA polymerases. If the end fragments contained human repeats, they were isolated, digested with frequent cutters and analyzed as described above. The 0.7 kb DdeI probe was thus obtained from a terminal 3.5 kb EcoRV fragment of cosmid 53. A portion of the Washington University's human DNA-containing YAC library (Green et al., *Proc. Natl. Acad. Sci. U.S.A.* 1990, 87, 9358–9362) was screened for CD3 DNA sequences (van Den Elsen et al., *Proc. Natl. Acad. Sci. U.S.A.* 1986, 83, 2944–2948) by a polymerase chain reaction (PCR)-based screening protocol (Green et al., *supra*). The YAC clone obtained appeared to be identical to the one described by Rowley et al., *Proc. Natl. Acad. Sci. U.S.A.* 1990, 87, 9358–9362, and spanned the translocation breakpoint in a t(4;11) cell line as evidenced by hybridization analysis. By pulse field electrophoretic analysis, the size of the insert was estimated as 350 kb. A 310 kb version of the insert, generated by spontaneous deletion at the left (telomeric) side, predominated in the population of DNA molecules and was mapped (FIG. 1).

To obtain specific segments of the insert, the YAC was purified by pulse field electrophoresis and shotgun cloned into the Supercos (Stratagene) cosmid vector. For this purpose the insert was partially digested by a combined application of dam methylase and the restriction endonuclease MboI, Hoheisel et al., *Nuc. Acid Res.* 1989, 17, 9571–9582. Both enzymes act on the sequence GATC, but MboI is unable to cut the methylated form. More than a hundred cosmid clones, detected with a probe for human repetitive sequences, were obtained. The cosmids were mapped by screening for those with sites for NotI and MluI enzymes, and for those hybridizing to CD3, trp and ura probes. Some cosmids were established using unique (repeat free) probes obtained from termini of cosmids. The positions of 3 cosmids mapped to the center of the YAC are shown in FIG. 1. Unique probes from these cosmids as well as from cosmids mapped to other regions of the YAC were used to screen Southern blots of DNAs from tumors exhibiting translocations.

Figure 2:
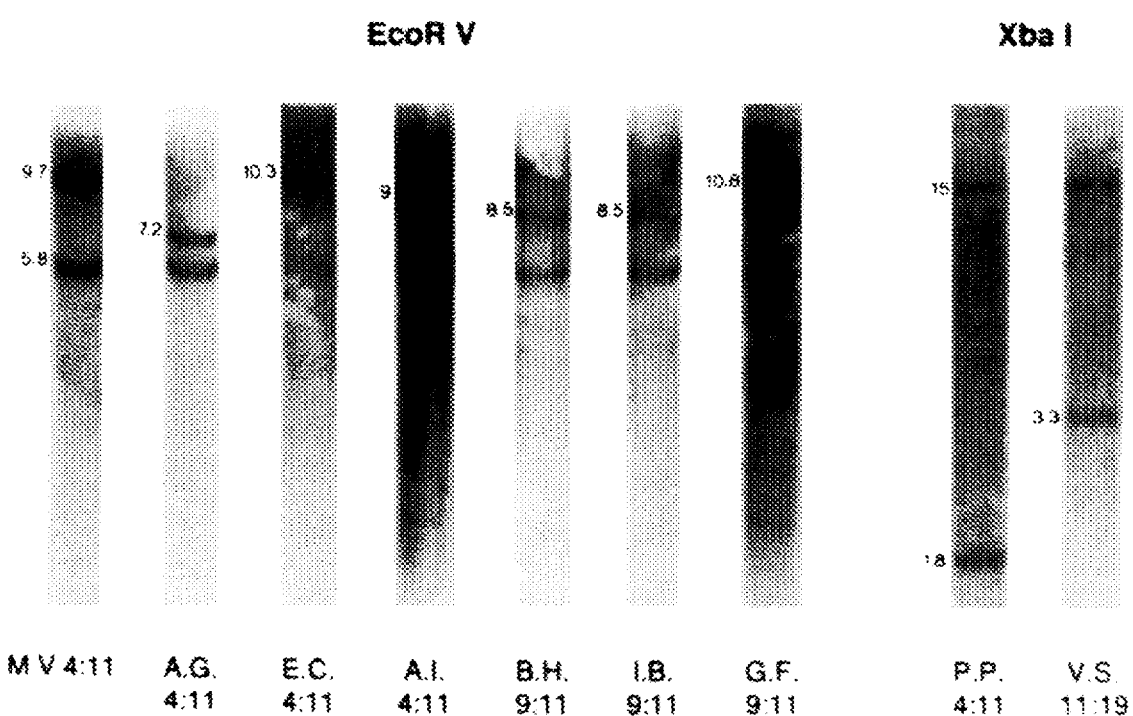
FIG. 2 is a photograph showing the results Southern blot analysis of tumor DNAs. Blots were hybridized to the radiolabeled 0.7 kb DdeI fragment derived from the terminus of cosmid 53. Aliquots of 10 µg were analyzed.
Figure 3:
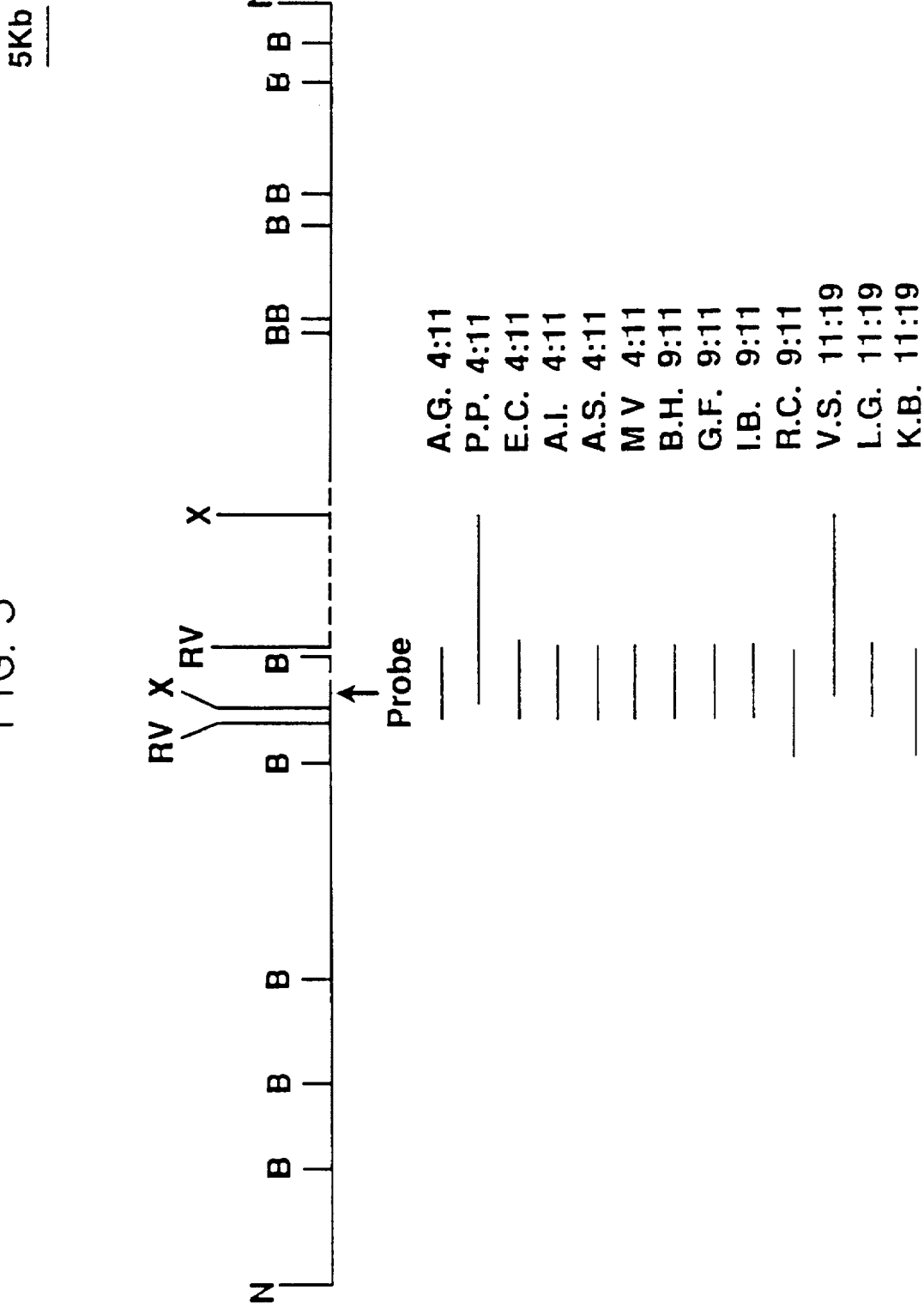
FIG. 3 is a drawing showing mapping of tumor breakpoints. The internal NotI fragment of YAC is shown in the same orientation as in FIG. 1. The dotted line represents a region not cloned in the cosmids. Restriction sites within this region are deduced from the size of the relevant germline fragments detected in genomic Southern blots using the indicated probe. Additional EcoRV and XbaI sites are not shown. Some of the samples were not analyzed with BamHI. Lines below the map correspond to the smallest genomic fragments found rearranged. N=NotI; B=BamHI; RV=EcoRV; X=XbaI. The breakpoint cluster region is believed to span approximately the region encompassed by the two nearest BamHI sites flanking the arrow; more specifically, the breakpoint cluster region is believed to span exons 6–12 illustrated in FIG. 10.

A 0.7 kb DdeI fragment derived from the terminus of cosmid 53 detected rearranged fragments in tumor DNAs digested with EcoRV, XbaI, or BamHI. Examples of these analyses are shown in FIG. 2. The leukemic cells from patients A. G. E. C., A. L., B. H., I. B., G. F., P. P., and V. S. contained novel EcoRV or XbaI fragments of various sizes. This probe detected rearrangements in 6/7, 4/5, and 3/4 patients with the t(4;11), t(9;11) and t(11;19) translocations, respectively. Upon determination of the smallest genomic fragment in which rearrangement could be identified, (FIG. 3) it became apparent that most or all breakpoints clustered within a small DNA region of approximately 8 kb. In three other patients two rearranged fragments (as well as a germline species) were detected, probably due to the presence of the breakpoint in these patients within the 0.7 kb DdeI segment corresponding to the probe. Finally, normal fibroblast DNAs from 7 additional individuals were used for comparison to show the germline fragments after digestions with EcoRV, XbaI or BamHI.

Figure 4:
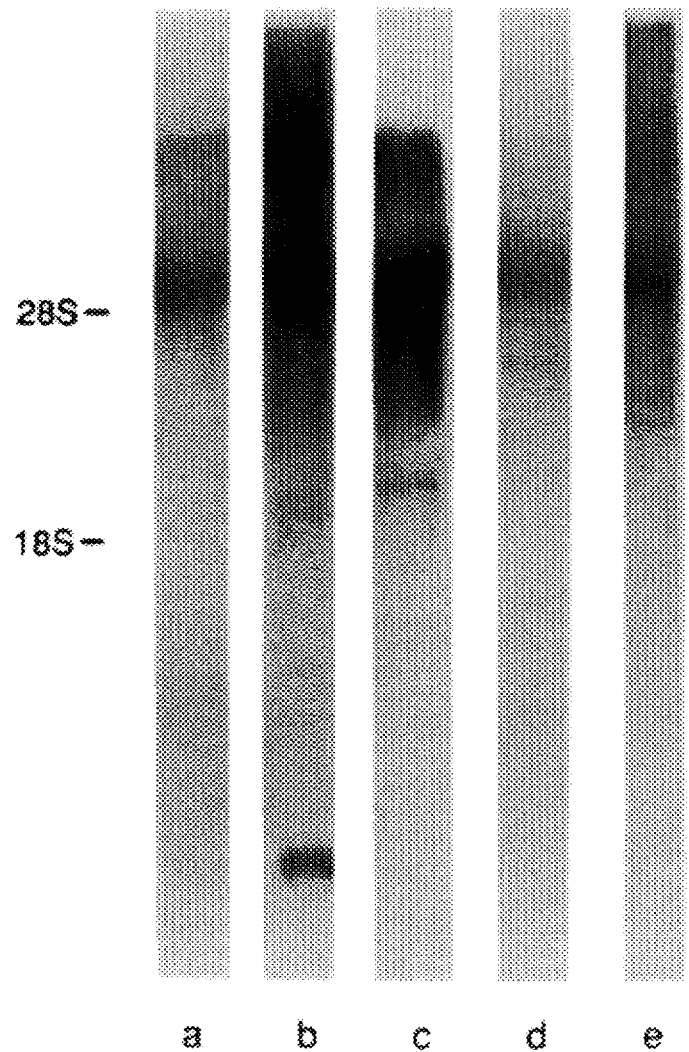
FIG. 4 is a photograph showing the results of Northern blot analysis of RNA from cell lines and a primary leukemia using pooled probes. 10–20 µg aliquots of total RNA were analyzed on a formaldehyde gel. Following hybridization, blots were washed in a solution containing 0.1% SSC and 0.1% SOS at 700. RNAs were obtained from: a) K562 cells; b) the glioblastoma T98G cell line; c) the SupB pre B ALL cell line; d) the MV4;11 cell line; and e) a patient with t(9;11).

As a first step toward identification of genes neighboring the breakpoint cluster region, pooled unique fragments from cosmid 20 were labeled, together with the terminal fragment of cosmid 53, and were used to probe RNAs from cell lines and patients with or without 11q23 translocations (FIG. 4). The pooled probe detected 5 kb and 10 kb RNA species in the K562, glioblastoma T986 and Sup B cell lines (lanes a, b, c). It also hybridized with a 5 kb RNA from patients with t(4;11), t(9;11), and t(11;19) (FIG. 4, lanes d, e,). In another patient with t(4;11) the probe detected the 10 kb RNA species alone.

It has been discovered that in leukemic cells of patients with the t(4;11), t(9;11) and t(11;19) translocations the breakpoints on chromosome 11 cluster in a small region of approximately 8 kb. Other translocations in acute leukemia affecting 11q23 are believed to map to the same locus. This locus has been designated ALL-1 for acute lymphocytic leukemia although the ALL-1 locus is also involved in translocations in acute myelomonocytic, monocytic and myelogenous leukemias. The tight clustering of breaks suggests that the gene involved is close to the breakpoints. The Northern analysis indicates that DNA sequences adjacent to the breakpoints are expressed However, no new transcript was detected in the leukemic cells. Moreover, only one of the transcripts (usually the 5 kb species) found in cells without the translocation was detected in the patients.

Figure 5:
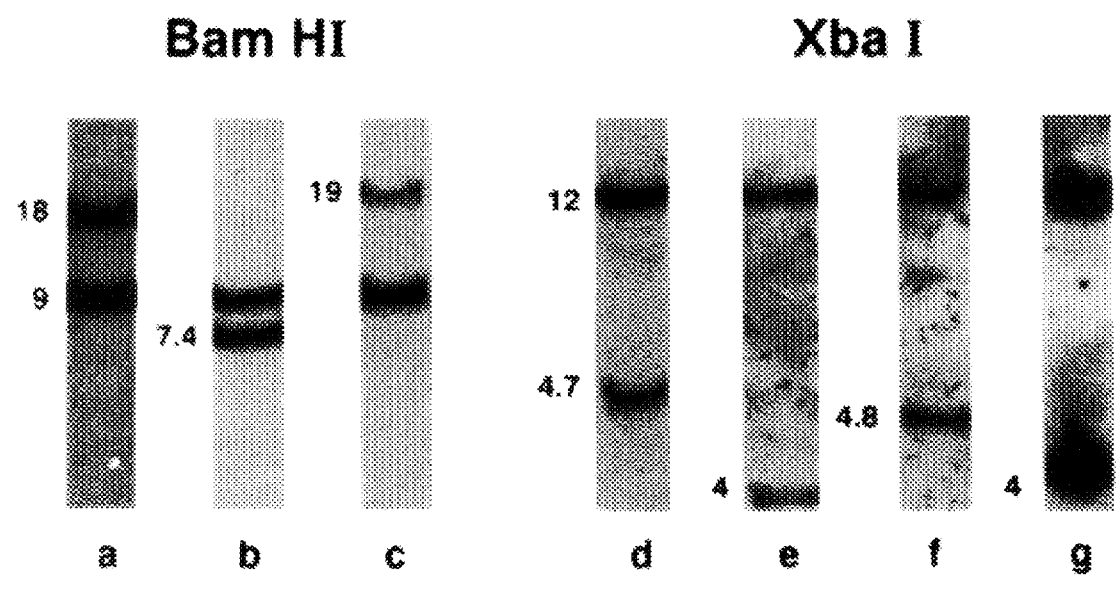
FIG. 5 is a photograph showing the results of Southern blot analysis of DNAs from primary tumors and cell lines with 11q23 abnormalities using a modified 0.5 kb DdeI probe. a) patient C. H. with t(6;11); b) the B1 cell line with t(4;11); c) the RS 4;11 cell line with t(4;11); d) patient J. B. with t(10;11); e) patient M. L. with t(1;11); f) patient S. O. with del(11) (q23); g) patient R. E. with del(11) (q23). Numbers indicate kilobases. The germline BamHI and XbaI fragments are of 9 and 12 kb, respectively.

The finding of tight clustering of the breakpoints on chromosome 11 in the three most common 11q23 abnormalities raised the possibility that the same region is rearranged in other chromosomal aberrations involving 11q23. To test this, tumor DNAs from the leukemic cells of patients with t(6;11)(q27;q23), t(1;11)(p34;q23), t(10;11) (p11–15;q23) and del (11)(q23) were digested with BamHI, XbaI, EcoRV and HindIII enzymes and subjected to Southern analysis using the modified 0.5 kb DdeI fragment as a probe. This probe was obtained from the 0.7 kb DdeI probe by digestion with AluI, which ultimately improved performance by removing a 0.24 kb internal fragment that had caused a higher background in Southern analyses. Following digestion with AluI, the internal fragment and the two end fragments were electrophoresed to isolate the two terminal fragments, which were then ligated to form a 0.5 kb fragment which was cloned into a plasmid vector. Results of Southern blotting are shown in FIG. 5. Rearranged fragments were found in the DNAs of patients with t(6;11), t(1;11) and t(10;11)(lanes a, d, e, respectively) and in two patients (lanes f, g) out of five with interstitial deletion in 11q23 (the 3 negative patients had del 11(q21;q23)). The patients with t(6;11) and t(10;11), as well as one of those with del(11)(q23) showing rearrangement had AML; the rest of the patients tested had ALL.

Figure 6:
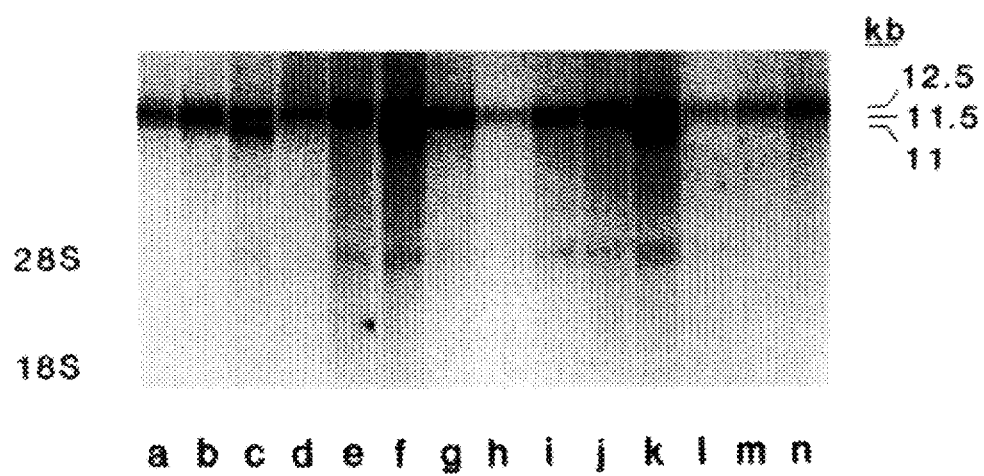
FIG. 6 is a photograph showing the results of Northern blot analysis of RNAs from cell lines using a 1.5 kb EcoRI probe generated from cosmid 20. Lanes included SK DHL (a); KCL22 (b); MV 4;11 (c); T98G (d); All-1 (e); B1 (f); K562 (g); Jurkat (h); GM607 (i); 697 (j); RS4;11 (k); GM1500 (l); LNCaPFGC (m); PC3 (n). 28S and 18S indicate migration of ribosomal RNA.

To further analyze transcription of the genomic DNA adjacent to the breakpoint cluster region, segments of cosmid 20 found fully or partially free of repetitive sequences were examined as probes to polyadenylated RNAs obtained from a variety of hematopoietic and non-hematopoietic cell lines. Three ALL cell lines, MV 4;11, RS 4;11 and B1 containing the t(4;11) chromosome translocation were included in the analysis. These three cell lines had rearrangements at the breakpoint cluster region, as shown in FIG. 5, lanes b and c. A 1.5 kb EcoRI DNA segment generated from cosmid 20 was used as a probe and identified a 12.5 kb RNA in all cell lines (FIG. 6). A minor species of 11.5 kb was detected in most of the samples without involvement of 11q23, but it was not possible to determine if this RNA was present in the cells with the t(4;11) translocation. A transcript of 11kb was detected in the three cell lines with the t(4;11) chromosome translocation (FIG. 6; lanes c, f, k). The width of this band on the autoradiogram suggests that it corresponds to two comigrating RNA species. The 11 kb RNA was not detected in any of the cell lines lacking 11q23 aberrations (FIG. 6).

These results show that the same breakpoint cluster region is rearranged in at least seven different 11q23 abnormalities, including six types of translocations, as well as interstitial deletions. Three samples with 11(q21;q23) deletions, one sample with t(11;15)(q23;q22), and one sample with t(11;X) (q23;q26) did not show rearrangements within the locus. In addition, in 1 of 12, 1 of 9, and 2 of 9 patients with t(4;11), t(9;11), and t(11;19) chromosome translocations respectively, rearrangements were not detected using the DdeI probe. Finally, the breakpoint in the RC-K8 cell line containing the t(11;14)(q23;q32) is apparently telomeric to the locus discussed here. In all of these cases, other unidentified loci on chromosome 11 could be involved. Alternatively, the ALL-1 locus might also be affected in these patients, but this may occur at a different site.

Using a new probe, three polyadenylated transcripts were identified. Two of them, a 12.5 and an 11.5 kb species are expressed as detected by Northern analysis in most or al cell lines, but the third, an 11kb RNA, was detected solely in cell lines with the t(4;11) abnormality. RNA species similar size have recently been reported by others. For example, Ziemin-van der Poel et al., *Proc. Natl. Acad. Sci. U.S.A.* 1991, 88, 10735-10739. However, while the instant probe, which is located centromeric to the breakpoints, detects all three RNAs; Ziemin-van der Poel et al. reported that their probe (#1), which is derived from the same general location, detect predominantly the 12.5 kb species. While the instant probe detects 11 kb transcript solely in leukemic cells with the t(4;11) chromosome translocation, the Ziemin-van der Poel et al. study identifies an 11 kb mRNA in the RS4;11 cell line, as well as in small amounts in all cells tested. The results show, however, a clear qualitative alteration in expression of a region adjacent to the breakpoint cluster region on chromosome 11 in cells with the t(4;11) chromosome translocation.

Using either somatic cell hybrids (Savage et al., *Cytogenet. Cell Genet.* 1988, 49, 289-292; Wei et al., *Cancer Genet. Cytogenet.* 1990, 46, 1-8; Yunis et al., *Genomics* 1989, 5, 84-90), or the fluorescent in situ hybridization (FISH) technique (Rowley et al., *Proc. Natl. Acad. Sci. U.S.A.* 1990, 87, 9358-9362), it was possible to position the breakpoints on chromosome 11 to a region between the CD3 and PBGD genes. Rowley et al., supra, used a CD3-gamma probe to clone a 350 kb human DNA fragment from a yeast artificial chromosome (YAC) library. This YAC spanned the t(4;11), t(9;11), t(11;19), and t(6;11) breakpoints as indicated by FISH analysis. Using probes derived from both sides of the breakpoint cluster region, Rowley et al. identified a 12.5 kb RNA in cells with or without 11q23 abnormalities. Further, a probe located telomeric to the cluster region detected two additional transcripts of 11.5 and 11kb in the RS 4;11 cell line, as well as in all hematopoietic and nonhematopoietic cells tested (Ziemin-van der Poel et al., *Proc. Natl. Acad. Sci. U.S.A.* 1991 88, 10735-10739).

From a YAC clone similar to the one used by Rowley et al., a DNA segment was obtained which detected rearrangements in leukemic cells from patients with the t(1;11), t(4;11) t(6;11), t(9;11), t(10;11), t(11;19) or del (11q23) chromosome abnormalities on Southern blots (Cimino et al., *Cancer Research* 1991, 51, 6712-6714; Cimino et al., *Cancer Research* 1992, 52, 3811-3813). The breakpoints clustered within a small region of approximately 8 kb termed the ALL-1 locus. Translocation junction fragments were cloned from leukemic cells with t(4;11) and showed clustering of the breakpoints in an area of 7-8 kb on chromosome 4. Sequencing analysis indicated heptamer and nonamer-like sequences, associated with rearrangements of immunoglobulin and T cell receptor genes, near the breakpoints. These sequences suggested a direct involvement of the VDJ recombinase in the 11q23 translocations.

Transcription of the genomic DNA adjacent to the breakpoint cluster region was analyzed using segments of cloned DNAs as probes. Probes from both sides of the region identified a major transcript of 15-16 kb (previously estimated as 12.5 kb) (Cimino et al., *Cancer Research* 1991, 51, 6712 -6714; Cimino et al., *Cancer Research* 1992, 52, 3811-3813) in cells with or without 11q23 abnormalities. The gene coding for these RNAs was termed ALL-1. Leukemic cells with the t(4;11) chromosome translocation contained, in addition to the normal species, shorter RNAs transcribed from the der (11) and der (4) chromosomes. These studies were extended to clone and sequence ALL-1 RNA, to further characterize the ALL-1 gene, and to identify chimeric transcripts produced in cells with the t(4;11) chromosome translocation.

Structure of the ALL-1 gene and cDNA

Utilizing a repeat-free genomic DNA segment located 10 kb centromeric to the breakpoint cluster region on chromosome 11 (Cimino et al., *Cancer Research* 1992, 52, 3811-3813), a human fibroblast cDNA library and a K562 cDNA library were screened (Chu et al., *EMBO J.* 1990, 9, 985-993; Shtivelman et al., *Nature* 1985, 315, 550-554).

Figure 7:
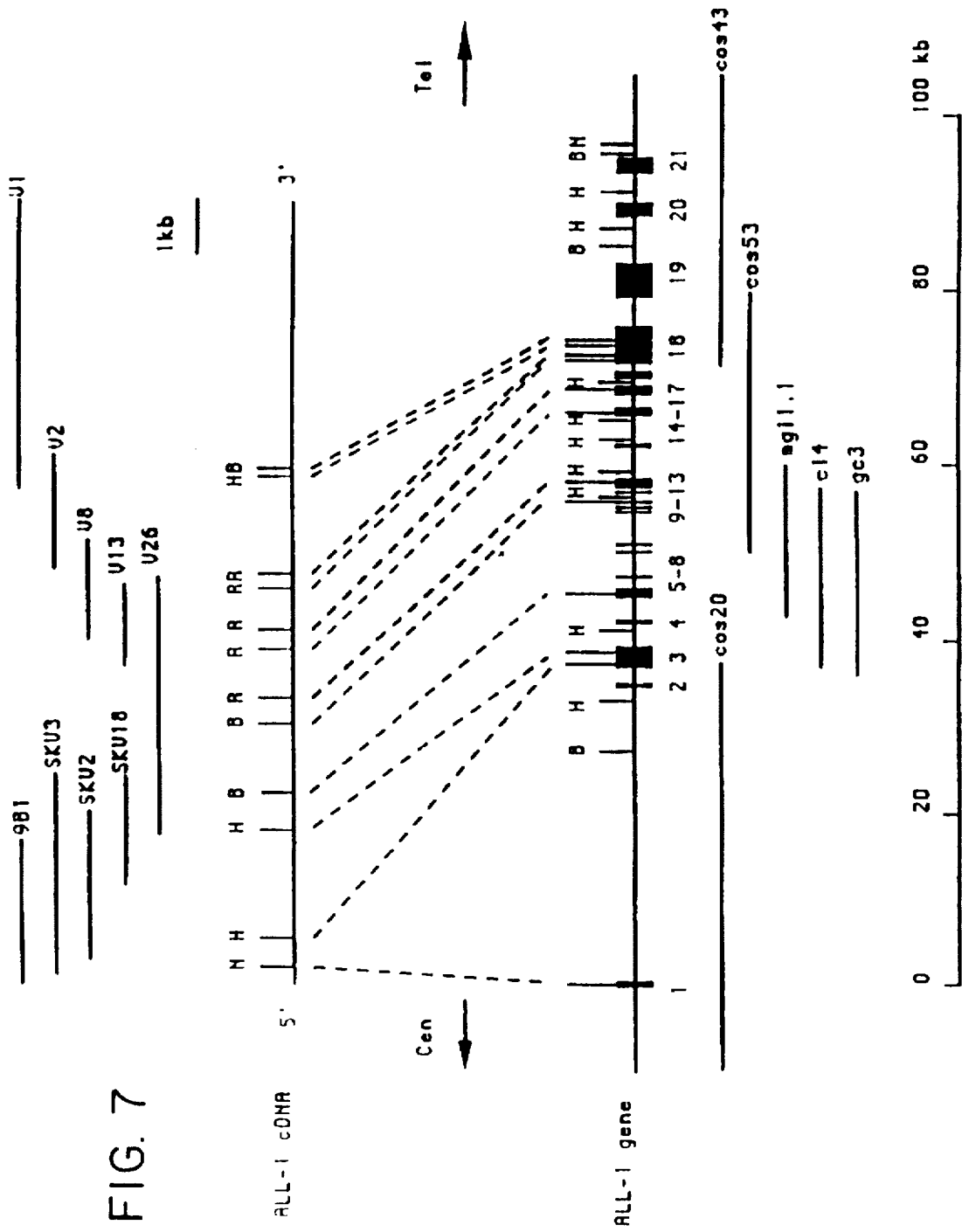
FIG. 7 shows physical maps of ALL-1 cDNA and gene. All NotI (N), HindIII (H), BamHI (B), and EcoRI (R) sites of the cDNA are shown; only some EcoRI sites are indicated within the gene and HindIII or BamHI sites within the 5' 25 kb of the first intron are not shown. Exons are depicted as rods or boxes extending above and below the line. Cen and Tel. correspond to direction of the centromere and telomere, respectively. cDNA clones SKV2, SKV3, and SKV18 were obtained from K562 cDNA library. Clones V1-V26 were obtained from a normal fibroblast cDNA library. The 9B1 clone originated from a Burkitt lymphoma cDNA library.

Positive clones were used as probes for further screening. 5-10 µg aliquots of polyadenylated RNAs were electrophoresed on 1.1% agarose gels in formaldehyde, blotted onto nitrocellulose filters and analyzed by hybridization. (Gale, RP and Canaani, *Proc. Natl. Acad. Sci. U.S.A.* 1984, 81, 5648-5652). 20 µg aliquots of high molecular weight DNA were digested with BamHI and analyzed by the Southern technique. 3' and 5' ALL-1 probes were composed of phages V1 and SKV2 sequences, respectively (FIG. 7). Non ALL-1 probes were generated from clones 16 and 25 by PCR.

A series of overlapping clones spanning 14.7 kb (FIG. 7 top) was obtained. These cDNAs presumably originated from the major ALL-1 transcript. All cDNA sequences were found to hybridize to genomic DNA within the 95 kb internal Not I fragment of the YAC B22B (Cimino et al., *Cancer Research* 1991, 51, 6712-6714). This region was previously subcloned into cosmids 20, 43, and 53 and into phages gc3, c14, and mg 11.1 (FIG. 7). The cloning of cosmids 20, 43, and 53 from YAC B22B has been described (Cimino et al., *Cancer Research* 1991, 51, 6712-6714) and clones mg 11.1, c14, and gc3 were obtained from a genomic DNA library made in the EMBL-3 vector (Stratagene).

Restriction enzyme mapping of the cDNA and genomic clones and analysis of the hybridization pattern of cDNA fragments to genomic DNA indicated that the ALL-1 gene is composed of a minimum of 21 exons, some of them (6-12) very small (shorter than 150 bp). The first intron was found to be the largest, spanning approximately 35 kb of DNA.

The nucleotide sequence of ALL-1 cDNA was determined using an automatic sequencer (ABI). The sequence revealed single long open reading frame predicting a protein of approximately 4,000 amino acids with molecular weight of approximately 400,000 Daltons (FIG. 8). To search for homologous nucleotide sequences and protein sequences the GenBank and SWISS data bases were screened by the FASTA program. Nucleotides 9353–9696 were found to be nearly identical to an anonymous sequence (EST00626) cloned from human fetal brain cDNA library (Adams et al., *Nature* 1992, 355, 632–634).

Figure 9D:
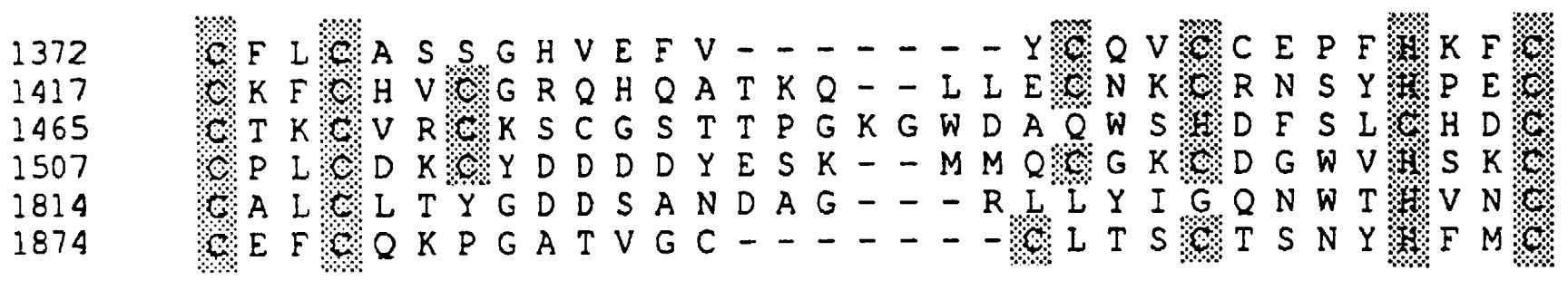

Three regions demonstrated homology to the trithorax gene of Drosophila (Mazo et al., *Proc. Natl. Acad. Sci. U.S.A.* 1990, 87, 2112–2116). Thus, predicted amino acids 1021–1221, 1462–1570, and 3348–3562 showed 64%, 66%, and 82% similarity, and 43%, 50%, and 61% identity, respectively, to the Drosophila gene (FIG. 9). The third region of homology constitutes the extreme C-terminus of the two proteins; both species end in an identical sequence. The first homology region is cysteine-rich and contains sequence motifs analogous to four zinc finger domains (3–6) within the trithorax gene (Mazo et al., *supra*). The second region of homology is also cysteine-rich and corresponds to zinc fingers 7 and 8 of the Drosophila gene. The human putative zinc finger structures are shown at the bottom of FIG. 9. The multiple conserved cysteines and histidines at the 3' end of the motifs allow two or three arrangements of the putative fingers. The structure of these cysteine-rich domains appears to be unique to the trithorax and ALL-1 genes.

Chimeric RNAs resulting from the t(4;11) chromosome translocations

Figure 10A:
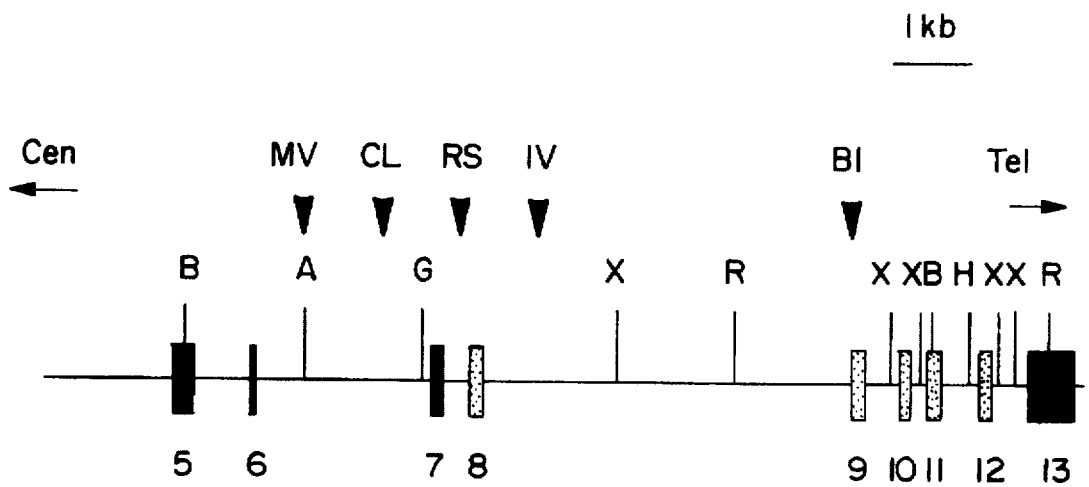
FIG. 10 shows exon-intron structure of ALL-1 breakpoint cluster region (A) and partial sequence of the two reciprocal ALL-1/AF-4 fused transcripts (B, C). In (A), exons containing the zinc finger-like domains (8–12) are represented by cross-hatched boxes. Among the five t(4;11) breakpoints shown (arrowheads in A), included are those of the MV4;11 (MV), RS4;11 (RS), and B1 (B1) cell lines. C.L. and I.V. represent leukemic cells with t(4;11) from two patients. B, R, G, X, H correspond to sites for the enzymes BamHI, EcoRI, BglII, XbaI, and HindIII, respectively. In sequences within (A), small and large letters represent introns and exons, respectively. Cytosine in position 4141 of ALL-1 sequence (FIG. 2) is replaced by thymidine in clone 25, resulting in alteration of Leucine into Phenylalanine (C).

Clustering of t(4;11) breakpoints has previously been found within a small segment of the ALL-1 locus (Cimino et al., *Cancer Research* 1991, 51, 6712–6714; Cimino et al., *Cancer Research* 1992, 52, 3811–3813). This region includes 7 coding exons (6–12) containing 74, 132, 114, 147, 96, 121, and 123 bp respectively. Exons 8–12 contain four zinc finger motifs. Exons 7–11 all begin in the first nucleotide of a codon. Precise mapping of five t(4;11) breakpoints localized them to introns between exons 6 and 7, 7 and 8, and 8 and 9 (FIG. 10A). These breaks in chromosome 11 result in removal of the N-terminal 996 amino acids from the ALL-1 protein, as well as in disjoining of the 5' noncoding region of the gene.

If the breaks on chromosome 4 occur within a gene positioned with its 5' terminus toward the centromere, t(4;11) translocations should result in fusion of the ALL-1 gene to the gene aforementioned and, consequently, in production of two reciprocal chimeric RNAs. To investigate this possibility, a cDNA library was constructed from RNA extracted from the RS4;11 leukemic cell line established from a patient with the t(4;11) chromosome translocation (Stong, RG, and Kersey, JH, *Blood* 1985, 66, 439–443). This RS4;11 cDNA library was constructed by treating polyadenylated RNA with 1 mM methyl mercury for 10 minutes at room temperature, followed by neutralization with 10 mM mercaptoethanol and alcohol precipitation. cDNA was prepared by using the Time Saver kit (Pharmacia) and was cloned into the lambda ZAP II vector (Stratagene).

The library (2×10⁶ clones) was screened with a probe composed of exons 3–13. Twenty positive clones were purified and mapped. Two clones varied from normal ALL-1 cDNA and were further analyzed by sequencing.

Figure 10B:
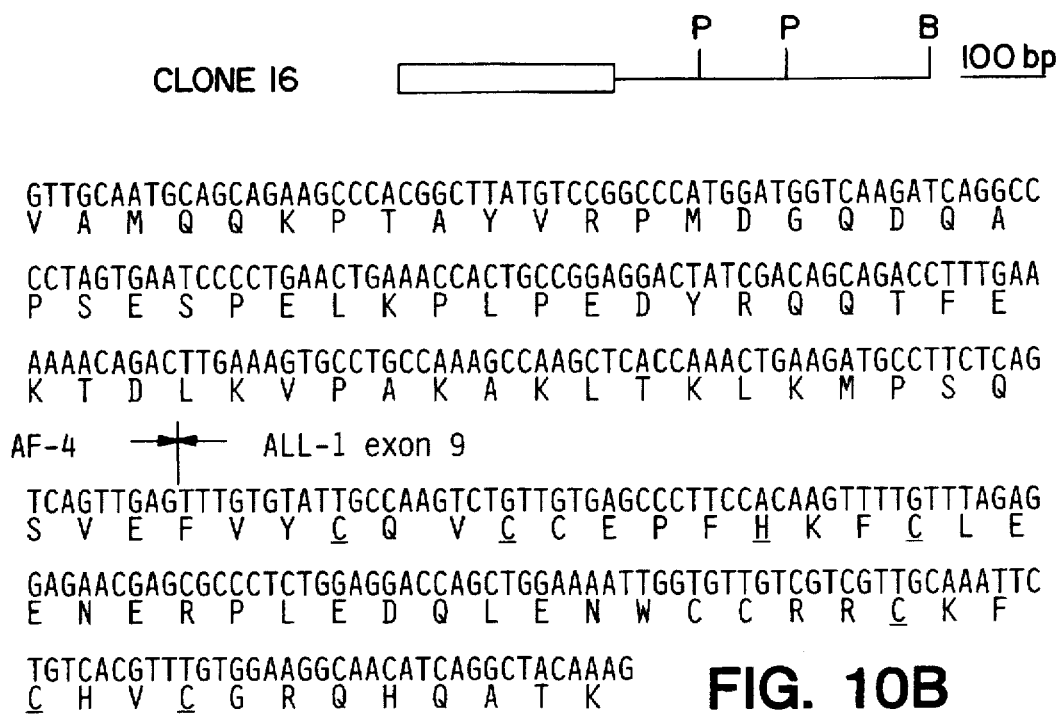
Figure 10C:
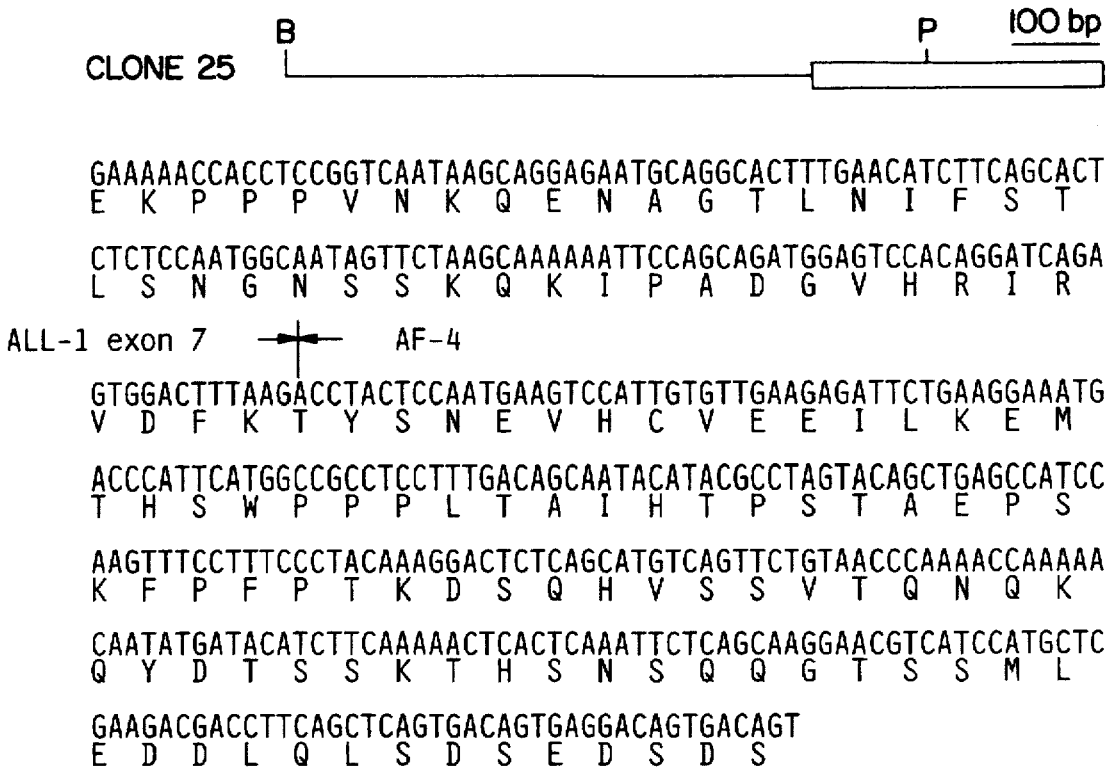

Clone 16 contained normal ALL-1 sequences 3' to the beginning of exon 9. 5' to this position, ALL-1 information was substituted with a new DNA fragment composed of an open reading frame (ORF) that joins in phase the rest of ALL-1 ORF (FIG. 10B). Clone 25 had a reciprocal configuration in which exon 7 of ALL-1 is linked to a new DNA segment containing an open reading frame. Here again, the two ORFs are joined in phase (FIG. 10C). Since, in the RS4;11 cell line, the breakpoint on chromosome 11 is within an intron located between ALL-1 exons 7 and 8 (FIG. 10A), it was expected that in the putative chimeric RNAs sequences of these exons will be directly linked to the new cDNA sequence. This is indeed the case in clone 25 but not in clone 16. In the latter, it was assumed that exon 8 was excluded from the fused transcript by a mechanism involving alternative splicing. Skipping this exon retains the fused ORFs in phase.

The identification of new sequences linked to ALL-1 cDNA in RS4;11 leukemic cells suggested that they originated from altered RNAs specific to cells with the t(4;11) chromosome translocation. Previously, two such transcripts were identified: a 14 kb RNA (previously estimated as 11.5 kb containing 3' ALL-1 sequences and a 12.7 kb RNA (previously estimated as 11 kb) hybridizing to 5' ALL-1 probe. These RNA were transcribed from chromosome derivatives 4 and 11 respectively.

A radiolabelled probe composed of non ALL-1 sequences of clone 16 was examined for hybridization to RNAs from cell lines with or without the t(4;11) chromosome translocation. As a control, the RNAs were first hybridized to 3' ALL-1 cDNA probe which detected the major normal transcript of 15–16 kb (previously estimated as 12.5 kb) in all cell lines and an altered 14 kb RNA (previously estimated as 11.5 kb) in the three cell lines with t(4;11) (FIG. 11A).

Figure 11:
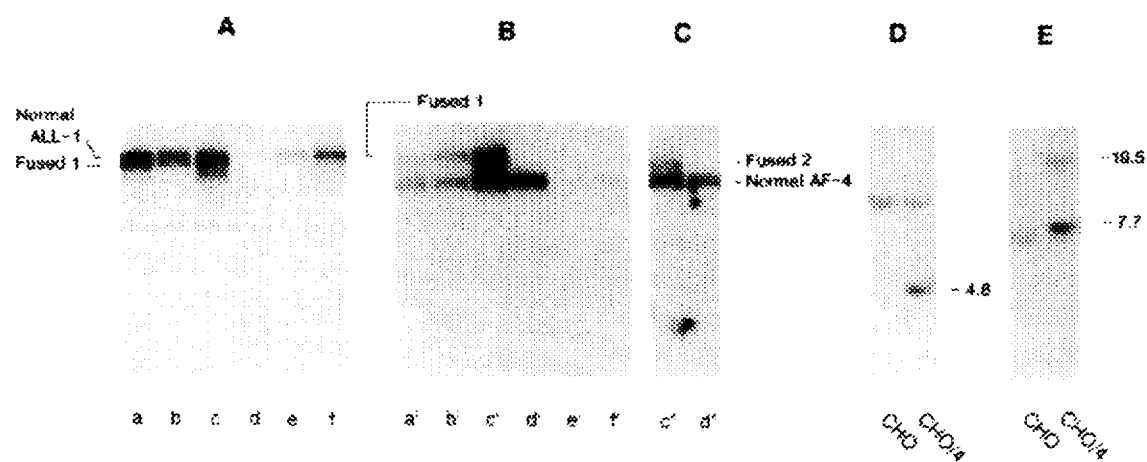
FIG. 11 shows the non ALL-1 sequences within the fused RNAs unique to cells with t(4;11) chromosome translocations (A–C) originate from chromosome 4 (D, E). Cell lines with t(4;11) chromosome translocations included: RS4;11 (Stong, RG, and Kersey, JH. Blood 1985, 66, 439–443), MV4;11 (Lange et al., Blood 1987, 70, 192–198) and B1 (Cohen et al., Blood 1991, 78, 94–102). Northern blots with RNAs from cell lines with translocations t(4;11)-B-1 (a, a'), MV4;11 (b, b') and RS4;11 (c, c', c"), and RNAs from control cell lines without the translocation: ALL-1 (d, d', d"), K562 (e, e'), SKDHL (f, f'), were hybridized to 5' ALL-1 cDNA probe (A), to non ALL-1 sequences from cDNA clone 16 (B), and to non ALL-1 sequences from cDNA clone 25 (C). ALL-1 is a Philadelphia-chromosome positive cell line (B cell leukemia) lacking 11q23 aberrations (Erikson et al., Proc Natl. Acad. Sci. U.S.A. 1986, 83, 1807–1811). K562 originated from chronic myelogenous leukemia (Lozzio, CB and Lozzio, BB. Blood 1975, 45, 321–324). SKDHL is a B cell lymphoma cell line (Saito et al., Proc. Natl. Acad. Sci. U.S.A. 1983, 80, 7476–7480). The second and third probes were also used in hybridization to Southern blots (D and E, respectively) with DNAs from Chinese hamster ovary (CHO cells and CHO cells containing chromosome 4 (CHO/4). "Fused 1" and "fused 2" correspond to the altered ALL-1 RNAs of 14 kb and 2.7 kb, respectively.

Clone 16 probe identified a 9.5 kb RNA in all cells examined and a 14 kb transcript in RS4;11, MV4;11 and B-1 cells (FIG. 11B). It was concluded that clone 16 originated from the 14 kb altered ALL-1 transcript and that the non-ALL-1 sequence within this RNA is expressed in human cells as a 9.5 kb transcript, which corresponds to the normal AF-4 transcript on a non-rearranged chromosome 4.

In an analogous experiment, a probe composed of non-ALL-1 sequences in clone 25 hybridized to the 12.7 kb altered RNA present in the RS4;11 cell line and to a 9.5 kb RNA species present in RS4;11 cells and in control cells (FIG. 11C). Thus, clone 25 originated from the second altered 12.7 kb ALL-1 RNA unique to cells with the t(4;11) chromosome translocation.

The chromosome from which the new sequences of clones 16 and 25 originated was then identified. High molecular weight DNAs from lines of Chinese hamster ovary (CHO) cells with or without human chromosome 4 were digested with BamHI enzyme and analyzed by Southern blotting for hybridization to the non ALL-1 sequence in clone 16 (FIG. 11D) and clone 25 (FIG. 11E). The cell lines showed an 11 kb or a 6.6 kb band representing CHO cell DNA cross-reacting with the probes. A fragment of 4.8 kb and fragments of 7.7 and 19.5 kb were detected in the somatic cell hybrid line containing human chromosome 4 (CHO/4) after hybridization with non ALL-1 sequences of clones 16 and 25, respectively (FIGS. 11D and E). The non-ALL-1 sequences in clone 25 hybridized to specific segment within cloned chromosome 4 DNA spanning the RS4;11 breakpoint. Thus, clones 16 and 25 correspond to the two reciprocal fused transcripts of the ALL-1 gene and a gene on chromosome 4. The latter is denominated "AF-4" for ALL-1 fused gene from chromosome 4.

Cloning and sequence analysis of the ALL-1 gene indicates that it encodes an unusually large protein of 4,000 amino acids with a mass of approximately 400 kD. The striking feature of the protein is its homology to the Drosophila trithorax gene. The homology is reflected in three ways. First, the transcripts and proteins have a similar size; the Drosophila gene is transcribed into a 15 kb RNA encoding a protein of 3759 amino acids (Mozer, BA, and David, IB, *Proc. Natl. Acad. Sci. U.S.A.* 1989, 86, 3738–3742; Mazo et al., *Proc. Natl. Acad. Sci. U.S.A.* 1990, 87, 2112–2116).

Second, there is strong sequence homology in three regions, two of which contain zinc finger-like domains unique to the trithorax gene and presumably utilized in interaction with target DNA. The third region shows 82% similarity and 61% identity across 220 amino acids which end both proteins at their C-terminus.

Finally, there is colinearity of the homologous sequences in the two proteins. Although the sequence homology does not extend to other parts of the protein, the two genes very possibly evolved from a common ancestor and may carry out similar function(s). In this context, it has been previously noted that structural homology between Drosophila and mammalian genes such as the Antennapedia class homeobox genes, is frequently limited to the functional domains, e.g., the homeodomain (McGinnis, W, and Krumlauf, R., *Cell* 1992, 68, 283–302).

The trithorax gene in Drosophila acts to maintain spatially-restricted expression patterns of the Antennapedia and Bithorax complexes during fruit fly development (Ingham, PW, *Cold Spring Harbor Symp. Quant. Biol.* 1985, 50, 201–208). Trithorax activates transcription of multiple genes of the two complexes and, as such, counteracts the activity of Polycomb group genes which act as repressors of transcription for the same genes (McKeon, J and Brock, HW, *Roux's Arch. Dev. Biol.* 1991, 199, 387–396). Thus, mutations in the trithorax gene frequently result in homeotic transformations (Capdevila, MP and Garcia-Bellido, A., *Roux's Arch. Dev. Biol.* 1981, 190, 339–350). The discovery of zinc finger-like domains in the predicted amino acid sequence strongly suggested that the trithorax protein is a transcription factor which binds to DNA (Mazo et al., *Proc. Natl. Acad. Sci. U.S.A.* 990, 87, 2112–2116). Indeed, antibodies to the protein react with specific regions of the chromatin in the salivary glands of Drosophila.

Based on what is known about the Drosophila gene, it is very likely that the ALL-1 gene is a transcription factor and that it is involved in regulation of genes controlling human development and/or differentiation. While expression of ALL-1 during embryonic development has not yet been investigated, the isolation of ALL-1 sequences from a human fetal cDNA library indicates transcription of the gene during fetal development. Previous studies (Cimino et al., *Cancer Research* 1992, 52, 3811–3813) demonstrated ALL-1 RNA in a variety of hematopoietic cell lines, as well as in tumors originating from precursors of epithelial and glial cells.

It was also found that the t(4;11) chromosome translocation cleaves the ALL-1 gene within the coding region and results in fusion of the open reading frames of ALL-1 and a gene on chromosome 4 (termed AF-4) in phase. The breakpoints on chromosome 11 cluster in a region containing several small exons, 5 of them (exons 7–11) begin in the first letter of a codon. Splicing from the same exon on chromosome 4, adjacent to the breakpoint in RS4;11, to each one of the five exons on chromosome 11 will retain the two open reading frames fused in phase. This situation is similar to the situation in the t(9;22) chromosome translocations where the breakpoints cluster near two BCR exons whose splicing to ABL exon 11 maintain the fused open reading frames in phase (Shtivelman et al., *Nature* 1985, 315, 550–554; Heisterkamp et al., *Nature* 1985, 315, 758–761). The clustering of breakpoints must also reflect the specific biological properties of the fused proteins and probably is also due to the presence of recombination signals in this region.

Two chimeric proteins from the 12.7 and 14 kb RNAs are predicted for cells with the t(4;11) chromosome translocation. The lack of information about the normal AF-4 protein precludes at this time the determination if it is also a transcription factor that exchanges functional domains with ALL-1 to give a chimeric transcription factor. This occurs in the t(1;19) and t(15;17) chromosome translocations (Kamps et al., *Cell* 1990, 60, 547–555; Nourse et al., *Cell* 1990, 60, 535–545; Kakizuka et al., *Cell* 1991, 66, 663–674; de The et al., *Cell* 1991, 66, 675–654).

Both the 12.7 and the 14 kb fused RNAs are found in the three cell lines with t(4;11), therefore it is not possible at this time to establish which of the two products is oncogenic. However, the presence of the three trithorax homologous domains within the 14 kb transcript makes it an attractive candidate. The substitution of the N-terminus 996 amino acids of ALL-1 with an AF-4 polypeptide could result in at least two scenarios, both based on the assumption that ALL-1 and ALL-1/AF-4 activate transcription of the same gene(s). First, the substitution could place ALL-1 DNA binding domain under the control of a new effector domain activated by either ubiquitous or tissue specific factors. This will result in transcription of the target genes in the wrong cells. Second, the fusion product may function as a dominant negative inhibitor of ALL-1 by forming inactive heterodimers or by occupying target DNA sites.

The present invention provides methods of diagnosis for human leukemia by providing a tissue sample from a person suspected of having acute lymphocytic, myelomonocytic, monocytic or myelogenous leukemia, and determining if there are breakpoints on chromosome 11 in the ALL-1 locus. The sequence of the ALL-1 cDNA can be used to generate probes to detect chromosome abnormalities in the ALL-1 breakpoint cluster region. These probes may be generated from both the sense and antisense strands of double-stranded DNA. The term "ALL-1 probe" refers to both genomic and cDNA probes derived from the ALL-1 gene.

It is believed that genomic probes capable of detecting chromosomal translocations involving the ALL-1 breakpoint cluster region span sequences from 10 kb centromeric to 10 kb telomeric to the breakpoint cluster region, which has been shown to span at least exons 6–9, and may span exons 6–12 of the ALL-1 gene. It is believed that cDNA probes capable detecting chromosomal translocations involving the breakpoint cluster region span sequences ranging from 2 kb centromeric to 2 kb telomeric to the breakpoint cluster region. Thus, preferred embodiments of the present invention for detecting chromosomal abnormalities involving ALL-1 provide genomic and cDNA probes spanning the chromosome 11 regions described above. cDNA probes are more preferred, and probes comprising the exons included in the breakpoint cluster region are most preferred.

Part or all of the ALL-1 cDNA sequence may be used to create a probe capable of detecting aberrant transcripts resulting from chromosome 11 translocations. The EcoRI probe, for example, was derived from a genomic clone but its location lies within an exon. Thus, preferred embodiments of the present invention for detecting aberrant transcripts provide cDNA probes spanning the ALL-1 gene.

The ALL-1/AF-4 sequences provided in SEQ ID NO: 23 and SEQ ID NO: 24 can be used to create probes to detect t(4;11) chromosome abnormalities and aberrant transcripts corresponding to t(4;11) translocations.

Using the probes of the present invention, several methods are available for detecting chromosome abnormalities in the ALL-1 gene on chromosome 11. Such methods include, for example, Polymerase Chain Reaction (PCR) technology, restriction fragment length analysis, and oligonucleotide hybridization using, for example, Southern and Northern blotting and in situ hybridization.

PCR technology is practiced routinely by those having ordinary skill in the art and its uses in diagnostics are well known and accepted. Methods for practicing PCR technology are disclosed in PCR Protocols: *A Guide to Methods and Applications*, Innis, M.A. et al., Eds., Academic Press, San Diego, Calif. 1990, and RT-PCR, Clontech Laboratories (1991), which are incorporated herein by reference. Applications of PCR technology are disclosed in *Polymerase Chain Reaction*, Erlich, H. A. et al., Eds., Cold Spring Harbor Press, Cold Spring Harbor, N.Y. 1989, which is incorporated herein by reference.

PCR technology allows for the rapid generation of multiple copies of DNA sequences by providing 5' and 3' primers that hybridize to sequences present in a DNA molecule, and further providing free nucleotides and an enzyme which fills in the complementary bases to the DNA sequence between the primers with the free nucleotides to produce a complementary strand of DNA. The enzyme will fill in the complementary sequences between probes only if both the 5' primer and 3' primer hybridize to DNA sequences on the same strand of DNA.

To detect rearrangements involving chromosomes 11 and 4, one of the two probes can be generated from the ALL-1 cDNA and one probe from the AF-4 gene. RNA is isolated from hematopoietic cells of a person suspected of having acute lymphoblastic or nonlymphoblastic leukemia, and cDNA is generated from the mRNA. If the cDNA of the chimeric ALL-1/AF-4 gene is present, both primers will hybridize to the cDNA and the intervening sequence will be amplified. The PCR technology therefore provides a straightforward and reliable method of detecting the chimeric gene.

The preferred primers for PCR are selected, one from a portion of SEQ ID NO: 1, corresponding to the ALL-1 cDNA, and one from a portion of either SEQ ID NO: 19 or SEQ ID NO: 22, corresponding to AF-4 gene sequences. Preferably, the sequences chosen from SEQ ID NO: 1 comprise at least a portion of SEQ ID NO: 20, which corresponds to exon 9, or SEQ ID NO: 21, which corresponds to exon 7.

According to the invention, diagnostic kits can be assembled which are useful to practice oligonucleotide hybridization methods of distinguishing chromosome 11 abnormalities from non-rearranged chromosomes 11. Such diagnostic kits comprise a labelled oligonucleotide which hybridizes, for example, to the chimeric transcript that results from t(4;11) translocations but which does not hybridize to nucleic acid transcripts not associated with aberrations. Accordingly, diagnostic kits of the present invention comprise, for example, a labelled probe that includes ALL-1 and AF-4 sequences which make up the chimeric transcript associated with t(4;11) translocations. Such probes comprise oligonucleotides having at least a portion of the sequence the ALL-1/AF-4 gene of SEQ ID NO: 23 or SEQ ID NO: 24.

It is preferred that labelled probes of the oligonucleotide diagnostic kits according to the present invention are labelled with a radionucleotide. The oligonucleotide hybridization-based diagnostic kits according to the invention preferably comprise DNA samples that represent positive and negative controls. A positive control DNA sample is one that comprises a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Under assay conditions, the probe will not hybridize to the negative control DNA sample.

Antisense oligonucleotides which hybridize to at least a portion of an aberrant transcript resulting from chromosome 11 abnormalities involving the ALL-1 gene are also contemplated by the present invention. The oligonucleotide may match the target region exactly or may contain several mismatches. Thus, molecules which bind competitively to RNA coded by the chimeric ALL-1/AF-4 gene, for example, are envisioned for therapeutics. Preferred embodiments include antisense oligonucleotides capable of binding to at least a portion of SEQ ID NO: 23 and SEQ ID NO: 24.

Preferred embodiments of the present invention include antisense oligonucleotides capable of binding to a region of the ALL-1/AF-4 mRNA corresponding to the ALL-1 sequences which encode a peptide having homology with the Drosophila trithorax protein and antisense oligonucleotides capable of binding to a region of the mRNA encoding a zinc finger-like domain in the ALL-1 protein.

While any length oligonucleotide may be utilized, sequences shorter than 15 bases may be less specific in hybridizing to the target and may be more easily destroyed by enzymatic degradation. Hence, oligonucleotides having at least 15 nucleotides are preferred. Sequences longer than 2 nucleotides may be somewhat less effective in interfering with ALL-1 expression because of decreased uptake by the target cell. Therefore, oligonucleotides of 15–21 nucleotides are most preferred.

The term "oligonucleotide" as used herein includes both ribonucleotides and deoxyribonucleotides, and includes molecules which may be long enough to be termed "polynucleotides." Oligodeoxyribonucleotides are preferred since oligoribonucleotides are more susceptible to enzymatic attack by ribonucleases than deoxyribonucleotides. It will also be understood that the bases, sugars or internucleotide linkages may be chemically modified by methods known in the art. Modifications may be made, for example, to improve stability and/or lipid solubility. For instance, it is known that enhanced lipid solubility and/or resistance to nuclease digestion results by substituting a methyl group or sulfur atom for a phosphate oxygen in the internucleotide phosphodiester linkage. The phosphorothioates, in particular, are stable to nuclease cleavage and soluble in lipid. Modified oligonucleotides are termed "derivatives."

The oligonucleotides of the present invention may be synthesized by any of the known chemical oligonucleotide synthesis methods. See for example, Gait, M. J., ed. (1984), *Oligonucleotide Synthesis* (IRL, Oxford). Since the entire sequence of the ALL-1 gene has been provided along with partial sequences of the AF-4 gens, antisense oligonucleotides hybridizable with any portion of these sequences may be prepared by the synthetic methods known by those skilled in the art.

It is generally preferred to apply the therapeutic agent in accordance with this invention internally such as intravenously, transdermally or intramuscularly. Other forms of administration such as topically or interlesionally may also be useful. Inclusion in suppositories is presently believed to be likely to be highly useful. Use of pharmacologically acceptable carriers is also preferred for some embodiments.

For in vivo use, the antisense oligonucleotides may be combined with a pharmaceutical carrier, such as a suitable liquid vehicle or excipient and an optional auxiliary additive or additives. The liquid vehicles and excipients are conventional and commercially available. Illustrative thereof are distilled water, physiological saline, aqueous solution of dextrose, and the like. In addition to administration with conventional carriers, the antisense oligonucleotides may be administered by a variety of specialized oligonucleotide delivery techniques. For example, oligonucleotides have been successfully encapsulated in unilameller liposomes. Reconstituted Sendai virus envelopes have been successfully used to deliver RNA and DNA to cells. Arad et al., *Biochem. Biophy. Acta.* 1986, 859, 88–94.

For in vivo use, the antisense oligonucleotides may be administered in an amount effective to result in extracellular concentrations approximating in vitro concentrations described below. The actual dosage administered may take into account the size and weight of the patient, whether the nature of the treatment is prophylactic or therapeutic in nature, the age, weight, health and sex of the patient, the route of administration, and other factors. The daily dosage may range from about 0.1 to 1,000 oligonucleotide per day, preferably from about 10 to about 1,000 mg per day. Greater or lesser amounts of oligonucleotide may be administered, as required.

It is also possible to administer the antisense oligonucleotides ex vivo by isolating white blood cells from peripheral blood, treating them with the antisense oligonucleotides, then returning the cells to the donor's blood. Ex vivo techniques have been used in the treatment of cancer patients with interleukin-2 activated lymphocytes.

For ex vivo application, for example, in bone marrow purging, the antisense oligonucleotides may be administered in amounts effective to kill leukemic cells while maintaining the viability of normal hematologic cells. Such amounts may vary depending on the nature and extent of the leukemia, the particular oligonucleotide utilized, the relative sensitivity of the leukemia to the oligonucleotide, and other factors. Concentrations from about 10 to 100 µg/ml per $10^5$ cells may be employed, preferably from about 40 to about 60 µg/ml per $10^5$ cells. Supplemental dosing of the same or lesser amounts of oligonucleotide are advantageous to optimize the treatment. Thus, for purging bone marrow containing $2 \times 10^7$ per ml of marrow volume, dosages from about 2 to about 20 mg antisense per ml of marrow may be effectively utilized, preferably from about 8 to 12 mg/ml. Greater or lesser amounts of oligonucleotide may be employed.

The present invention is also directed to monoclonal antibodies capable of binding to the chimeric ALL-1/AF-4 protein, including monoclonal antibodies capable of binding to a region of the protein having homology with the Drosophila trithorax protein and monoclonal antibodies capable of binding to a zinc finger-like domain. Such monoclonal antibodies are useful as diagnostic and therapeutic agents for leukemias characterized by t(4;11) translocations. Thus, the present invention encompasses immunoassays for detecting at least a portion of the ALL-1/AF-4 protein. In addition, the instant invention contemplates diagnostic kits comprising a monoclonal antibody to at least a portion of ALL-1/AF-4 in combination with conventional diagnostic kit components.

The present invention is also directed to pharmaceutical compositions comprising monoclonal antibodies and a suitable pharmaceutical carrier, which are well known in the pharmaceutical art, and are described, for example, in Remington's *Pharmaceutical Sciences,* Gennaro, A. R., ed., Mack Publishing Co., Easton, Pa. 1985. The useful dosage will vary depending upon the age, weight, and particular patient treated.

Polyclonal antibodies to the instant polypeptides are also within the ambit of the invention. Such polyclonal antibodies may be produced using standard techniques, for example, by immunizing a rabbit or a rat with a protein or peptide of the invention, removing serum from the rabbit, and harvesting the resultant polyclonal antibodies from the serum. If desired, the polyclonal antibodies may be used as an IgG fraction or may be further purified in varying degrees. Procedures for preparing, harvesting and purifying polyclonal antibodies are well known in the art, and are described, for example, in *Methods in Immunology:* A Laboratory Text for *Instruction and Research,* Garvey et al., Ed., W. A. Benjamin, Reading MA, 1977, 3rd ed., chapter 22, 24–30.

What is claimed is:

1. A DNA molecule comprising human genomic DNA nucleotide sequences consisting of the human genomic DNA insert in cos 20, cos 43, cos 53, phage mg 11.1, phage c14, or phage gc3, or a fragment of said human genomic DNA insert having at least 15 nucleotides.

2. The DNA molecule of claim 1 comprising human genomic DNA nucleotide sequences consisting of the human genomic DNA insert in cos 20, cos 43, cos 53, phage mg 11.1, phage c14, or phage gc3.

3. The DNA molecule of claim 1 comprising human genomic DNA nucleotide sequences consisting of a fragment of the human genomic DNA insert in cos 20, cos 43, cos 53, phage mg 11.1, phage c14, or phage gc3 having at least 15 nucleotides.

4. The DNA molecule of claim 1 wherein said DNA molecule consists of human genomic DNA nucleotide sequences of the human genomic DNA insert in cos 20, cos 43, cos 53, phage mg 11.1, phage c14, or phage gc3, or a fragment of said human genomic DNA insert having at least 15 nucleotides.

5. The DNA molecule of claim 4 wherein said DNA molecule consists of human genomic DNA nucleotide sequences of the human genomic DNA insert in cos 20, cos 43, cos 53, phage mg 11.1, phage c14, or phage gc3.

6. The DNA molecule of claim 4 wherein said DNA molecule consists of human genomic DNA nucleotide sequences of a fragment the human genomic DNA insert in cos 20, cos 43, cos 53, phage mg 11.1, phage c14, or phage gc3 having at least 15 nucleotides.

7. The DNA molecule of claim 6 wherein said DNA molecule consists of human genomic DNA nucleotide sequences of a fragment the human genomic DNA insert in cos 20, cos 43, cos 53, phage mg 11.1, phage c14, or phage gc3 having at least 21 nucleotides.

8. The DNA molecule of claim 7 wherein said DNA molecule consists of a fragment of human genomic DNA nucleotide sequences of the human genomic DNA insert in cos 20 having 1500 nucleotides.

9. The DNA molecule of claim 7 wherein said DNA molecule consists of a fragment of human genomic DNA nucleotide sequences of the human genomic DNA insert in cos 53 having 500 nucleotides.

10. The DNA molecule of claim 7 wherein said DNA molecule consists of a fragment of human genomic DNA nucleotide sequences of the human genomic DNA insert in cos 53 having 700 nucleotides.

11. A DNA molecule consisting of SEQ ID NO: 1 or a fragment thereof of at least 15 nucleotides.

12. The DNA molecule of claim 11 consisting of SEQ ID NO: 1.

13. The DNA molecule of claim 11 consisting of a fragment thereof of at least 15 nucleotides.

14. The DNA molecule of claim 13 consisting of a fragment thereof of at least 21 nucleotides.

15. A DNA molecule of claim 14 consisting of nucleotide sequences identical to the nucleotide sequence of the human cDNA in clone SKV2, SKV3, SKV18, V1, V2, V8, V13, V26 or 9B1.

16. A DNA molecule consisting of a nucleotide sequence fully complementary to SEQ ID NO: 1 or a fragment thereof of at least 15 nucleotides.

* * * * *

UNITED STATES PATENT AND TRADEMARK OFFICE
CERTIFICATE OF CORRECTION

PATENT NO. : 5,633,136                                      Page 1 of 2
DATED      : May 27, 1997
INVENTOR(S): Carlo Croce and Eli Canaani It is certified that error appears in the above-indentified patent and that said Letters Patent is hereby corrected as shown below:

Col. 4, line 37, "2.7" should be --12.7--

Col. 4, line 44, "gens" should be --gene--

Col..4, line 49, "gens" should be --gene--

Col. 4, line 52, "anti" shoud be --and--

Col. 4, line 57, "gens" should be --gene--

Col. 4,line 58, " gens" should be --gene--

Col. 5, line 3, after "lines" insert --and--

Col. 5, line 5, at the end of the line "et' should include --al;--

Col. 6, line 17, "leukemia" should be --leukemias--

Col. 7, line 25, "al" should be --all--

UNITED STATES PATENT AND TRADEMARK OFFICE
CERTIFICATE OF CORRECTION

PATENT NO. : 5,633,136
DATED : May 27, 1997
INVENTOR(S) : Carlo Croce and Eli Canaani It is certified that error appears in the above-indentified patent and that said Letters Patent is hereby corrected as shown below:

Col. 8, line 65, after "revealed" insert --a--

Col. 14, line 37, "2" should be --21--.

Col. 14, line 62, "gens" should be --gene--

Signed and Sealed this

Twenty-third Day of September, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 24

( 2 ) INFORMATION FOR SEQ ID NO: 1:

( i ) SEQUENCE CHARACTERISTICS:
( A ) LENGTH: 14255
( B ) TYPE: nucleic acid
( C ) STRANDEDNESS: single
( D ) TOPOLOGY: linear ( i v ) ANTI-SENSE: No ( x i ) SEQUENCE DESCRIPTION: SEQ ID NO: 1:

```
GCG  GCG  GCG  GCG  GCG  GGA  AGC  AGC  GGG  GCT  GGG  GTT  CCA  GGG  GGA    4 5
Ala  Ala  Ala  Ala  Ala  Gly  Ser  Ser  Gly  Ala  Gly  Val  Pro  Gly  Gly
  5                          1 0                          1 5
```

```
GCG GCC GCC GCC TCA GCA GCC TCC TCG TCG TCC GCC TCG TCT TCG   90
Ala Ala Ala Ala Ser Ala Ala Ser Ser Ser Ser Ala Ser Ser Ser
              20              25              30

TCT TCG TCA TCG TCC TCA GCC TCT TCA GGG CCG GCC CTG CTC CGG  135
Ser Ser Ser Ser Ser Ser Ala Ser Ser Gly Pro Ala Leu Leu Arg
              35              40              45

GTG GGC CCG GGC TTC GAC GCG GCG CTG CAG GTC TCG GCC GCC ATC  180
Val Gly Pro Gly Phe Asp Ala Ala Leu Gln Val Ser Ala Ala Ile
              50              55              60

GGC ACC AAC CTG CGC CGG TTC CGG GCC GTG TTT GGG GAG AGC GGC  225
Gly Thr Asn Leu Arg Arg Phe Arg Ala Val Phe Gly Glu Ser Gly
              65              70              75

GGG GGA GGC GGC AGC GGA GAG GAT GAG CAA TTC TTA GGT TTT GGC  270
Gly Gly Gly Gly Ser Gly Glu Asp Glu Gln Phe Leu Gly Phe Gly
              80              85              90

TCA GAT GAA GAA GTC AGA GTG CGA AGT CCC ACA AGG TCT CCT TCA  315
Ser Asp Glu Glu Val Arg Val Arg Ser Pro Thr Arg Ser Pro Ser
              95             100             105

GTT AAA ACT AGT CCT CGA AAA CCT CGT GGG AGA CCT AGA AGT GGC  360
Val Lys Thr Ser Pro Arg Lys Pro Arg Gly Arg Pro Arg Ser Gly
             110             115             120

TCT GAC CGA AAT TCA GCT ATC CTC TCA GAT CCA TCT GTG TTT TCC  405
Ser Asp Arg Asn Ser Ala Ile Leu Ser Asp Pro Ser Val Phe Ser
             125             130             135

CCT CTA AAT AAA TCA GAG ACC AAA TCT GGA GAT AAG ATC AAG AAG  450
Pro Leu Asn Lys Ser Glu Thr Lys Ser Gly Asp Lys Ile Lys Lys
             140             145             150

AAA GAT TCT AAA AGT ATA GAA AAG AAG AGA GGA AGA CCT CCC ACC  495
Lys Asp Ser Lys Ser Ile Glu Lys Lys Arg Gly Arg Pro Pro Thr
             155             160             165

TTC CCT GGA GTA AAA ATC AAA ATA ACA CAT GGA AAG GAC ATT TCA  540
Phe Pro Gly Val Lys Ile Lys Ile Thr His Gly Lys Asp Ile Ser
             170             175             180

GAG TTA CCA AAG GGA AAC AAA GAA GAT AGC CTG AAA AAA ATT AAA  585
Glu Leu Pro Lys Gly Asn Lys Glu Asp Ser Leu Lys Lys Ile Lys
             185             190             195

AGG ACA CCT TCT GCT ACG TTT CAG CAA GCC ACA AAG ATT AAA AAA  630
Arg Thr Pro Ser Ala Thr Phe Gln Gln Ala Thr Lys Ile Lys Lys
             200             205             210

TTA AGA GCA GGT AAA CTC TCT CCT CTC AAG TCT AAG TTT AAG ACA  675
Leu Arg Ala Gly Lys Leu Ser Pro Leu Lys Ser Lys Phe Lys Thr
             215             220             225

GGG AAG CTT CAA ATA GGA AGG AAG GGG GTA CAA ATT GTA CGA CGG  720
Gly Lys Leu Gln Ile Gly Arg Lys Gly Val Gln Ile Val Arg Arg
             230             235             240

AGA GGA AGG CCT CCA TCA ACA GAA AGG ATA AAG ACC CCT TCG GGT  765
Arg Gly Arg Pro Pro Ser Thr Glu Arg Ile Lys Thr Pro Ser Gly
             245             250             255

CTC CTC ATT AAT TCT GAA CTG GAA AAG CCC CAG AAA GTC CGG AAA  810
Leu Leu Ile Asn Ser Glu Leu Glu Lys Pro Gln Lys Val Arg Lys
             260             265             270

GAC AAG GAA GGA ACA CCT CCA CTT ACA AAA GAA GAT AAG ACA GTT  855
Asp Lys Glu Gly Thr Pro Pro Leu Thr Lys Glu Asp Lys Thr Val
             275             280             285

GTC AGA CAA AGC CCT CGA AGG ATT AAG CCA GTT AGG ATT ATT CCT  900
Val Arg Gln Ser Pro Arg Arg Ile Lys Pro Val Arg Ile Ile Pro
             290             295             300

TCT TCA AAA AGG ACA GAT GCA ACC ATT GCT AAG CAA CTC TTA CAG  945
Ser Ser Lys Arg Thr Asp Ala Thr Ile Ala Lys Gln Leu Leu Gln
             305             310             315
```

```
AGG GCA AAA AAG GGG GCT CAA AAG AAA ATT GAA AAA GAA GCA GCT   990
Arg Ala Lys Lys Gly Ala Gln Lys Lys Ile Glu Lys Glu Ala Ala
        320                 325                 330

CAG CTG CAG GGA AGA AAG GTG AAG ACA CAG GTC AAA AAT ATT CGA  1035
Gln Leu Gln Gly Arg Lys Val Lys Thr Gln Val Lys Asn Ile Arg
        335                 340                 345

CAG TTC ATC ATG CCT GTT GTC AGT GCT ATC TCC TCG CGG ATC ATT  1080
Gln Phe Ile Met Pro Val Val Ser Ala Ile Ser Ser Arg Ile Ile
        350                 355                 360

AAG ACC CCT CGG CGG TTT ATA GAG GAT GAG GAT TAT GAC CCT CCA  1125
Lys Thr Pro Arg Arg Phe Ile Glu Asp Glu Asp Tyr Asp Pro Pro
        365                 370                 375

ATT AAA ATT GCC CGA TTA GAG TCT ACA CCG AAT AGT AGA TTC AGT  1170
Ile Lys Ile Ala Arg Leu Glu Ser Thr Pro Asn Ser Arg Phe Ser
        380                 385                 390

GCC CCG TCC TGT GGA TCT TCT GAA AAA TCA AGT GCA GCT TCT CAG  1215
Ala Pro Ser Cys Gly Ser Ser Glu Lys Ser Ser Ala Ala Ser Gln
        395                 400                 405

CAC TCC TCT CAA ATG TCT TCA GAC TCC TCT CGA TCT AGT AGC CCC  1260
His Ser Ser Gln Met Ser Ser Asp Ser Ser Arg Ser Ser Ser Pro
        410                 415                 420

AGT GTT GAT ACC TCC ACA GAC TCT CAG GCT TCT GAG GAG ATT CAG  1305
Ser Val Asp Thr Ser Thr Asp Ser Gln Ala Ser Glu Glu Ile Gln
        425                 430                 435

GTA CTT CCT GAG GAG CGG AGC GAT ACC CCT GAA GTT CAT CCT CCA  1350
Val Leu Pro Glu Glu Arg Ser Asp Thr Pro Glu Val His Pro Pro
        440                 445                 450

CTG CCC ATT TCC CAG TCC CCA GAA AAT GAG AGT AAT GAT AGG AGA  1395
Leu Pro Ile Ser Gln Ser Pro Glu Asn Glu Ser Asn Asp Arg Arg
        455                 460                 465

AGC AGA AGG TAT TCA GTG TCG GAG AGA AGT TTT GGA TCT AGA ACG  1440
Ser Arg Arg Tyr Ser Val Ser Glu Arg Ser Phe Gly Ser Arg Thr
        470                 475                 480

ACG AAA AAA TTA TCA ACT CTA CAA AGT GCC CCC CAG CAG GAG ACC  1485
Thr Lys Lys Leu Ser Thr Leu Gln Ser Ala Pro Gln Gln Glu Thr
        485                 490                 495

TCC TCG TCT CCA CCT CCA CCT CTG CTG ACT CCA CCG CCA CCA CTG  1530
Ser Ser Ser Pro Pro Pro Pro Leu Leu Thr Pro Pro Pro Pro Leu
        500                 505                 510

CAG CCA GCC TCC AGT ATC TCT GAC CAC ACA CCT TGG CTT ATG CCT  1575
Gln Pro Ala Ser Ser Ile Ser Asp His Thr Pro Trp Leu Met Pro
        515                 520                 525

CCA ACA ATC CCC TTA GCA TCA CCA TTT TTG CCT GCT TCC ACT GCT  1620
Pro Thr Ile Pro Leu Ala Ser Pro Phe Leu Pro Ala Ser Thr Ala
        530                 535                 540

CCT ATG CAA GGG AAG CGA AAA TCT ATT TTG CGA GAA CCG ACA TTT  1665
Pro Met Gln Gly Lys Arg Lys Ser Ile Leu Arg Glu Pro Thr Phe
        545                 550                 555

AGG TGG ACT TCT TTA AAG CAT TCT AGG TCA GAG CCA CAA TAC TTT  1710
Arg Trp Thr Ser Leu Lys His Ser Arg Ser Glu Pro Gln Tyr Phe
        560                 565                 570

TCC TCA GCA AAG TAT GCC AAA GAA GGT CTT ATT CGC AAA CCA ATA  1755
Ser Ser Ala Lys Tyr Ala Lys Glu Gly Leu Ile Arg Lys Pro Ile
        575                 580                 585

TTT GAT AAT TTC CGA CCC CCT CCA CTA ACT CCC GAG GAC GTT GGC  1800
Phe Asp Asn Phe Arg Pro Pro Pro Leu Thr Pro Glu Asp Val Gly
        590                 595                 600

TTT GCA TCT GGT TTT TCT GCA TCT GGT ACC GCT GCT TCA GCC CGA  1845
Phe Ala Ser Gly Phe Ser Ala Ser Gly Thr Ala Ala Ser Ala Arg
        605                 610                 615
```

```
TTG TTT TCG CCA CTC CAT TCT GGA ACA AGG TTT GAT ATG CAC AAA   1890
Leu Phe Ser Pro Leu His Ser Gly Thr Arg Phe Asp Met His Lys
            620             625             630

AGG AGC CCT CTT CTG AGA GCT CCA AGA TTT ACT CCA AGT GAG GCT   1935
Arg Ser Pro Leu Leu Arg Ala Pro Arg Phe Thr Pro Ser Glu Ala
            635             640             645

CAC TCT AGA ATA TTT GAG TCT GTA ACC TTG CCT AGT AAT CGA ACT   1980
His Ser Arg Ile Phe Glu Ser Val Thr Leu Pro Ser Asn Arg Thr
            650             655             660

TCT GCT GGA ACA TCT TCT TCA GGA GTA TCC AAT AGA AAA AGG AAA   2025
Ser Ala Gly Thr Ser Ser Ser Gly Val Ser Asn Arg Lys Arg Lys
            665             670             675

AGA AAA GTG TTT AGT CCT ATT CGA TCT GAA CCA AGA TCT CCT TCT   2070
Arg Lys Val Phe Ser Pro Ile Arg Ser Glu Pro Arg Ser Pro Ser
            680             685             690

CAC TCC ATG AGG ACA AGA AGT GGA AGG CTT AGT AGT TCT GAG CTC   2115
His Ser Met Arg Thr Arg Ser Gly Arg Leu Ser Ser Ser Glu Leu
            695             700             705

TCA CCT CTC ACC CCC CCG TCT TCT GTC TCT TCC TCG TTA AGC ATT   2160
Ser Pro Leu Thr Pro Pro Ser Ser Val Ser Ser Ser Leu Ser Ile
            710             715             720

TCT GTT AGT CCT CTT GCC ACT AGT GCC TTA AAC CCA ACT TTT ACT   2205
Ser Val Ser Pro Leu Ala Thr Ser Ala Leu Asn Pro Thr Phe Thr
            725             730             735

TTT CCT TCT CAT TCC CTG ACT CAG TCT GGG GAA TCT GCA GAG AAA   2250
Phe Pro Ser His Ser Leu Thr Gln Ser Gly Glu Ser Ala Glu Lys
            740             745             750

AAT CAG AGA CCA AGG AAG CAG ACT AGT GCT CCG GCA GAG CCA TTT   2295
Asn Gln Arg Pro Arg Lys Gln Thr Ser Ala Pro Ala Glu Pro Phe
            755             760             765

TCA TCA AGT AGT CCT ACT CCT CTC TTC CCT TGG TTT ACC CCA GGC   2340
Ser Ser Ser Ser Pro Thr Pro Leu Phe Pro Trp Phe Thr Pro Gly
            770             775             780

TCT CAG ACT GAA AGA GGG AGA AAT AAA GAC AAG GCC CCC GAG GAG   2385
Ser Gln Thr Glu Arg Gly Arg Asn Lys Asp Lys Ala Pro Glu Glu
            785             790             795

CTG TCC AAA GAT CGA GAT GCT GAC AAG AGC GTG GAG AAG GAC AAG   2430
Leu Ser Lys Asp Arg Asp Ala Asp Lys Ser Val Glu Lys Asp Lys
            800             805             810

AGT AGA GAG AGA GAC CGG GAG AGA GAA AAG GAG AAT AAG CGG GAG   2475
Ser Arg Glu Arg Asp Arg Glu Arg Glu Lys Glu Asn Lys Arg Glu
            815             820             825

TCA AGG AAA GAG AAA AGG AAA AAG GGA TCA GAA ATT CAG AGT AGT   2520
Ser Arg Lys Glu Lys Arg Lys Lys Gly Ser Glu Ile Gln Ser Ser
            830             835             840

TCT GCT TTG TAT CCT GTG GGT AGG GTT TCC AAA GAG AAG GTT GTT   2565
Ser Ala Leu Tyr Pro Val Gly Arg Val Ser Lys Glu Lys Val Val
            845             850             855

GGT GAA GAT GTT GCC ACT TCA TCT TCT GCC AAA AAA GCA ACA GGG   2610
Gly Glu Asp Val Ala Thr Ser Ser Ser Ala Lys Lys Ala Thr Gly
            860             865             870

CGG AAG AAG TCT TCA TCA CAT GAT TCT GGG ACT GAT ATT ACT TCT   2655
Arg Lys Lys Ser Ser Ser His Asp Ser Gly Thr Asp Ile Thr Ser
            875             880             885

GTG ACT CTT GGG GAT ACA ACA GCT GTC AAA ACC AAA ATA CTT ATA   2700
Val Thr Leu Gly Asp Thr Thr Ala Val Lys Thr Lys Ile Leu Ile
            890             895             900

AAG AAA GGG AGA GGA AAT CTG GAA AAA ACC AAC TTG GAC CTC GGC   2745
Lys Lys Gly Arg Gly Asn Leu Glu Lys Thr Asn Leu Asp Leu Gly
            905             910             915
```

```
CCA ACT GCC CCA TCC CTG GAG AAG GAG AAA ACC CTC TGC CTT TCC   2790
Pro Thr Ala Pro Ser Leu Glu Lys Glu Lys Thr Leu Cys Leu Ser
            920             925             930

ACT CCT TCA TCT AGC ACT GTT AAA CAT TCC ACT TCC TCC ATA GGC   2835
Thr Pro Ser Ser Ser Thr Val Lys His Ser Thr Ser Ser Ile Gly
            935             940             945

TCC ATG TTG GCT CAG GCA GAC AAG CTT CCA ATG ACT GAC AAG AGG   2880
Ser Met Leu Ala Gln Ala Asp Lys Leu Pro Met Thr Asp Lys Arg
            950             955             960

GTT GCC AGC CTC CTA AAA AAG GCC AAA GCT CAG CTC TGC AAG ATT   2925
Val Ala Ser Leu Leu Lys Lys Ala Lys Ala Gln Leu Cys Lys Ile
            965             970             975

GAG AAG AGT AAG AGT CTT AAA CAA ACC GAC CAG CCC AAA GCA CAG   2970
Glu Lys Ser Lys Ser Leu Lys Gln Thr Asp Gln Pro Lys Ala Gln
            980             985             990

GGT CAA GAA AGT GAC TCA TCA GAG ACC TCT GTG CGA GGA CCC CGG   3015
Gly Gln Glu Ser Asp Ser Ser Glu Thr Ser Val Arg Gly Pro Arg
            995             1000            1005

ATT AAA CAT GTC TGC AGA AGA GCA GCT GTT GCC CTT GGC CGA AAA   3060
Ile Lys His Val Cys Arg Arg Ala Ala Val Ala Leu Gly Arg Lys
            1010            1015            1020

CGA GCT GTG TTT CCT GAT GAC ATG CCC ACC CTG AGT GCC TTA CCA   3105
Arg Ala Val Phe Pro Asp Asp Met Pro Thr Leu Ser Ala Leu Pro
            1025            1030            1035

TGG GAA GAA CGA GAA AAG ATT TTG TCT TCC ATG GGG AAT GAT GAC   3150
Trp Glu Glu Arg Glu Lys Ile Leu Ser Ser Met Gly Asn Asp Asp
            1040            1045            1050

AAG TCA TCA ATT GCT GGC TCA GAA GAT GCT GAA CCT CTT GCT CCA   3195
Lys Ser Ser Ile Ala Gly Ser Glu Asp Ala Glu Pro Leu Ala Pro
            1055            1060            1065

CCC ATC AAA CCA ATT AAA CCT GTC ACT AGA AAC AAG GCA CCC CAG   3240
Pro Ile Lys Pro Ile Lys Pro Val Thr Arg Asn Lys Ala Pro Gln
            1070            1075            1080

GAA CCT CCA GTA AAG AAA GGA CGT CGA TCG AGG CGG TGT GGG CAG   3285
Glu Pro Pro Val Lys Lys Gly Arg Arg Ser Arg Arg Cys Gly Gln
            1085            1090            1095

TGT CCC GGC TGC CAG GTG CCT GAG GAC TGT GGT GTT TGT ACT AAT   3330
Cys Pro Gly Cys Gln Val Pro Glu Asp Cys Gly Val Cys Thr Asn
            1100            1105            1110

TGC TTA GAT AAG CCC AAG TTT GGT GGT CGC AAT ATA AAG AAG CAG   3375
Cys Leu Asp Lys Pro Lys Phe Gly Gly Arg Asn Ile Lys Lys Gln
            1115            1120            1125

TGC TGC AAG ATG AGA AAA TGT CAG AAT CTA CAA TGG ATG CCT TCC   3420
Cys Cys Lys Met Arg Lys Cys Gln Asn Leu Gln Trp Met Pro Ser
            1130            1135            1140

AAA GCC TAC CTG CAG AAG CAA GCT AAA GCT GTG AAA AAG AAA GAG   3465
Lys Ala Tyr Leu Gln Lys Gln Ala Lys Ala Val Lys Lys Lys Glu
            1145            1150            1155

AAA AAG TCT AAG ACC AGT GAA AAG AAA GAC AGC AAA GAG AGC AGT   3510
Lys Lys Ser Lys Thr Ser Glu Lys Lys Asp Ser Lys Glu Ser Ser
            1160            1165            1170

GTT GTG AAG AAC GTG GTG GAC TCT AGT CAG AAA CCT ACC CCA TCA   3555
Val Val Lys Asn Val Val Asp Ser Ser Gln Lys Pro Thr Pro Ser
            1175            1180            1185

GCA AGA GAG GAT CCT GCC CCA AAG AAA AGC AGT AGT GAG CCT CCT   3600
Ala Arg Glu Asp Pro Ala Pro Lys Lys Ser Ser Ser Glu Pro Pro
            1190            1195            1200

CCA CGA AAG CCC GTC GAG GAA AAG AGT GAA GAA GGG AAT GTC TCG   3645
Pro Arg Lys Pro Val Glu Glu Lys Ser Glu Glu Gly Asn Val Ser
            1205            1210            1215
```

```
GCC CCT GGG CCT GAA TCC AAA CAG GCC ACC ACT CCA GCT TCC AGG    3690
Ala Pro Gly Pro Glu Ser Lys Gln Ala Thr Thr Pro Ala Ser Arg
            1220                1225                1230

AAG TCA AGC AAG CAG GTC TCC CAG CCA GCA CTG GTC ATC CCG CCT    3735
Lys Ser Ser Lys Gln Val Ser Gln Pro Ala Leu Val Ile Pro Pro
            1235                1240                1245

CAG CCA CCT ACT ACA GGA CCG CCA AGA AAA GAA GTT CCC AAA ACC    3780
Gln Pro Pro Thr Thr Gly Pro Pro Arg Lys Glu Val Pro Lys Thr
            1250                1255                1260

ACT CCT AGT GAG CCC AAG AAA AAG CAG CCT CCA CCA CCA GAA TCA    3825
Thr Pro Ser Glu Pro Lys Lys Lys Gln Pro Pro Pro Pro Glu Ser
            1265                1270                1275

GGT CCA GAG CAG AGC AAA CAG AAA AAA GTG GCT CCC CGC CCA AGT    3870
Gly Pro Glu Gln Ser Lys Gln Lys Lys Val Ala Pro Arg Pro Ser
            1280                1285                1290

ATC CCT GTA AAA CAA AAA CCA AAA GAA AAG GAA AAA CCA CCT CCG    3915
Ile Pro Val Lys Gln Lys Pro Lys Glu Lys Glu Lys Pro Pro Pro
            1295                1300                1305

GTC AAT AAG CAG GAG AAT GCA GGC ACT TTG AAC ATC CTC AGC ACT    3960
Val Asn Lys Gln Glu Asn Ala Gly Thr Leu Asn Ile Leu Ser Thr
            1310                1315                1320

CTC TCC AAT GGC AAT AGT TCT AAG CAA AAA ATT CCA GCA GAT GGA    4005
Leu Ser Asn Gly Asn Ser Ser Lys Gln Lys Ile Pro Ala Asp Gly
            1325                1330                1335

GTC CAC AGG ATC AGA GTG GAC TTT AAG GAG GAT TGT GAA GCA GAA    4050
Val His Arg Ile Arg Val Asp Phe Lys Glu Asp Cys Glu Ala Glu
            1340                1345                1350

AAT GTG TGG GAG ATG GGA GGC TTA GGA ATC TTG ACT TCT GTT CCT    4095
Asn Val Trp Glu Met Gly Gly Leu Gly Ile Leu Thr Ser Val Pro
            1355                1360                1365

ATA ACA CCC AGG GTG GTT TGC TTT CTC TGT GCC AGT AGT GGG CAT    4140
Ile Thr Pro Arg Val Val Cys Phe Leu Cys Ala Ser Ser Gly His
            1370                1375                1380

GTA GAG TTT GTG TAT TGC CAA GTC TGT TGT GAG CCC TTC CAC AAG    4185
Val Glu Phe Val Tyr Cys Gln Val Cys Cys Glu Pro Phe His Lys
            1385                1390                1395

TTT TGT TTA GAG GAG AAC GAG CGC CCT CTG GAG GAC CAG CTG GAA    4230
Phe Cys Leu Glu Glu Asn Glu Arg Pro Leu Glu Asp Gln Leu Glu
            1400                1405                1410

AAT TGG TGT TGT CGT CGT TGC AAA TTC TGT CAC GTT TGT GGA AGG    4275
Asn Trp Cys Cys Arg Arg Cys Lys Phe Cys His Val Cys Gly Arg
            1415                1420                1425

CAA CAT CAG GCT ACA AAG CAG CTG CTG GAG TGT AAT AAG TGC CGA    4320
Gln His Gln Ala Thr Lys Gln Leu Leu Glu Cys Asn Lys Cys Arg
            1430                1435                1440

AAC AGC TAT CAC CCT GAG TGC CTG GGA CCA AAC TAC CCC ACC AAA    4365
Asn Ser Tyr His Pro Glu Cys Leu Gly Pro Asn Tyr Pro Thr Lys
            1445                1450                1455

CCC ACA AAG AAG AAG AAA GTC TGG ATC TGT ACC AAG TGT GTT CGC    4410
Pro Thr Lys Lys Lys Lys Val Trp Ile Cys Thr Lys Cys Val Arg
            1460                1465                1470

TGT AAG AGC TGT GGA TCC ACA ACT CCA GGC AAA GGG TGG GAT GCA    4455
Cys Lys Ser Cys Gly Ser Thr Thr Pro Gly Lys Gly Trp Asp Ala
            1475                1480                1485

CAG TGG TCT CAT GAT TTC TCA CTG TGT CAT GAT TGC GCC AAG CTC    4500
Gln Trp Ser His Asp Phe Ser Leu Cys His Asp Cys Ala Lys Leu
            1490                1495                1500

TTT GCT AAA GGA AAC TTC TGC CCT CTC TGT GAC AAA TGT TAT GAT    4545
Phe Ala Lys Gly Asn Phe Cys Pro Leu Cys Asp Lys Cys Tyr Asp
            1505                1510                1515
```

-continued

```
GAT GAT GAC TAT GAG AGT AAG ATG ATG CAA TGT GGA AAG TGT GAT  4590
Asp Asp Asp Tyr Glu Ser Lys Met Met Gln Cys Gly Lys Cys Asp
            1520            1525            1530

CGC TGG GTC CAT TCC AAA TGT GAG AAT CTT TCA GGT ACA GAA GAT  4635
Arg Trp Val His Ser Lys Cys Glu Asn Leu Ser Gly Thr Glu Asp
            1535            1540            1545

GAG ATG TAT GAG ATT CTA TCT AAT CTG CCA GAA AGT GTG GCC TAC  4680
Glu Met Tyr Glu Ile Leu Ser Asn Leu Pro Glu Ser Val Ala Tyr
            1550            1555            1560

ACT TGT GTG AAC TGT ACT GAG CGG CAC CCT GCA GAG TGG CGA CTG  4725
Thr Cys Val Asn Cys Thr Glu Arg His Pro Ala Glu Trp Arg Leu
            1565            1570            1575

GCC CTT GAA AAA GAG CTG CAG ATT TCT CTG AAG CAA GTT CTG ACA  4770
Ala Leu Glu Lys Glu Leu Gln Ile Ser Leu Lys Gln Val Leu Thr
            1580            1585            1590

GCT TTG TTG AAT TCT CGG ACT ACC AGC CAT TTG CTA CGC TAC CGG  4815
Ala Leu Leu Asn Ser Arg Thr Thr Ser His Leu Leu Arg Tyr Arg
            1595            1600            1605

CAG GCT GCC AAG CCT CCA GAC TTA AAT CCC GAG ACA GAG GAG AGT  4860
Gln Ala Ala Lys Pro Pro Asp Leu Asn Pro Glu Thr Glu Glu Ser
            1610            1615            1620

ATA CCT TCC CGC AGC TCC CCC GAA GGA CCT GAT CCA CCA GTT CTT  4905
Ile Pro Ser Arg Ser Ser Pro Glu Gly Pro Asp Pro Pro Val Leu
            1625            1630            1635

ACT GAG GTC AGC AAA CAG GAT GAT CAG CAG CCT TTA GAT CTA GAA  4950
Thr Glu Val Ser Lys Gln Asp Asp Gln Gln Pro Leu Asp Leu Glu
            1640            1645            1650

GGA GTC AAG AGG AAG ATG GAC CAA GGG AAT TAC ACA TCT GTG TTG  4995
Gly Val Lys Arg Lys Met Asp Gln Gly Asn Tyr Thr Ser Val Leu
            1655            1660            1665

GAG TTC AGT GAT GAT ATT GTG AAG ATC ATT CAA GCA GCC ATT AAT  5040
Glu Phe Ser Asp Asp Ile Val Lys Ile Ile Gln Ala Ala Ile Asn
            1670            1675            1680

TCA GAT GGA GGA CAG CCA GAA ATT AAA AAA GCC AAC AGC ATG GTC  5085
Ser Asp Gly Gly Gln Pro Glu Ile Lys Lys Ala Asn Ser Met Val
            1685            1690            1695

AAG TCC TTC TTC ATT CGG CAA ATG GAA CGT GTT TTT CCA TGG TTC  5130
Lys Ser Phe Phe Ile Arg Gln Met Glu Arg Val Phe Pro Trp Phe
            1700            1705            1710

AGT GTC AAA AAG TCC AGG TTT TGG GAG CCA AAT AAA GTA TCA AGC  5175
Ser Val Lys Lys Ser Arg Phe Trp Glu Pro Asn Lys Val Ser Ser
            1715            1720            1725

AAC AGT GGG ATG TTA CCA AAC GCA GTG CTT CCA CCT TCA CTT GAC  5220
Asn Ser Gly Met Leu Pro Asn Ala Val Leu Pro Pro Ser Leu Asp
            1730            1735            1740

CAT AAT TAT GCT CAG TGG CAG GAG CGA GAG GAA AAC AGC CAC ACT  5265
His Asn Tyr Ala Gln Trp Gln Glu Arg Glu Glu Asn Ser His Thr
            1745            1750            1755

GAG CAG CCT CCT TTA ATG AAG AAA ATC ATT CCA GCT CCC AAA CCC  5310
Glu Gln Pro Pro Leu Met Lys Lys Ile Ile Pro Ala Pro Lys Pro
            1760            1765            1770

AAA GGT CCT GGA GAA CCA GAC TCA CCA ACT CCT CTG CAT CCT CCT  5355
Lys Gly Pro Gly Glu Pro Asp Ser Pro Thr Pro Leu His Pro Pro
            1775            1780            1785

ACA CCA CCA ATT TTG AGT ACT GAT AGG AGT CGA GAA GAC AGT CCA  5400
Thr Pro Pro Ile Leu Ser Thr Asp Arg Ser Arg Glu Asp Ser Pro
            1790            1795            1800

GAG CTG AAC CCA CCC CCA GGC ATA GAA GAC AAT AGA CAG TGT GCG  5445
Glu Leu Asn Pro Pro Pro Gly Ile Glu Asp Asn Arg Gln Cys Ala
            1805            1810            1815
```

```
TTA TGT TTG ACT TAT GGT GAT GAC AGT GCT AAT GAT GCT GGT CGT  5490
Leu Cys Leu Thr Tyr Gly Asp Asp Ser Ala Asn Asp Ala Gly Arg
            1820                1825                1830

TTA CTA TAT ATT GGC CAA AAT GAG TGG ACA CAT GTA AAT TGT GCT  5535
Leu Leu Tyr Ile Gly Gln Asn Glu Trp Thr His Val Asn Cys Ala
            1835                1840                184

TTG TGG TCA GCG GAA GTG TTT GAA GAT GAT GAC GGA TCA CTA AAG  5580
Leu Trp Ser Ala Glu Val Phe Glu Asp Asp Asp Gly Ser Leu Lys
            1850                1855                1860

AAT GTG CAT ATG GCT GTG ATC AGG GGC AAG CAG CTG AGA TGT GAA  5625
Asn Val His Met Ala Val Ile Arg Gly Lys Gln Leu Arg Cys Glu
            1865                1870                1875

TTC TGC CAA AAG CCA GGA GCC ACC GTG GGT TGC TGT CTC ACA TCC  5670
Phe Cys Gln Lys Pro Gly Ala Thr Val Gly Cys Cys Leu Thr Ser
            1880                1885                1890

TGC ACC AGC AAC TAT CAC TTC ATG TGT TCC CGA GCC AAG AAC TGT  5715
Cys Thr Ser Asn Tyr His Phe Met Cys Ser Arg Ala Lys Asn Cys
            1895                1900                1905

GTC TTT CTG GAT GAT AAA AAA GTA TAT TGC CAA CGA CAT CGG GAT  5760
Val Phe Leu Asp Asp Lys Lys Val Tyr Cys Gln Arg His Arg Asp
            1910                1915                1920

TTG ATC AAA GGC GAA GTG GTT CCT GAG AAT GGA TTT GAA GTT TTC  5805
Leu Ile Lys Gly Glu Val Val Pro Glu Asn Gly Phe Glu Val Phe
            1925                1930                1935

AGA AGA GTG TTT GTG GAC TTT GAA GGA ATC AGC TTG AGA AGG AAG  5850
Arg Arg Val Phe Val Asp Phe Glu Gly Ile Ser Leu Arg Arg Lys
            1940                1945                1950

TTT CTC AAT GGC TTG GAA CCA GAA AAT ATC CAC ATG ATG ATT GGG  5895
Phe Leu Asn Gly Leu Glu Pro Glu Asn Ile His Met Met Ile Gly
            1955                1960                1965

TCT ATG ACA ATC GAC TGC TTA GGA ATT CTA AAT GAT CTC TCC GAC  5940
Ser Met Thr Ile Asp Cys Leu Gly Ile Leu Asn Asp Leu Ser Asp
            1970                1975                1980

TGT GAA GAT AAG CTC TTT CCT ATT GGA TAT CAG TGT TCC AGG GTA  5985
Cys Glu Asp Lys Leu Phe Pro Ile Gly Tyr Gln Cys Ser Arg Val
            1985                1990                1995

TAC TGG AGC ACC ACA GAT GCT CGC AAG CGC TGT GTA TAT ACA TGC  6030
Tyr Trp Ser Thr Thr Asp Ala Arg Lys Arg Cys Val Tyr Thr Cys
            2000                2005                2010

AAG ATA GTG GAG TGC CGT CCT CCA GTC GTA GAG CCG GAT ATC AAC  6075
Lys Ile Val Glu Cys Arg Pro Pro Val Val Glu Pro Asp Ile Asn
            2015                2020                2025

AGC ACT GTT GAA CAT GAT GAA AAC AGG ACC ATT GCC CAT AGT CCA  6120
Ser Thr Val Glu His Asp Glu Asn Arg Thr Ile Ala His Ser Pro
            2030                2035                2040

ACA TCT TTT ACA GAA AGT TCA TCA AAA GAG AGT CAA AAC ACA GCT  6165
Thr Ser Phe Thr Glu Ser Ser Ser Lys Glu Ser Gln Asn Thr Ala
            2045                2050                2055

GAA ATT ATA AGT CCT CCA TCA CCA GAC CGA CCT CCT CAT TCA CAA  6210
Glu Ile Ile Ser Pro Pro Ser Pro Asp Arg Pro Pro His Ser Gln
            2060                2065                2070

ACC TCT GGC TCC TGT TAT TAT CAT GTC ATC TCA AAG GTC CCC AGG  6255
Thr Ser Gly Ser Cys Tyr Tyr His Val Ile Ser Lys Val Pro Arg
            2075                2080                2085

ATT CGA ACA CCC AGT TAT TCT CCA ACA CAG AGA TCC CCT GGC TGT  6300
Ile Arg Thr Pro Ser Tyr Ser Pro Thr Gln Arg Ser Pro Gly Cys
            2090                2095                2100

CGA CCG TTG CCT TCT GCA GGA AGT CCT ACC CCA ACC ACT CAT GAA  6345
Arg Pro Leu Pro Ser Ala Gly Ser Pro Thr Pro Thr Thr His Glu
            2105                2110                2115
```

```
ATA GTC ACA GTA GGT GAT CCT TTA CTC TCC TCT GGA CTT CGA AGC    6390
Ile Val Thr Val Gly Asp Pro Leu Leu Ser Ser Gly Leu Arg Ser
            2120            2125            2130

ATT GGC TCC AGG CGT CAC AGT ACC TCT TCC TTA TCA CCC CAG CGG    6435
Ile Gly Ser Arg Arg His Ser Thr Ser Ser Leu Ser Pro Gln Arg
            2135            2140            2145

TCC AAA CTC CGG ATA ATG TCT CCA ATG AGA ACT GGG AAT ACT TAC    6480
Ser Lys Leu Arg Ile Met Ser Pro Met Arg Thr Gly Asn Thr Tyr
            2150            2155            2160

TCT AGG AAT AAT GTT TCC TCA GTC TCC ACC ACC GGG ACC GCT ACT    6525
Ser Arg Asn Asn Val Ser Ser Val Ser Thr Thr Gly Thr Ala Thr
            2165            2170            2175

GAT CTT GAA TCA AGT GCC AAA GTA GTT GAT CAT GTC TTA GGG CCA    6570
Asp Leu Glu Ser Ser Ala Lys Val Val Asp His Val Leu Gly Pro
            2180            2185            2190

CTG AAT TCA AGT ACT AGT TTA GGG CAA AAC ACT TCC ACC TCT TCA    6615
Leu Asn Ser Ser Thr Ser Leu Gly Gln Asn Thr Ser Thr Ser Ser
            2195            2200            2205

AAT TTG CAA AGG ACA GTG GTT ACT GTA GGC AAT AAA AAC AGT CAC    6660
Asn Leu Gln Arg Thr Val Val Thr Val Gly Asn Lys Asn Ser His
            2210            2215            2220

TTG GAT GGA TCT TCA TCT TCA GAA ATG AAG CAG TCC AGT GCT TCA    6705
Leu Asp Gly Ser Ser Ser Ser Glu Met Lys Gln Ser Ser Ala Ser
            2225            2230            2235

GAC TTG GTG TCC AAG AGC TCC TCT TTA AAG GGA GAG AAG ACC AAA    6750
Asp Leu Val Ser Lys Ser Ser Ser Leu Lys Gly Glu Lys Thr Lys
            2240            2245            2250

GTG CTG AGT TCC AAG AGC TCA GAG GGA TCT GCA CAT AAT GTG GCT    6795
Val Leu Ser Ser Lys Ser Ser Glu Gly Ser Ala His Asn Val Ala
            2255            2260            2265

TAC CCT GGA ATT CCT AAA CTG GCC CCA CAG GTT CAT AAC ACA ACA    6840
Tyr Pro Gly Ile Pro Lys Leu Ala Pro Gln Val His Asn Thr Thr
            2270            2275            2280

TCT AGA GAA CTG AAT GTT AGT AAA ATC GGC TCC TTT GCT GAA CCC    6885
Ser Arg Glu Leu Asn Val Ser Lys Ile Gly Ser Phe Ala Glu Pro
            2285            2290            2295

TCT TCA GTG TCG TTT TCT TCT AAA GAG GCC CTC TCC TTC CCA CAC    6930
Ser Ser Val Ser Phe Ser Ser Lys Glu Ala Leu Ser Phe Pro His
            2300            2305            2310

CTC CAT TTG AGA GGG CAA AGG AAT GAT CGA GAC CAA CAC ACA GAT    6975
Leu His Leu Arg Gly Gln Arg Asn Asp Arg Asp Gln His Thr Asp
            2315            2320            2325

TCT ACC CAA TCA GCA AAC TCC TCT CCA GAT GAA GAT ACT GAA GTC    7020
Ser Thr Gln Ser Ala Asn Ser Ser Pro Asp Glu Asp Thr Glu Val
            2330            2335            2340

AAA ACC TTG AAG CTA TCT GGA ATG AGC AAC AGA TCA TCC ATT ATC    7065
Lys Thr Leu Lys Leu Ser Gly Met Ser Asn Arg Ser Ser Ile Ile
            2345            2350            2355

AAC GAA CAT ATG GGA TCT AGT TCC AGA GAT AGG AGA CAG AAA GGG    7110
Asn Glu His Met Gly Ser Ser Ser Arg Asp Arg Arg Gln Lys Gly
            2360            2365            2370

AAA AAA TCC TGT AAA GAA ACT TTC AAA GAA AAG CAT TCC AGT AAA    7155
Lys Lys Ser Cys Lys Glu Thr Phe Lys Glu Lys His Ser Ser Lys
            2375            2380            2385

TCT TTT TTG GAA CCT GGT CAG GTG ACA ACT GGT GAG GAA GGA AAC    7200
Ser Phe Leu Glu Pro Gly Gln Val Thr Thr Gly Glu Glu Gly Asn
            2390            2395            2400

TTG AAG CCA GAG TTT ATG GAT GAG GTT TTG ACT CCT GAG TAT ATG    7245
Leu Lys Pro Glu Phe Met Asp Glu Val Leu Thr Pro Glu Tyr Met
            2405            2410            2415
```

```
GGC CAA CGA CCA TGT AAC AAT GTT TCT TCT GAT AAG ATT GGT GAT    7290
Gly Gln Arg Pro Cys Asn Asn Val Ser Ser Asp Lys Ile Gly Asp
            2420                2425                2430

AAA GGC CTT TCT ATG CCA GGA GTC CCC AAA GCT CCA CCC ATG CAA    7335
Lys Gly Leu Ser Met Pro Gly Val Pro Lys Ala Pro Pro Met Gln
            2435                2440                2445

GTA GAA GGA TCT GCC AAG GAA TTA CAG GCA CCA CGG AAA CGC ACA    7380
Val Glu Gly Ser Ala Lys Glu Leu Gln Ala Pro Arg Lys Arg Thr
            2450                2455                2460

GTC AAA GTG ACA CTG ACA CCT CTA AAA ATG GAA AAT GAG AGT CAA    7425
Val Lys Val Thr Leu Thr Pro Leu Lys Met Glu Asn Glu Ser Gln
            2465                2470                2475

TCC AAA AAT GCC CTG AAA GAA AGT AGT CCT GCT TCC CCT TTG CAA    7470
Ser Lys Asn Ala Leu Lys Glu Ser Ser Pro Ala Ser Pro Leu Gln
            2480                2485                2490

ATA GAG TCA ACA TCT CCC ACA GAA CCA ATT TCA GCC TCT GAA AAT    7515
Ile Glu Ser Thr Ser Pro Thr Glu Pro Ile Ser Ala Ser Glu Asn
            2495                2500                2505

CCA GGA GAT GGT CCA GTG GCC CAA CCA AGC CCC AAT AAT ACC TCA    7560
Pro Gly Asp Gly Pro Val Ala Gln Pro Ser Pro Asn Asn Thr Ser
            2510                2515                2520

TGC CAG GAT TCT CAA AGT AAC AAC TAT CAG AAT CTT CCA GTA CAG    7605
Cys Gln Asp Ser Gln Ser Asn Asn Tyr Gln Asn Leu Pro Val Gln
            2525                2530                2535

GAC AGA AAC CTA ATG CTT CCA GAT GGC CCC AAA CCT CAG GAG GAT    7650
Asp Arg Asn Leu Met Leu Pro Asp Gly Pro Lys Pro Gln Glu Asp
            2540                2545                2550

GGC TCT TTT AAA AGG AGG TAT CCC CGT CGC AGT GCC CGT GCA CGT    7695
Gly Ser Phe Lys Arg Arg Tyr Pro Arg Arg Ser Ala Arg Ala Arg
            2555                2560                2565

TCT AAC ATG TTT TTT GGG CTT ACC CCA CTC TAT GGA GTA AGA TCC    7740
Ser Asn Met Phe Phe Gly Leu Thr Pro Leu Tyr Gly Val Arg Ser
            2570                2575                2580

TAT GGT GAA GAA GAC ATT CCA TTC TAC AGC AGC TCA ACT GGG AAG    7785
Tyr Gly Glu Glu Asp Ile Pro Phe Tyr Ser Ser Ser Thr Gly Lys
            2585                2590                2595

AAG CGA GGC AAG AGA TCA GCT GAA GGA CAG GTG GAT GGG GCC GAT    7830
Lys Arg Gly Lys Arg Ser Ala Glu Gly Gln Val Asp Gly Ala Asp
            2600                2605                2610

GAC TTA AGC ACT TCA GAT GAA GAC GAC TTA TAC TAT TAC AAC TTC    7875
Asp Leu Ser Thr Ser Asp Glu Asp Asp Leu Tyr Tyr Tyr Asn Phe
            2615                2620                2625

ACT AGA ACA GTG ATT TCT TCA GGT GGA GAG GAA CGA CTG GCA TCC    7920
Thr Arg Thr Val Ile Ser Ser Gly Gly Glu Glu Arg Leu Ala Ser
            2630                2635                2640

CAT AAT TTA TTT CGG GAG GAG GAA CAG TGT GAT CTT CCA AAA ATC    7965
His Asn Leu Phe Arg Glu Glu Glu Gln Cys Asp Leu Pro Lys Ile
            2645                2650                2655

TCA CAG TTG GAT GGT GTT GAT GAT GGG ACA GAG AGT GAT ACT AGT    8010
Ser Gln Leu Asp Gly Val Asp Asp Gly Thr Glu Ser Asp Thr Ser
            2660                2665                2670

GTC ACA GCC ACA ACA AGG AAA AGC AGC CAG ATT CCA AAA AGA AAT    8055
Val Thr Ala Thr Thr Arg Lys Ser Ser Gln Ile Pro Lys Arg Asn
            2675                2680                2685

GGT AAA GAA AAT GGA ACA GAG AAC TTA AAG ATT GAT AGA CCT GAA    8100
Gly Lys Glu Asn Gly Thr Glu Asn Leu Lys Ile Asp Arg Pro Glu
            2690                2695                2700

GAT GCT GGG GAG AAA GAA CAT GTC ACT AAG AGT TCT GTT GGC CAC    8145
Asp Ala Gly Glu Lys Glu His Val Thr Lys Ser Ser Val Gly His
            2705                2710                2715
```

```
AAA AAT GAG CCA AAG ATG GAT AAC TGC CAT TCT GTA AGC AGA GTT     8190
Lys Asn Glu Pro Lys Met Asp Asn Cys His Ser Val Ser Arg Val
                2720            2725            2730

AAA ACA CAG GGA CAA GAT TCC TTG GAA GCT CAG CTC AGC TCA TTG     8235
Lys Thr Gln Gly Gln Asp Ser Leu Glu Ala Gln Leu Ser Ser Leu
                2735            2740            2745

GAG TCA AGC CGC AGA GTC CAC ACA AGT ACC CCC TCC GAC AAA AAT     8280
Glu Ser Ser Arg Arg Val His Thr Ser Thr Pro Ser Asp Lys Asn
                2750            2755            2760

TTA CTG GAC ACC TAT AAT ACT GAG CTC CTG AAA TCA GAT TCA GAC     8325
Leu Leu Asp Thr Tyr Asn Thr Glu Leu Leu Lys Ser Asp Ser Asp
                2765            2770            2775

AAT AAC AAC AGT GAT GAC TGT GGG AAT ATC CTG CCT TCA GAC ATT     8370
Asn Asn Asn Ser Asp Asp Cys Gly Asn Ile Leu Pro Ser Asp Ile
                2780            2785            2790

ATG GAC TTT GTA CTA AAG AAT ACT CCA TCC ATG CAG GCT TTG GGT     8415
Met Asp Phe Val Leu Lys Asn Thr Pro Ser Met Gln Ala Leu Gly
                2795            2800            2805

GAG AGC CCA GAG TCA TCT TCA TCA GAA CTC CTG AAT CTT GGT GAA     8460
Glu Ser Pro Glu Ser Ser Ser Ser Glu Leu Leu Asn Leu Gly Glu
                2810            2815            2820

GGA TTG GGT CTT GAC AGT AAT CGT GAA AAA GAC ATG GGT CTT TTT     8505
Gly Leu Gly Leu Asp Ser Asn Arg Glu Lys Asp Met Gly Leu Phe
                2825            2830            2835

GAA GTA TTT TCT CAG CAG CTG CCT ACA ACA GAA CCT GTG GAT AGT     8550
Glu Val Phe Ser Gln Gln Leu Pro Thr Thr Glu Pro Val Asp Ser
                2840            2845            2850

AGT GTC TCT TCC TCT ATC TCA GCA GAG GAA CAG TTT GAG TTG CCT     8595
Ser Val Ser Ser Ser Ile Ser Ala Glu Glu Gln Phe Glu Leu Pro
                2855            2860            2865

CTA GAG CTA CCA TCT GAT CTG TCT GTC TTG ACC ACC CGG AGT CCC     8640
Leu Glu Leu Pro Ser Asp Leu Ser Val Leu Thr Thr Arg Ser Pro
                2870            2875            2880

ACT GTC CCC AGC CAG AAT CCC AGT AGA CTA GCT GTT ATC TCA GAC     8685
Thr Val Pro Ser Gln Asn Pro Ser Arg Leu Ala Val Ile Ser Asp
                2885            2990            2895

TCA GGG GAG AAG AGA GTA ACC ATC ACA GAA AAA TCT GTA GCC TCC     8730
Ser Gly Glu Lys Arg Val Thr Ile Thr Glu Lys Ser Val Ala Ser
                2900            2905            2910

TCT GAA AGT GAC CCA GCA CTG CTG AGC CCA GGA GTA GAT CCA ACT     8775
Ser Glu Ser Asp Pro Ala Leu Leu Ser Pro Gly Val Asp Pro Thr
                2915            2920            2925

CCT GAA GGC CAC ATG ACT CCT GAT CAT TTT ATC CAA GGA CAC ATG     8820
Pro Glu Gly His Met Thr Pro Asp His Phe Ile Gln Gly His Met
                2930            2935            2940

GAT GCA GAC CAC ATC TCT AGC CCT CCT TGT GGT TCA GTA GAG CAA     8865
Asp Ala Asp His Ile Ser Ser Pro Pro Cys Gly Ser Val Glu Gln
                2945            2950            2955

GGT CAT GGC AAC AAT CAG GAT TTA ACT AGG AAC AGT AGC ACC CCT     8910
Gly His Gly Asn Asn Gln Asp Leu Thr Arg Asn Ser Ser Thr Pro
                2960            2965            2970

GGC CTT CAG GTA CCT GTT TCC CCA ACT GTT CCC ATC CAG AAC CAG     8955
Gly Leu Gln Val Pro Val Ser Pro Thr Val Pro Ile Gln Asn Gln
                2975            2980            2985

AAG TAT GTG CCC AAT TCT ACT GAT AGT CCT GGC CCG TCT CAG ATT     9000
Lys Tyr Val Pro Asn Ser Thr Asp Ser Pro Gly Pro Ser Gln Ile
                2990            2995            3000

TCC AAT GCA GCT GTC CAG ACC ACT CCA CCC CAC CTG AAG CCA GCC     9045
Ser Asn Ala Ala Val Gln Thr Thr Pro Pro His Leu Lys Pro Ala
                3005            3010            3015
```

```
ACT GAG AAA CTC ATA GTT GTT AAC CAG AAC ATG CAG CCA CTT TAT      9090
Thr Glu Lys Leu Ile Val Val Asn Gln Asn Met Gln Pro Leu Tyr
                3020            3025                3030

GTT CTC CAA ACT CTT CCA AAT GGA GTG ACC CAA AAA ATC CAA TTG      9135
Val Leu Gln Thr Leu Pro Asn Gly Val Thr Gln Lys Ile Gln Leu
                3035            3040                3045

ACC TCT TCT GTT AGT TCT ACA CCC AGT GTG ATG GAG ACA AAT ACT      9180
Thr Ser Ser Val Ser Ser Thr Pro Ser Val Met Glu Thr Asn Thr
                3050            3055                3060

TCA GTA TTG GGA CCC ATG GGA GGT GGT CTC ACC CTT ACC ACA GGA      9225
Ser Val Leu Gly Pro Met Gly Gly Gly Leu Thr Leu Thr Thr Gly
                3065            3070                3075

CTA AAT CCA AGC TTG CCA ACT TCT CAA TCT TTG TTC CCT TCT GCT      9270
Leu Asn Pro Ser Leu Pro Thr Ser Gln Ser Leu Phe Pro Ser Ala
                3080            3085                3090

AGC AAA GGA TTG CTA CCC ATG TCT CAT CAC CAG CAC TTA CAT TCC      9315
Ser Lys Gly Leu Leu Pro Met Ser His His Gln His Leu His Ser
                3095            3100                3105

TTC CCT GCA GCT ACT CAA AGT AGT TTC CCA CCA AAC ATC AGC AAT      9360
Phe Pro Ala Ala Thr Gln Ser Ser Phe Pro Pro Asn Ile Ser Asn
                3110            3115                3120

CCT CCT TCA GGC CTG CTT ATT GGG GTT CAG CCT CCT CCG GAT CCC      9405
Pro Pro Ser Gly Leu Leu Ile Gly Val Gln Pro Pro Pro Asp Pro
                3125            3130                3135

CAA CTT TTG GTT TCA GAA TCC AGC CAG AGG ACA GAC CTC AGT ACC      9450
Gln Leu Leu Val Ser Glu Ser Ser Gln Arg Thr Asp Leu Ser Thr
                3140            3145                3150

ACA GTA GCC ACT CCA TCC TCT GGA CTC AAG AAA AGA CCC ATA TCT      9495
Thr Val Ala Thr Pro Ser Ser Gly Leu Lys Lys Arg Pro Ile Ser
                3155            3160                3165

CGT CTA CAG ACC CGA AAG AAT AAA AAA CTT GCT CCC TCT AGT ACC      9540
Arg Leu Gln Thr Arg Lys Asn Lys Lys Leu Ala Pro Ser Ser Thr
                3170            3175                3180

CCT TCA AAC ATT GCC CCT TCT GAT GTG GTT TCT AAT ATG ACA TTG      9585
Pro Ser Asn Ile Ala Pro Ser Asp Val Val Ser Asn Met Thr Leu
                3185            3190                3195

ATT AAC TTC ACA CCC TCC CAG CTT CCT AAT CAT CCA AGT CTG TTA      9630
Ile Asn Phe Thr Pro Ser Gln Leu Pro Asn His Pro Ser Leu Leu
                3200            3205                3210

GAT TTG GGG TCA CTT AAT ACT TCA TCT CAC CGA ACT GTC CCC AAC      9675
Asp Leu Gly Ser Leu Asn Thr Ser Ser His Arg Thr Val Pro Asn
                3215            3220                3225

ATC ATA AAA AGA TCT AAA TCT AGC ATC ATG TAT TTT GAA CCG GCA      9720
Ile Ile Lys Arg Ser Lys Ser Ser Ile Met Tyr Phe Glu Pro Ala
                3230            3235                3240

CCC CTG TTA CCA CAG AGT GTG GGA GGA ACT GCT GCC ACA GCG GCA      9765
Pro Leu Leu Pro Gln Ser Val Gly Gly Thr Ala Ala Thr Ala Ala
                3245            3250                3255

GGC ACA TCA ACA ATA AGC CAG GAT ACT AGC CAC CTC ACA TCA GGG      9810
Gly Thr Ser Thr Ile Ser Gln Asp Thr Ser His Leu Thr Ser Gly
                3260            3265                3270

TCT GTG TCT GGC TTG GCA TCC AGT TCC TCT GTC TTG AAT GTT GTA      9855
Ser Val Ser Gly Leu Ala Ser Ser Ser Ser Val Leu Asn Val Val
                3275            3280                3285

TCC ATG CAA ACT ACC ACA ACC CCT ACA AGT AGT GCG TCA GTT CCA      9900
Ser Met Gln Thr Thr Thr Thr Pro Thr Ser Ser Ala Ser Val Pro
                3290            3295                3300

GGA CAC GTC ACC TTA ACC AAC CCA AGG TTG CTT GGT ACC CCA GAT      9945
Gly His Val Thr Leu Thr Asn Pro Arg Leu Leu Gly Thr Pro Asp
                3305            3310                3315
```

-continued

| | | | | | | | | | | | | | | | |
|---|---|---|---|---|---|---|---|---|---|---|---|---|---|---|---|
| ATT | GGC | TCA | ATA | AGC | AAT | CTT | TTA | ATC | AAA | GCT | AGC | CAG | CAG | AGC | 9990 |
| Ile | Gly | Ser | Ile | Ser | Asn | Leu | Leu | Ile | Lys | Ala | Ser | Gln | Gln | Ser | |
| | | | | 3320 | | | | 3325 | | | | | | 3330 | |
| CTG | GGG | ATT | CAG | GAC | CAG | CCT | GTG | GCT | TTA | CCG | CCA | AGT | TCA | GGA | 10035 |
| Leu | Gly | Ile | Gln | Asp | Gln | Pro | Val | Ala | Leu | Pro | Pro | Ser | Ser | Gly | |
| | | | | 3335 | | | | 3340 | | | | | | 3345 | |
| ATG | TTT | CCA | CAA | CTG | GGG | ACA | TCA | CAG | ACC | CCC | TCT | ACT | GCT | GCA | 10080 |
| Met | Phe | Pro | Gln | Leu | Gly | Thr | Ser | Gln | Thr | Pro | Ser | Thr | Ala | Ala | |
| | | | | 3350 | | | | 3355 | | | | | | 3360 | |
| ATA | ACA | GCG | GCA | TCT | AGC | ATC | TGT | GTG | CTC | CCC | TCC | ACT | CAG | ACT | 10125 |
| Ile | Thr | Ala | Ala | Ser | Ser | Ile | Cys | Val | Leu | Pro | Ser | Thr | Gln | Thr | |
| | | | | 3365 | | | | 3370 | | | | | | 3375 | |
| ACG | GGC | ATA | ACA | GCC | GCT | TCA | CCT | TCT | GGG | GAA | GCA | GAC | GAA | CAC | 10170 |
| Thr | Gly | Ile | Thr | Ala | Ala | Ser | Pro | Ser | Gly | Glu | Ala | Asp | Glu | His | |
| | | | | 3380 | | | | 3385 | | | | | | 3390 | |
| TAT | CAG | CTT | CAG | CAT | GTG | AAC | CAG | CTC | CTT | GCC | AGC | AAA | ACT | GGG | 10215 |
| Tyr | Gln | Leu | Gln | His | Val | Asn | Gln | Leu | Leu | Ala | Ser | Lys | Thr | Gly | |
| | | | | 3395 | | | | 3400 | | | | | | 3405 | |
| ATT | CAT | TCT | TCC | CAG | CGT | GAT | CTT | GAT | TCT | GCT | TCA | GGG | CCC | CAG | 10260 |
| Ile | His | Ser | Ser | Gln | Arg | Asp | Leu | Asp | Ser | Ala | Ser | Gly | Pro | Gln | |
| | | | | 3410 | | | | 3415 | | | | | | 3420 | |
| GTA | TCC | AAC | TTT | ACC | CAG | ACG | GTA | GAC | GCT | CCT | AAT | AGC | ATG | GGA | 10305 |
| Val | Ser | Asn | Phe | Thr | Gln | Thr | Val | Asp | Ala | Pro | Asn | Ser | Met | Gly | |
| | | | | 3425 | | | | 3430 | | | | | | 3435 | |
| CTG | GAG | CAG | AAC | AAG | GCT | TTA | TCC | TCA | GCT | GTG | CAA | GCC | AGC | CCC | 10350 |
| Leu | Glu | Gln | Asn | Lys | Ala | Leu | Ser | Ser | Ala | Val | Gln | Ala | Ser | Pro | |
| | | | | 3440 | | | | 3445 | | | | | | 3450 | |
| ACC | TCT | CCT | GGG | GGT | TCT | CCA | TCC | TCT | CCA | TCT | TCT | GGA | CAG | CGG | 10395 |
| Thr | Ser | Pro | Gly | Gly | Ser | Pro | Ser | Ser | Pro | Ser | Ser | Gly | Gln | Arg | |
| | | | | 3455 | | | | 3460 | | | | | | 3465 | |
| TCA | GCA | AGC | CCT | TCA | GTG | CCG | GGT | CCC | ACT | AAA | CCC | AAA | CCA | AAA | 10440 |
| Ser | Ala | Ser | Pro | Ser | Val | Pro | Gly | Pro | Thr | Lys | Pro | Lys | Pro | Lys | |
| | | | | 3470 | | | | 3475 | | | | | | 3480 | |
| ACC | AAA | CGG | TTT | CAG | CTG | CCT | CTA | GAC | AAA | GGG | AAT | GGC | AAG | AAG | 10485 |
| Thr | Lys | Arg | Phe | Gln | Leu | Pro | Leu | Asp | Lys | Gly | Asn | Gly | Lys | Lys | |
| | | | | 3485 | | | | 3490 | | | | | | 3495 | |
| CAC | AAT | GTT | TCC | CAT | TTG | CGG | ACC | AGT | TCT | TCT | GAA | GCA | CAC | ATT | 10530 |
| His | Asn | Val | Ser | His | Leu | Arg | Thr | Ser | Ser | Ser | Glu | Ala | His | Ile | |
| | | | | 3500 | | | | 3505 | | | | | | 3510 | |
| CCA | GAC | CAA | GAA | ACG | ACA | TCC | CTG | ACC | TCA | GGC | ACA | GGG | ACT | CCA | 10575 |
| Pro | Asp | Gln | Glu | Thr | Thr | Ser | Leu | Thr | Ser | Gly | Thr | Gly | Thr | Pro | |
| | | | | 3515 | | | | 3520 | | | | | | 3525 | |
| GGA | GCA | GAG | GCT | GAG | CAG | CAG | GAT | ACA | GCT | AGC | GTG | GAG | CAG | TCC | 10620 |
| Gly | Ala | Glu | Ala | Glu | Gln | Gln | Asp | Thr | Ala | Ser | Val | Glu | Gln | Ser | |
| | | | | 3530 | | | | 3535 | | | | | | 3540 | |
| TCC | CAG | AAG | GAG | TGT | GGG | CAA | CCT | GCA | GGG | CAA | GTC | GCT | GTT | CTT | 10665 |
| Ser | Gln | Lys | Glu | Cys | Gly | Gln | Pro | Ala | Gly | Gln | Val | Ala | Val | Leu | |
| | | | | 3545 | | | | 3550 | | | | | | 3555 | |
| CCG | GAA | GTT | CAG | GTG | ACC | CAA | AAT | CCA | GCA | AAT | GAA | CAA | GAA | AGT | 10710 |
| Pro | Glu | Val | Gln | Val | Thr | Gln | Asn | Pro | Ala | Asn | Glu | Gln | Glu | Ser | |
| | | | | 3560 | | | | 3565 | | | | | | 3570 | |
| GCA | GAA | CCT | AAA | ACA | GTG | GAA | GAA | GAG | GAA | AGT | AAT | TTC | AGC | TCC | 10755 |
| Ala | Glu | Pro | Lys | Thr | Val | Glu | Glu | Glu | Glu | Ser | Asn | Phe | Ser | Ser | |
| | | | | 3575 | | | | 3580 | | | | | | 3585 | |
| CCA | CTG | ATG | CTT | TGG | CTT | CAG | CAA | GAA | CAA | AAG | CGG | AAG | GAA | AGC | 10800 |
| Pro | Leu | Met | Leu | Trp | Leu | Gln | Gln | Glu | Gln | Lys | Arg | Lys | Glu | Ser | |
| | | | | 3590 | | | | 3595 | | | | | | 3600 | |
| ATT | ACT | GAG | AAA | AAA | CCC | AAG | AAA | GGA | CTT | GTT | TTT | GAA | ATT | TCC | 10845 |
| Ile | Thr | Glu | Lys | Lys | Pro | Lys | Lys | Gly | Leu | Val | Phe | Glu | Ile | Ser | |
| | | | | 3605 | | | | 3610 | | | | | | 3615 | |

| | | | | | | | | | | | | | | | |
|---|---|---|---|---|---|---|---|---|---|---|---|---|---|---|---|
| AGT | GAT | GAT | GGC | TTT | CAG | ATC | TGT | GCA | GAA | AGT | ATT | GAA | GAT | GCC | 10890 |
| Ser | Asp | Asp | Gly | Phe | Gln | Ile | Cys | Ala | Glu | Ser | Ile | Glu | Asp | Ala | |
| | | | 3620 | | | | | 3625 | | | | | | 3530 | |
| TGG | AAG | TCA | TTG | ACA | GAT | AAA | GTC | CAG | GAA | GCT | CGA | TCA | AAT | GCC | 10935 |
| Trp | Lys | Ser | Leu | Thr | Asp | Lys | Val | Gln | Glu | Ala | Arg | Ser | Asn | Ala | |
| | | | 3535 | | | | | 3540 | | | | | | 3545 | |
| CGC | CTA | AAG | CAG | CTC | TCA | TTT | GCA | GGT | GTT | AAC | GGT | TTG | AGG | ATG | 10980 |
| Arg | Leu | Lys | Gln | Leu | Ser | Phe | Ala | Gly | Val | Asn | Gly | Leu | Arg | Met | |
| | | | 3550 | | | | | 3555 | | | | | | 3560 | |
| CTG | GGG | ATT | CTC | CAT | GAT | GCA | GTT | GTG | TTC | CTC | ATT | GAG | CAG | CTG | 11025 |
| Leu | Gly | Ile | Leu | His | Asp | Ala | Val | Val | Phe | Leu | Ile | Glu | Gln | Leu | |
| | | | 3565 | | | | | 3570 | | | | | | 3575 | |
| TCT | GGT | GCC | AAG | CAC | TGT | CGA | AAT | TAC | AAA | TTC | CGT | TTC | CAC | AAG | 11070 |
| Ser | Gly | Ala | Lys | His | Cys | Arg | Asn | Tyr | Lys | Phe | Arg | Phe | His | Lys | |
| | | | 3580 | | | | | 3585 | | | | | | 3590 | |
| CCA | GAG | GAG | GCC | AAT | GAA | CCC | CCC | TTG | AAC | CCT | CAC | GGC | TCA | GCC | 11115 |
| Pro | Glu | Glu | Ala | Asn | Glu | Pro | Pro | Leu | Asn | Pro | His | Gly | Ser | Ala | |
| | | | 3595 | | | | | 3600 | | | | | | 3605 | |
| AGG | GCT | GAA | GTC | CAC | CTC | AGG | AAG | TCA | GCA | TTT | GAC | ATG | TTT | AAC | 11160 |
| Arg | Ala | Glu | Val | His | Leu | Arg | Lys | Ser | Ala | Phe | Asp | Met | Phe | Asn | |
| | | | 3610 | | | | | 3615 | | | | | | 3620 | |
| TTC | CTG | GCT | TCT | AAA | CAT | CGT | CAG | CCT | CCT | GAA | TAC | AAC | CCC | AAT | 11205 |
| Phe | Leu | Ala | Ser | Lys | His | Arg | Gln | Pro | Pro | Glu | Tyr | Asn | Pro | Asn | |
| | | | 3625 | | | | | 3630 | | | | | | 3635 | |
| GAT | GAA | GAA | GAG | GAG | GAG | GTA | CAG | CTG | AAG | TCA | GCT | CGG | AGG | GCA | 11250 |
| Asp | Glu | Glu | Glu | Glu | Glu | Val | Gln | Leu | Lys | Ser | Ala | Arg | Arg | Ala | |
| | | | 3640 | | | | | 3645 | | | | | | 3650 | |
| ACT | AGC | ATG | GAT | CTG | CCA | ATG | CCC | ATG | CGC | TTC | CGG | CAC | TTA | AAA | 11295 |
| Thr | Ser | Met | Asp | Leu | Pro | Met | Pro | Met | Arg | Phe | Arg | His | Leu | Lys | |
| | | | 3655 | | | | | 3660 | | | | | | 3665 | |
| AAG | ACT | TCT | AAG | GAG | GCA | GTT | GGT | GTC | TAC | AGG | TCT | CCC | ATC | CAT | 11340 |
| Lys | Thr | Ser | Lys | Glu | Ala | Val | Gly | Val | Tyr | Arg | Ser | Pro | Ile | His | |
| | | | 3670 | | | | | 3675 | | | | | | 3680 | |
| GGC | CGG | GGT | CTT | TTC | TGT | AAG | AGA | AAC | ATT | GAT | GCA | GGT | GAG | ATG | 11385 |
| Gly | Arg | Gly | Leu | Phe | Cys | Lys | Arg | Asn | Ile | Asp | Ala | Gly | Glu | Met | |
| | | | 3685 | | | | | 3690 | | | | | | 3695 | |
| GTG | ATT | GAG | TAT | GCC | GGC | AAC | GTC | ATC | CGC | TCC | ATC | CAG | ACT | GAC | 11430 |
| Val | Ile | Glu | Tyr | Ala | Gly | Asn | Val | Ile | Arg | Ser | Ile | Gln | Thr | Asp | |
| | | | 3700 | | | | | 3705 | | | | | | 3710 | |
| AAG | CGG | GAA | AAG | TAT | TAC | GAC | AGC | AAG | GGC | ATT | GGT | TGC | TAT | ATG | 11475 |
| Lys | Arg | Glu | Lys | Tyr | Tyr | Asp | Ser | Lys | Gly | Ile | Gly | Cys | Tyr | Met | |
| | | | 3715 | | | | | 3720 | | | | | | 3725 | |
| TTC | CGA | ATT | GAT | GAC | TCA | GAG | GTA | GTG | GAT | GCC | ACC | ATG | CAT | GGA | 11520 |
| Phe | Arg | Ile | Asp | Asp | Ser | Glu | Val | Val | Asp | Ala | Thr | Met | His | Gly | |
| | | | 3730 | | | | | 3735 | | | | | | 3740 | |
| AAT | GCT | GCA | CGC | TTC | ATC | AAT | CAC | TCG | TGT | GAG | CCT | AAC | TGC | TAT | 11565 |
| Asn | Ala | Ala | Arg | Phe | Ile | Asn | His | Ser | Cys | Glu | Pro | Asn | Cys | Tyr | |
| | | | 3745 | | | | | 3750 | | | | | | 3755 | |
| TCT | CGG | GTC | ATC | AAT | ATT | GAT | GGG | CAG | AAG | CAC | ATT | GTC | ATC | TTT | 11610 |
| Ser | Arg | Val | Ile | Asn | Ile | Asp | Gly | Gln | Lys | His | Ile | Val | Ile | Phe | |
| | | | 3760 | | | | | 3765 | | | | | | 3770 | |
| GCC | ATG | CGT | AAG | ATC | TAC | CGA | GGA | GAG | GAA | CTC | ACT | TAC | GAC | TAT | 11655 |
| Ala | Met | Arg | Lys | Ile | Tyr | Arg | Gly | Glu | Glu | Leu | Thr | Tyr | Asp | Tyr | |
| | | | 3775 | | | | | 3780 | | | | | | 3785 | |
| AAG | TTC | CCC | ATT | GAG | GAT | GCC | AGC | AAC | AAG | CTG | CCC | TGC | AAC | TGT | 11700 |
| Lys | Phe | Pro | Ile | Glu | Asp | Ala | Ser | Asn | Lys | Leu | Pro | Cys | Asn | Cys | |
| | | | 3790 | | | | | 3795 | | | | | | 3800 | |
| GGC | GCC | AAG | AAA | TGC | CGG | AAG | TTC | CTA | AAC | TAA | AGC | TGC | TCT | TCT | 11745 |
| Gly | Ala | Lys | Lys | Cys | Arg | Lys | Phe | Leu | Asn | | | | | | |
| | | | 3805 | | | | | 3810 | | | | | | | |

```
CCCCCAGTGT  TGGAGTGCAA  GGAGGCGGGG  CCATCCAAAG  CAACG            11790
CTGAAGGCCT  TTTCCAGCAG  CTGGGAGCTC  CCGGATTGCG  TGGCACAGCT       11840
GAGGGGCCTC  TGTGATGGCT  GAGCTCTCTT  ATGTCCTATA  CTCACATCAG       11890
ACATGTGATC  ATAGTCCCAG  AGACAGAGTT  GAGGTCTCGA  AGAAAAGATC       11940
CATGATCGGC  TTTCTCCTGG  GGCCCCTCCA  ATTGTTTACT  GTTAGAAAGT       11990
GGGAATGGGG  TCCCTAGCAG  ACTTGCCTGG  AAGGAGCCTA  TTATAGAGGG       12040
TTGGTTATGT  TGGGAGATTG  GGCCTGAATT  TCTCCACAGA  AATAAGTTGC       12090
CATCCTCAGG  TTGGCCCTTT  CCCAAGCACT  GTAAGTGAGT  GGGTCAGCCA       12140
AAGCCCCAAA  TGGAGGGTTG  GTTAGATTCC  TGACAGTTTG  CCAGCCAGCC       12190
GCCACCTACA  GCGTCTGTCG  AACAAACAGA  GGTCTGGTGG  TTTTCCCTAC       12240
TGTCCTCCCA  CTCGAGAGTT  CACTTCTGGT  TGGGAGACAG  GATTCCTAGC       12290
ACCTCCGGTG  TCAAAAGGCT  GTCATGGGGT  TGTGCCAATT  AATTACCAAA       12340
CATTGAGCCT  GCAGGCTTTG  AGTGGGAGTG  TTGCCCCAG   GAGCCTTATC       12390
TCAGCCAATT  ACCTTTCTTG  ACAGTAGGAG  CGGCTTCCCT  CTCCCATTCC       12440
CTCTTCACTC  CCTTTTCTTC  CTTTCCCCTG  TCTTCATGCC  ACTGCTTTCC       12490
CATGCTTCTT  TCGGTTGTAG  GGGAGACTGA  CTGCCTGCTC  AAGGACACTC       12540
CCTGCTGGGC  ATAGGATGTG  CCTGCAAAAA  GTTCCTGAG   CCTGTAAGCA       12590
CTCCAGGTGG  GGAAGTGGAC  AGGAGCCATT  GGTCATAACC  AGACAGAATT       12640
TGGAAACATT  TTCATAAAGC  TCCATGGAGA  GTTTAAAGA   AACATATGTA       12690
GCATGATTTT  GTAGGAGAGG  AAAAAGATTA  TTTAAATAGG  ATTTAAATCA       12740
TGCAACAACG  AGAGTATCAC  AGCCAGGATG  ACCCTTGGGT  CCCATTCCTA       12790
AGACATGGTT  ACTTTATTTT  CCCCTTGTTA  AGACATAGGA  AGACTTAATT       12840
TTTAAACGGT  CAGTGTCCAG  TTGAAGGCAG  AACACTAATC  AGATTTCAAG       12890
GCCCACAACT  TGGGGACTAG  ACCACCTTAT  GTTGAGGGAA  CTCTGCCACC       12940
TGCGTGCAAC  CCACAGCTAA  AGTAAATTCA  ATGACACTAC  TGCCCTGATT       12990
ACTCCTTAGG  ATGTGGTCAA  AACAGCATCA  AATGTTTCTT  CTCTTCCTTT       13040
CCCCAAGACA  GAGTCCTGAA  CCTGTTAAAT  TAAGTCATTG  GATTTACTC        13090
TGTTCTGTTT  ACAGTTACT   ATTTAAGGTT  TTATAAATGT  AAATATATTT       13140
TGTATATTTT  TCTATGAGAA  GCACTTCATA  GGGAGAAGCA  CTTATGACAA       13190
GGCTATTTTT  TAAACCGCGG  TATTATCCTA  ATTAAAAGA   AGATCGGTTT       13240
TTAATAATTT  TTTATTTTCA  TAGGATGAAG  TTAGAGAAAA  TATTCAGCTG       13290
TACACACAAA  GTCTGGTTTT  TCCTGCCCAA  CTTCCCCCTG  GAAGGTGTAC       13340
TTTTTGTTGT  TTAATGTGTA  GCTTGTTTGT  GCCCTGTTGA  CATAAATGTT       13390
TCCTGGGTTT  GCTCTTTGAC  AATAAATGGA  GAAGGAAGGT  CACCCAACTC       13440
CATTGGGCCA  CTCCCCTCCT  TCCCCTATTG  AAGCTCCTCA  AAAGGCTACA       13490
GTAATATCTT  GATACAACAG  ATTCTCTTCT  TTCCCGCCTC  TCTCCTTTCC       13540
GGCGCAACTT  CCAGAGTGGT  GGGAGACGGC  AATCTTTACA  TTTCCCTCAT       13590
CTTTCTTACT  TCAGAGTTAG  CAAACAACAA  GTTGAATGGC  AACTTGACAT       13640
TTTTGCATCA  CCATCTGCCT  CATAGGCCAC  TCTTTCCTTT  CCCTCTGCCC       13690
ACCAAGTCCT  CATATCTGCA  GAGAACCCAT  TGATCACCTT  GTGCCCTCTT       13740
```

```
TTGGGGCAGC CTGTTGAAAC TGAAGCACAG TCTGACCACT CACGATAAAG        13790

CAGATTTTCT CTGCCTCTGC CACAAGGTTT CAGAGTAGTG TAGTCCAAGT        13840

AGAGGGTGGG GCACCCTTTT CTCGCCGCAA GAAGCCCATT CCTATGGAAG        13890

TCTAGCAAAG CAATACGACT CAGCCCAGCA CTCTCTGCCC CAGGACTCAT        13940

GGCTCTGCTG TGCCTTCCAT CCTGGGCTCC CTTCTCTCCT GTGACCTTAA        13990

GAACTTTGTC TGGTGGCTTT GCTGGAACAT TGTCACTGTT TTCACTGTCA        14040

TGCAGGGAGC CCAGCACTGT GGCCAGGATG GCAGAGACTT CCTTGTCATC        14090

ATGGAGAAGT GCCAGCAGGG GACTGGGAAA AGCACTCTAC CCAGACCTCA        14140

CCTCCCTTCC TCCTTTTGCC CATGAACAAG ATGCAGTGGC CCTAGGGGTT        14190

CCACTAGTGT CTGCTTTCCT TTATTATTGC ACTGTGTGAG GTTTTTTTGT        14240

AAATCCTTGT ATTCC                                              14255
```

(2) INFORMATION FOR SEQ ID NO: 2:

(i) SEQUENCE CHARACTERISTICS:
        (A) LENGTH: 218
        (B) TYPE: amino acid
        (D) TOPOLOGY: linear (xi) SEQUENCE DESCRIPTION: SEQ ID NO: 2:

```
Arg Ala Leu Cys Phe Leu Cys Gly Ser Thr Gly Leu Asp Pro Leu
                 5                  10                  15

Ile Phe Cys Ala Cys Cys Glu Pro Tyr His Gln Tyr Cys Val
                20                  25                  30

Gln Asp Glu Tyr Asn Leu Lys His Gly Ser Phe Glu Asp Thr Thr
                35                  40                  45

Leu Met Gly Ser Leu Leu Glu Thr Thr Val Asn Ala Ser Thr Gly
             50                  55                  60

Pro Ser Ser Ser Leu Asn Gln Leu Thr Gln Arg Leu Asn Trp Leu
                65                  70                  75

Cys Pro Arg Cys Thr Val Cys Tyr Thr Cys Asn Met Ser Ser Gly
             80                  85                  90

Ser Lys Val Lys Cys Gln Lys Cys Gln Lys Asn Tyr His Ser Thr
             95                 100                 105

Cys Leu Gly Thr Ser Lys Arg Leu Leu Gly Ala Asp Arg Pro Leu
            110                 115                 120

Ile Cys Val Asn Cys Leu Lys Cys Lys Ser Cys Ser Thr Thr Lys
            125                 130                 135

Val Ser Lys Phe Val Gly Asn Leu Pro Met Cys Thr Gly Cys Phe
            140                 145                 150

Lys Leu Arg Lys Lys Gly Asn Phe Cys Pro Ile Cys Gln Arg Cys
            155                 160                 165

Tyr Asp Asp Asn Asp Phe Asp Leu Lys Met Met Glu Cys Gly Asp
            170                 175                 180

Cys Gly Gln Trp Val His Ser Lys Cys Glu Gly Leu Ser Asp Glu
            185                 190                 195

Gln Tyr Asn Leu Leu Ser Thr Leu Pro Glu Ser Ile Glu Phe Ile
            200                 205                 210

Cys Lys Lys Cys Ala Arg Arg Asn
            215
```

( 2 ) INFORMATION FOR SEQ ID NO: 3:

( i ) SEQUENCE CHARACTERISTICS:
        ( A ) LENGTH: 109
        ( B ) TYPE: amino acid
        ( D ) TOPOLOGY: linear ( x i ) SEQUENCE DESCRIPTION: SEQ ID NO: 3:

```
Asp Thr Arg Met Cys Leu Phe Cys Arg Lys Ser Gly Glu Gly Leu
              5                  10                  15
Ser Gly Glu Glu Ala Arg Leu Leu Tyr Cys Gly His Asp Cys Trp
         20                  25                  30
Val His Thr Asn Cys Ala Met Trp Ser Ala Glu Val Phe Glu Glu
             35                  40                  45
Ile Asp Gly Ser Leu Gln Asn Val His Ser Ala Val Ala Arg Gly
             50                  55                  60
Arg Met Ile Lys Cys Thr Val Cys Gly Asn Arg Gly Ala Thr Val
             65                  70                  75
Gly Cys Asn Val Arg Ser Cys Gly Glu His Tyr His Tyr Pro Cys
             80                  85                  90
Ala Arg Ser Ile Asp Cys Ala Phe Leu Thr Asp Lys Ser Met Tyr
             95                 100                 105
Cys Pro Ala His
            109
```

( 2 ) INFORMATION FOR SEQ ID NO: 4:

( i ) SEQUENCE CHARACTERISTICS:
        ( A ) LENGTH: 210
        ( B ) TYPE: amino acid
        ( D ) TOPOLOGY: linear ( x i ) SEQUENCE DESCRIPTION: SEQ ID NO: 4:

```
Glu Leu Glu Glu Asn Ala Tyr Asp Cys Ala Arg Cys Glu Pro Tyr
              5                  10                  15
Ser Asn Arg Ser Glu Tyr Asp Met Phe Ser Trp Leu Ala Ser Arg
             20                  25                  30
His Arg Lys Gln Pro Ile Gln Val Phe Val Gln Pro Ser Asp Asn
             35                  40                  45
Glu Leu Val Pro Arg Arg Gly Thr Gly Ser Asn Leu Pro Met Ala
             50                  55                  60
Met Lys Tyr Arg Thr Leu Lys Glu Thr Tyr Lys Asp Tyr Val Gly
             65                  70                  75
Val Phe Arg Ser His Ile His Gly Arg Gly Leu Tyr Cys Thr Lys
             80                  85                  90
Asp Ile Glu Ala Gly Glu Met Val Ile Glu Tyr Ala Gly Glu Leu
             95                 100                 105
Ile Arg Ser Thr Leu Thr Asp Lys Arg Glu Arg Tyr Tyr Asp Ser
            110                 115                 120
Arg Gly Ile Gly Cys Tyr Met Phe Lys Ile Asp Asp Asn Leu Val
            125                 130                 135
Val Asp Ala Thr Met Arg Gly Asn Ala Ala Arg Phe Ile Asn His
            140                 145                 150
Cys Cys Glu Pro Asn Cys Tyr Ser Lys Val Val Asp Ile Leu Gly
            155                 160                 165
His Lys His Ile Ile Ile Phe Ala Val Arg Arg Ile Val Gln Gly
            170                 175                 180
Glu Glu Leu Thr Tyr Asp Tyr Lys Phe Pro Phe Glu Asp Glu Lys
            185                 190                 195
```

Ile Pro Cys Ser Cys Gly Ser Lys Arg Cys Arg Lys Tyr Leu Asn
       200                 205                 210

( 2 ) INFORMATION FOR SEQ ID NO: 5:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 5:
        TGAATTTTTT AGGTCCA    17

( 2 ) INFORMATION FOR SEQ ID NO: 6:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 6:
        GAAAAGGTGA GGAGAG    16

( 2 ) INFORMATION FOR SEQ ID NO: 7:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 7:
        TTGGCTCCTT CGGAAAAA    18

( 2 ) INFORMATION FOR SEQ ID NO: 8:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 8:
        TTTAAGGTAA AGGTGT    16

( 2 ) INFORMATION FOR SEQ ID NO: 9:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 9:
        CTCTCTCCAC AGGAGGAT    18

( 2 ) INFORMATION FOR SEQ ID NO: 10:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 10:
ATAGAGGTAA GGCATC    16

( 2 ) INFORMATION FOR SEQ ID NO: 11:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 11:
TTCTTACTAT AGTTTGTG    18

( 2 ) INFORMATION FOR SEQ ID NO: 12:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 12:
ACAAAGGTAC AAAACT    16

( 2 ) INFORMATION FOR SEQ ID NO: 13:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 13:
ATTTCTTAC AGCAGCTG    18

( 2 ) INFORMATION FOR SEQ ID NO: 14:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 14:
GTCTGGGTGA GTTATA    16

( 2 ) INFORMATION FOR SEQ ID NO: 15:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 15:
CTTCTTTTCT AGATCTGT    18

( 2 ) INFORMATION FOR SEQ ID NO: 16:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 16:
AAAGGTACCC AAAA    14

( 2 ) INFORMATION FOR SEQ ID NO: 17:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 17:

```
CTTTGCTTTC AGGAAAC                17
```

( 2 ) INFORMATION FOR SEQ ID NO: 18:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 18:

```
GAAGGTTGGA GTCT                14
```

( 2 ) INFORMATION FOR SEQ ID NO: 19:

( i ) SEQUENCE CHARACTERISTICS:
        ( A ) LENGTH: 189
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 19:

```
GTT  GCA  ATG  CAG  CAG  AAG  CCC  ACG  GCT  TAT  GTC  CGG  CCC  ATG  GAT   45
Val  Ala  Met  Gln  Gln  Lys  Pro  Thr  Ala  Tyr  Val  Arg  Pro  Met  Asp
 5                  10                            15

GGT  CAA  GAT  CAG  GCC  CCT  AGT  GAA  TCC  CCT  GAA  CTG  AAA  CCA  CTG   90
Gly  Gln  Asp  Gln  Ala  Pro  Ser  Glu  Ser  Pro  Glu  Leu  Lys  Pro  Leu
                     20                            25                      30

CCG  GAG  GAC  TAT  CGA  CAG  CAG  ACC  TTT  GAA  AAA  ACA  GAC  TTG  AAA  135
Pro  Glu  Asp  Tyr  Arg  Gln  Gln  Thr  Phe  Glu  Lys  Thr  Asp  Leu  Lys
                     35                            40                      45

GTG  CCT  GCC  AAA  GCC  AAG  CTC  ACC  AAA  CTG  AAG  ATG  CCT  TCT  CAG  180
Val  Pro  Ala  Lys  Ala  Lys  Leu  Thr  Lys  Leu  Lys  Met  Pro  Ser  Gln
                     50                            55                      60

TCA  GTT  GAG                                                              189
Ser  Val  Glu
           63
```

( 2 ) INFORMATION FOR SEQ ID NO: 20:

( i ) SEQUENCE CHARACTERISTICS:
        ( A ) LENGTH: 147
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 20:

```
TTT  GTG  TAT  TGC  CAA  GTC  TGT  TGT  GAG  CCC  TTC  CAC  AAG  TTT  TGT   45
Phe  Val  Tyr  Cys  Gln  Val  Cys  Cys  Glu  Pro  Phe  His  Lys  Phe  Cys
                      5                            10                      15

TTA  GAG  GAG  AAC  GAG  CGC  CCT  CTG  GAG  GAC  CAG  CTG  GAA  AAT  TGG   90
Leu  Glu  Glu  Asn  Glu  Arg  Pro  Leu  Glu  Asp  Gln  Leu  Glu  Asn  Trp
                     20                            25                      30

TGT  TGT  CGT  CGT  TGC  AAA  TTC  TGT  CAC  GTT  TGT  GGA  AGG  CAA  CAT  135
```

| Cys | Cys | Arg | Arg | Cys | Lys | Phe | Cys | His | Val | Cys | Gly | Arg | Gln | His |
|-----|-----|-----|-----|-----|-----|-----|-----|-----|-----|-----|-----|-----|-----|-----|
|     |     |     |     | 35  |     |     |     | 40  |     |     |     |     |     | 45  |

CAG GCT ACA AAG                                                                                                          147
Gln Ala Thr Lys
              49

( 2 ) INFORMATION FOR SEQ ID NO: 21:

( i ) SEQUENCE CHARACTERISTICS:
        ( A ) LENGTH: 132
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 21:

GAA AAA CCA CCT CCG GTC AAT AAG CAG GAG AAT GCA GGC ACT TTG 45
Glu Lys Pro Pro Pro Val Asn Lys Gln Glu Asn Ala Gly Thr Leu
              5                   10                  15

AAC ATC TTC AGC ACT CTC TCC AAT GGC AAT AGT TCT AAG CAA AAA 90
Asn Ile Phe Ser Thr Leu Ser Asn Gly Asn Ser Ser Lys Gln Lys
              20                  25                  30

ATT CCA GCA GAT GGA GTC CAC AGG ATC AGA GTG GAC TTT AAG     132
Ile Pro Ala Asp Gly Val His Arg Ile Arg Val Asp Phe Lys
              35                  40

( 2 ) INFORMATION FOR SEQ ID NO: 22:

( i ) SEQUENCE CHARACTERISTICS:
        ( A ) LENGTH: 270
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 22:

ACC TAC TCC AAT GAA GTC CAT TGT GTT GAA GAG ATT CTG AAG GAA 45
Thr Tyr Ser Asn Glu Val His Cys Val Glu Glu Ile Leu Lys Glu
              5                   10                  15

ATG ACC CAT TCA TGG CCG CCT CCT TTG ACA GCA ATA CAT ACG CCT 90
Met Thr His Ser Trp Pro Pro Pro Leu Thr Ala Ile His Thr Pro
              20                  25                  30

AGT ACA GCT GAG CCA TCC AAG TTT CCT TTC CCT ACA AAG GAC TCT 135
Ser Thr Ala Glu Pro Ser Lys Phe Pro Phe Pro Thr Lys Asp Ser
              35                  40                  45

CAG CAT GTC AGT TCT GTA ACC CAA AAC CAA AAA CAA TAT GAT ACA 180
Gln His Val Ser Ser Val Thr Gln Asn Gln Lys Gln Tyr Asp Thr
              50                  55                  60

TCT TCA AAA ACT CAC TCA AAT TCT CAG CAA GGA ACG TCA TCC ATG 225
Ser Ser Lys Thr His Ser Asn Ser Gln Gln Gly Thr Ser Ser Met
              65                  70                  75

CTC GAA GAC GAC CTT CAG CTC AGT GAC AGT GAG GAC AGT GAC AGT 270
Leu Glu Asp Asp Leu Gln Leu Ser Asp Ser Glu Asp Ser Asp Ser
              80                  85                  90

( 2 ) INFORMATION FOR SEQ ID NO: 23:

( i ) SEQUENCE CHARACTERISTICS:
        ( A ) LENGTH: 336
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 23:

```
GTT GCA ATG CAG CAG AAG CCC ACG GCT TAT GTC CGG CCC ATG GAT    45
Val Ala Met Gln Gln Lys Pro Thr Ala Tyr Val Arg Pro Met Asp
            5                   10                  15

GGT CAA GAT CAG GCC CCT AGT GAA TCC CCT GAA CTG AAA CCA CTG    90
Gly Gln Asp Gln Ala Pro Ser Glu Ser Pro Glu Leu Lys Pro Leu
            20                  25                  30

CCG GAG GAC TAT CGA CAG CAG ACC TTT GAA AAA ACA GAC TTG AAA   135
Pro Glu Asp Tyr Arg Gln Gln Thr Phe Glu Lys Thr Asp Leu Lys
            35                  40                  45

GTG CCT GCC AAA GCC AAG CTC ACC AAA CTG AAG ATG CCT TCT CAG   180
Val Pro Ala Lys Ala Lys Leu Thr Lys Leu Lys Met Pro Ser Gln
            50                  55                  60

TCA GTT GAG TTT GTG TAT TGC CAA GTC TGT TGT GAG CCC TTC CAC   225
Ser Val Glu Phe Val Tyr Cys Gln Val Cys Cys Glu Pro Phe His
            65                  70                  75

AAG TTT TGT TTA GAG GAG AAC GAG CGC CCT CTG GAG GAC CAG CTG   270
Lys Phe Cys Leu Glu Glu Asn Glu Arg Pro Leu Glu Asp Gln Leu
            80                  85                  90

GAA AAT TGG TGT TGT CGT CGT TGC AAA TTC TGT CAC GTT TGT GGA   315
Glu Asn Trp Cys Cys Arg Arg Cys Lys Phe Cys His Val Cys Gly
            95                  100                 105

AGG CAA CAT CAG GCT ACA AAG                                    336
Arg Gln His Gln Ala Thr Lys
            110
```

( 2 ) INFORMATION FOR SEQ ID NO: 24:

( i ) SEQUENCE CHARACTERISTICS:
        ( A ) LENGTH: 402
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 24:

```
GAA AAA CCA CCT CCG GTC AAT AAG CAG GAG AAT GCA GGC ACT TTG    45
Glu Lys Pro Pro Pro Val Asn Lys Gln Glu Asn Ala Gly Thr Leu
            5                   10                  15

AAC ATC TTC AGC ACT CTC TCC AAT GGC AAT AGT TCT AAG CAA AAA    90
Asn Ile Phe Ser Thr Leu Ser Asn Gly Asn Ser Ser Lys Gln Lys
            20                  25                  30

ATT CCA GCA GAT GGA GTC CAC AGG ATC AGA GTG GAC TTT AAG ACC   135
Ile Pro Ala Asp Gly Val His Arg Ile Arg Val Asp Phe Lys Thr
            35                  40                  45

TAC TCC AAT GAA GTC CAT TGT GTT GAA GAG ATT CTG AAG GAA ATG   180
Tyr Ser Asn Glu Val His Cys Val Glu Glu Ile Leu Lys Glu Met
            50                  55                  60

ACC CAT TCA TGG CCG CCT CCT TTG ACA GCA ATA CAT ACG CCT AGT   225
Thr His Ser Trp Pro Pro Pro Leu Thr Ala Ile His Thr Pro Ser
            65                  70                  75

ACA GCT GAG CCA TCC AAG TTT CCT TTC CCT ACA AAG GAC TCT CAG   270
Thr Ala Glu Pro Ser Lys Phe Pro Phe Pro Thr Lys Asp Ser Gln
            80                  85                  90

CAT GTC AGT TCT GTA ACC CAA AAC CAA AAA CAA TAT GAT ACA TCT   315
His Val Ser Ser Val Thr Gln Asn Gln Lys Gln Tyr Asp Thr Ser
            95                  100                 105

TCA AAA ACT CAC TCA AAT TCT CAG CAA GGA ACG TCA TCC ATG CTC   360
Ser Lys Thr His Ser Asn Ser Gln Gln Gly Thr Ser Ser Met Leu
            110                 115                 120

GAA GAC GAC CTT CAG CTC AGT GAC AGT GAG GAC AGT GAC AGT        402
```

```
Glu Asp Asp Leu Gln Leu Ser Asp Ser Glu Asp Ser Asp Ser
            125                 130
```